US007166565B2

(12) United States Patent
Caswell et al.

(10) Patent No.: US 7,166,565 B2
(45) **Date of Patent: *Jan. 23, 2007**

(54) LAUNDRY SYSTEM HAVING UNITIZED DOSING

(75) Inventors: Debra Sue Caswell, Beijing (CN); Robert Gary Welch, Mason, OH (US); Mark William Ridyard, Newcastle upon Tyne (GB); Edward Sayers, North Shields (GB); David William York, Newcastle upon Tyne (GB); Daniel James Dufton, Newcastle upon Tyne (GB); Simon Howe, Tyne and Wear (GB); Johan Eshuis, Antwerp (BE); Angelina Pena-Romero, Tervuren (BE); Christophe Laudamiel-Pellet, New York, NY (US); Wundriari Hoffmann, Frimley (GB); George Endel Deckner, Cincinnati, OH (US); Errol Hoffman Wahl, Cincinnati, OH (US); Ruth Anne Murphy, Cinicinnati, OH (US); Charles Albert Hensley, deceased, late of Cincinnati, OH (US); by Betty Jean Hensley, legal representative, Cincinnati, OH (US); Toan Trinh, Maineville, OH (US); Jiten Odhavji Dihora, Hamilton, OH (US); Ellen Schmidt Baker, Cincinnati, OH (US); Janet Sue Littig, Fairfield, OH (US); Timothy James Schroeder, Mason, OH (US); Steven Louis Diersing, Cincinnati, OH (US); Malcolm McClaren Dodd, Tyne and Wear (GB); Lois Sara Gallon, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 77 days.

This patent is subject to a terminal disclaimer.

(21) Appl. No.: 11/105,798

(22) Filed: Apr. 14, 2005

(65) Prior Publication Data

US 2005/0176611 A1 Aug. 11, 2005

Related U.S. Application Data

(63) Continuation of application No. 10/925,749, filed on Aug. 25, 2004, which is a continuation of application No. 09/838,867, filed on Apr. 20, 2001, now abandoned.

(60) Provisional application No. 60/203,472, filed on May 11, 2000.

(51) Int. Cl.
*A61K 7/46* (2006.01)

(52) U.S. Cl. .......................... 510/438; 510/439; 512/4

(58) Field of Classification Search ................ 510/101, 510/439, 441; 512/4
See application file for complete search history.

(56) References Cited

U.S. PATENT DOCUMENTS

| | | | | |
|---|---|---|---|---|
| 4,026,131 | A | 5/1977 | Dugger et al. | |
| 4,176,079 | A | 11/1979 | Guerry et al. | |
| 4,253,842 | A | 3/1981 | Ehrlich | |
| 4,264,466 | A | 4/1981 | Carleton et al. | |
| 4,365,853 | A | 12/1982 | Ehrlich | |
| 4,416,791 | A | 11/1983 | Haq | |
| 4,557,852 | A | 12/1985 | Schulz et al. | |
| 4,765,916 | A | 8/1988 | Ogar, Jr. et al. | |
| 5,004,556 | A * | 4/1991 | Julemont et al. | 510/304 |
| 5,160,654 | A | 11/1992 | Falou et al. | |
| 5,955,057 | A | 9/1999 | Maunder et al. | |
| 6,037,319 | A | 3/2000 | Dickler et al. | |
| 6,121,215 | A | 9/2000 | Rau | |
| 6,410,500 | B1 | 6/2002 | Haerer et al. | |
| 6,468,950 | B1 | 10/2002 | Kawasaki et al. | |
| 2003/0104969 | A1 | 6/2003 | Casewell et al. | |

FOREIGN PATENT DOCUMENTS

DE 2 263 940 7/1974

(Continued)

*Primary Examiner*—John R. Hardee
(74) *Attorney, Agent, or Firm*—David V. Upite

(57) ABSTRACT

Compositions, articles and methods are provided for supplying fabric care benefits to clothing or fabrics in an automated washing machine and by manual washing. The fabric care compositions preferably have less than about 5% detergent surfactants, more preferably less than 3%, even more preferably less than 1% and are most preferably free of detergent surfactants. Similarly, the fabric care compositions preferably have less than about 5% fabric softener actives, more preferably less than 3%, even more preferably less than 1% and are most preferably free of detergent surfactants. The laundry articles can take a variety of forms in a variety of physical states all of which will rapidly dispense a unitized amount of one or more selected fabric care agents to a wash and/or rinse bath solution during the laundering process under a variety of conditions. The invention also pertains to laundry kits that contain a variety of such articles and instructions concerning their use. Likewise, methods for preparing a customized laundry solution to obtain a specific fabric care benefit selected based on the user's personal preferences and/or the fabric care needs of the fabrics being laundered are also provided. Further, the present invention also concerns methods for assisting a consumer in identifying the unitized articles to be used in preparing a laundry solution that will impart desired fabric care benefits as well as merchandising displays for dispensing the articles, assembling customized laundry kits and instructing the consumer on the selection and use of laundry articles.

19 Claims, 1 Drawing Sheet

FOREIGN PATENT DOCUMENTS

| | | | | |
|---|---|---|---|---|
| EP | 0 391 087 | A1 | | 10/1990 |
| EP | 0 628 627 | A1 | | 12/1994 |
| EP | 0 812 808 | A1 | | 12/1997 |
| GB | 2 235 206 | A | | 2/1991 |
| JP | 05-168686 | | * | 7/1993 |
| WO | WO 93/08255 | A1 | | 4/1993 |
| WO | WO 94/04656 | | | 3/1994 |
| WO | WO 97/16516 | | | 5/1997 |
| WO | WO 97/34982 | A1 | | 9/1997 |
| WO | WO 98/12291 | A2 | | 3/1998 |
| WO | WO 98/16614 | A1 | | 4/1998 |
| WO | WO 98/39406 | | * | 9/1998 |
| WO | WO 99/09136 | A1 | | 2/1999 |
| WO | WO 99/18926 | A1 | | 4/1999 |
| WO | WO 99/35234 | A1 | | 7/1999 |

* cited by examiner

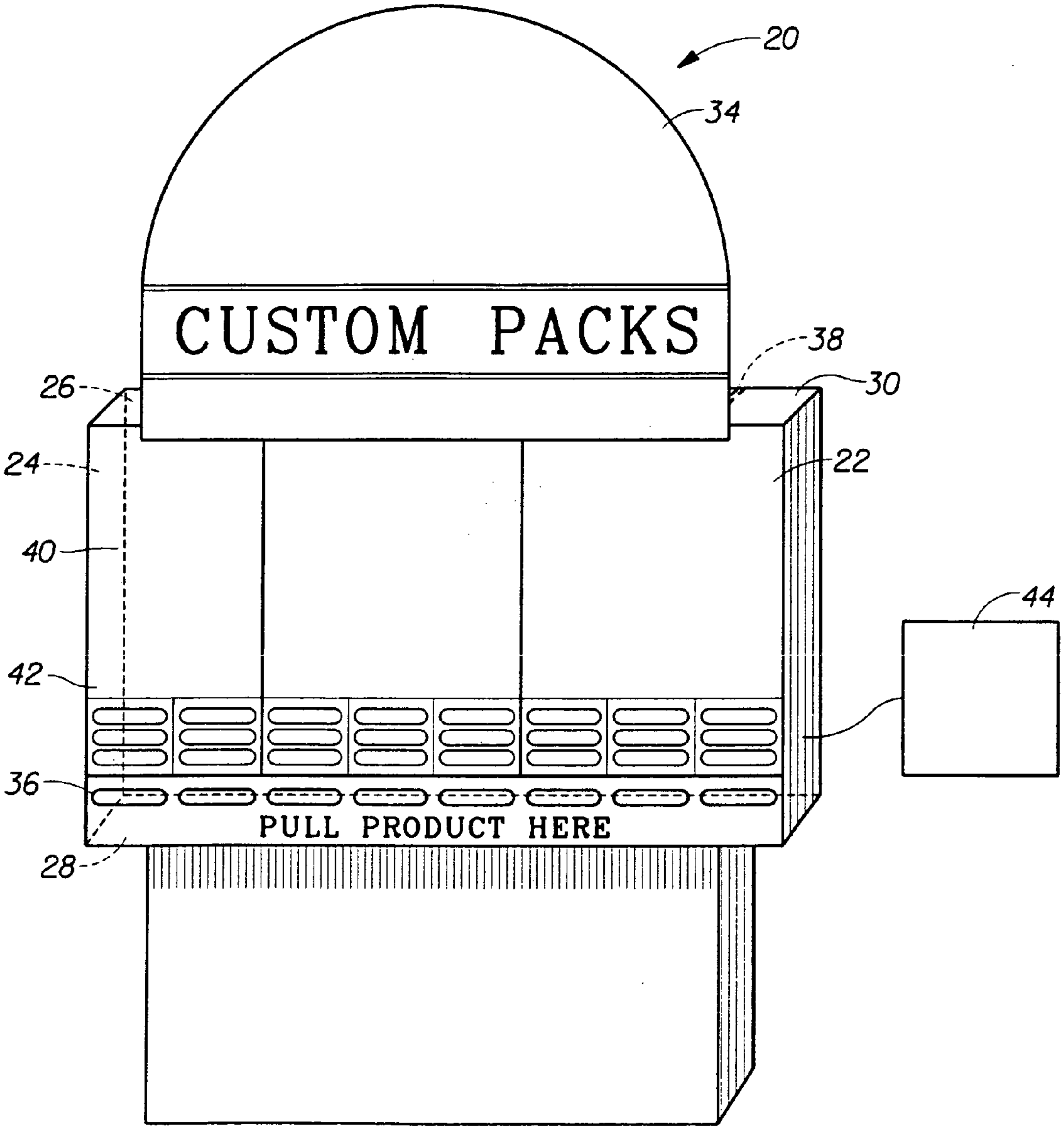
20
34
CUSTOM PACKS
38
26
30
24
22
40
44
42
36
PULL PRODUCT HERE
28

LAUNDRY SYSTEM HAVING UNITIZED DOSING

CROSS REFERENCE RELATED TO CASE

This application is a continuation of allowed U.S. patent application Ser. No. 10/925,749, filed Aug. 25, 2004, which is a continuation of U.S. patent application Ser. No. 09/838,867, now abandoned, filed Apr. 20, 2001 which claims the benefit of U.S. Provisional Application Ser. No. 60/203,472 filed May 11, 2000, the disclosures of which are incorporated herein by reference.

TECHNICAL FIELD

The present invention relates to compositions, articles and methods for supplying fabric care benefits to clothing or fabrics in an automated washing machine and by manual washing. The articles take a variety of forms and will rapidly dispense a unitized amount of one or more selected fabric care agents to a wash and/or rinse bath solution during the laundering process under a variety of conditions. The invention also pertains to laundry kits that contain a variety of such articles and instructions concerning their use. Likewise, methods for preparing a customized laundry solution to obtain fabric care benefits selected based on the user's personal preferences and/or the fabric care needs of the fabrics being laundered are also provided. Further, the present invention also concerns methods for assisting a consumer in identifying the unitized articles to be used in preparing a laundry solution that will impart desired fabric care benefits as well as merchandising displays for dispensing the articles, assembling and compiling customized laundry kits and instructing the consumer on the selection and use of the articles and compositions.

1. Background of the Invention

The home laundering operation can provide an opportunity to treat fabrics with a variety of materials that will impart a desirable benefit or quality to the fabrics ("fabric care benefit") during laundering. At each stage of the laundering operation, whether presoaking, washing, or rinsing, fabrics are to varying degrees found in contact with water which provides a preferred medium for delivery of fabric care compositions.

Delivery of fabric care agents during the laundering operation is not, however, accomplished without certain difficulties. Surfactants are generally employed during the presoaking and washing steps for the purpose of removing materials (soil) from the fabric. Simultaneous deposition onto fabrics of fabric care agents can, therefore prove troublesome. While some of these problems can be overcome by conditioning fabrics in the dryer (see, for example, Geiser; U.S. Pat. No. 3,442,692, issued May 6, 1969), it is well known that an efficient and uniform deposition of fabric care compositions in the dryer is difficult to achieve. Further, such deposition is primarily limited to the surface of the fabrics and is therefore, particularly inefficient at delivering actives to the non-surface regions of the fabrics.

The distribution of fabric care agents in a rinse bath solution is likewise not without difficulty. Because most rinse cycles use cold water, typically in the region of less than about 30° C., the dissolution and dispersion of solid, semi-solid and granular fabric care actives into a rinse solution is inhibited. To obtain an efficient distribution of fabric care actives through a rinse bath or other cold water laundry solution, most have resorted to the use of liquid compositions, particularly in combination with fabric softener actives. However, attempts to provide such fabric softening compositions with even moderate concentrations of non-softener actives have commonly encountered phase stability and viscosity problems. While stabilizers and other systems have been developed to overcome some of these issues, there remains a need for methods and compositions that will allow a consumer to distribute a wide array of fabric care actives in desired concentrations, preferably high concentrations, in the rinse bath or other cold water laundry solutions.

Thus, attempts have been made to improve the distribution of fabric care agents during the laundering process as well as to increase the types and quantities of fabric care actives that may be delivered. Some of these attempts are found in the prior art references listed subsequently herein. In spite of these developments, there is a continuing need for methods and compositions that are suitable for efficiently and effectively delivering a variety of fabric care agents to wash and rinse bath solutions and fabrics during the home laundering operation. It has been discovered with the present invention that such delivery may be accomplished with compositions, and articles made therefrom, that will rapidly dissolve and disperse in wash and/or rinse bath solutions across a broad range of temperatures and in the presence of a variety of other materials including detergents and/or fabric softener actives.

Further, because bulk-packaged wash and rinse-added compositions do not allow consumers the flexibility to prepare laundry solutions according to their own specifications or preferences, there is a need for methods and compositions that will allow the consumer the flexibility to prepare a customized laundry solution for each load of laundry based on the consumer's preferences and/or the fabric care needs of the fabrics to be laundered.

Further still, the present invention is based in part on the discovery that fabrics can receive excellent fabric care benefits from an article releasably containing a fabric care active or mixture of actives dispersed in the solution while the fabrics are being laundered. These enhanced fabric care benefits are achieved while offering significant additional convenience and flexibility.

Accordingly, it is an object of the present invention to provide compositions, and articles made therefrom, which can be added to a washing machine, tub or other apparatus used to launder clothes, to treat fabrics in a superior manner concurrently with the home washing operation. The articles are constructed such that a unitized amount of a fabric care composition containing one or more fabric care actives is rapidly released after the article is dispensed in either a wash and/or rinse bath solution to insure effective distribution of the active in solution and/or deposition on the fabrics being laundered. It is a further object of the present invention to provide methods for treating and laundering fabrics through the use of such unitized articles during the home laundering process.

It is still another object of the present invention to provide a laundry kit containing multiple articles and optional instructions with which a consumer may customize a laundry solution to provide benefits in accordance with the consumer's personal preferences and the fabric care needs of their clothes. Therefore, it is also an object of the present invention to provide methods that will enable the consumer to prepare a customized laundry solution that will contain an effective amount of a fabric care active or mixture of actives that will impart a fabric care benefit chosen by the consumer.

It is yet another object of the present invention to provide methods for assisting a consumer in identifying and dispensing fabric care articles to be used by the consumer in preparing a customized laundry solution. Likewise, it is an object of the present invention to provide merchandising displays for use in instructing the consumer in the selection and use of fabric care articles, in dispensing such articles to the consumer, and for use by the consumer in assembling laundry kits according to their personal preferences and/or the fabric care needs of their fabrics.

It is still yet another object of the present invention to provide methods for conveying information concerning the fabric care needs of a fabric to a consumer to assist the consumer in caring for the fabric using the compositions, articles and methods described herein.

It is yet another object of the present invention to provide an effervescent article for providing improved delivery of an effective amount of a fabric care active to a laundry wash and/or rinse solution. Likewise, it is also an object of the present invention to provide a perfume containing article that will provide improved distribution and deposition of an effective amount of a selected perfume to a laundry wash and/or rinse solution.

These and other objects and advantages of the present invention will become obvious from the following disclosure.

2. Description of the Prior Art

U.S. Pat. No. 4,253,842, Ehrlich, DETERGENT COMPOSITIONS AND WASHING METHODS INCLUDING AND UTILIZING SEPARATE TABLETS OF COMPONENTS, issued Mar. 3, 1981 disclosing compositions and methods relating to unitized detergent additives for use in the wash.

U.S. Pat. No. 3,627,693, Scarpelli, LAYERED CAPSULE WALLS AND A METHOD FOR MANUFACTURING THEM, issued Dec. 14, 1971; U.S. Pat. No. 3,896,033, Grimm III, ENCAPSULATED FABRIC SOFTENER, issued Jul. 22, 1975; U.S. Pat. No. 3,930,191, Vincent, INORGANIC PIGMENT-LOADED POLYMERIC MICROCAPSULAR SYSTEM, issued Dec. 30, 1975; U.S. Pat. No. 4,018,688, Pracht et al., CAPSULES, PROCESS OF THEIR PREPARATION AND FABRIC CONDITIONING COMPOSITION CONTAINING SAID CAPSULES, issued Apr. 19, 1977; U.S. Pat. No. 4,081,384, Pracht, SOLVENT-FREE CAPSULES AND FABRIC CONDITIONING COMPOSITIONS CONTAINING SAME, issued Mar. 28, 1978; U.S. Pat. No. 4,244,836, Frensch et al., PROCESS FOR MANUFACTURING MICROCAPSULES OF POLYVINYL ALCOHOL WITH LIQUID WATER-INSOLUBLE CONTENT, issued Jan. 13, 1981; U.S. Pat No 4,234,627, Schilling, FABRIC CONDITIONING COMPOSITIONS, issued No. 18, 1980; U.S. Pat. No. 4,615,814, Winetzky, POROUS SUBSTRATE WITH ABSORBED ANTISTAT OR SOFTENER, USED WITH DETERGENT, issued Oct. 7, 1986; U.S. Pat. No. 5,073,295, Bruttel et al., ENCAPSULATED FLUORESCENT WHITENING AGENT, PHOTOACTIVATOR OR ANTI-MICROBIAL AGENT, issued Dec. 17, 1991; U.S. Pat. No. 5,141,664, Corring et al., CLEAR DETERGENT GEL COMPOSITIONS HAVING OPAQUE PARTICLES DISPERSED THEREIN, issued Aug. 25, 1992; U.S. Pat. No. 5,342,626, Winston, Jr., et al., COMPOSITION AND PROCESS FOR GELATIN-FREE SOFT CAPSULES, issued Aug. 30, 1994; U.S. Pat. No. 5,691,303, Pan et al., PERFUME DELIVERY SYSTEM COMPRISING ZEOLITES, issued Nov. 25, 1997; U.S. Pat. No. 5,846,927, Vasudevan, MATRIX OR CORE SHELL ENZYME CAPSULE COMPOSITIONS COMPRISING DEFINED DENSITY MODIFYING SOLIDS SURROUNDED BY DEFINED CORE STRUCTURANT MATERIAL, issued Dec. 8, 1998; and European Patent Application No. 0 332 175 A2, Takizawa et al., METHOD OF PRODUCING MICROENCAPSULATION, filed Aug. 3, 1989 each relating to compositions, microencapsulation of such compositions, and methods relating to their manufacture and use.

U.S. Pat. No. 3,892,905, Albert, COLD WATER SOLUBLE PLASTIC FILMS, issued Jul. 1, 1975; U.S. Pat. No. 4,073,833, Laughlin, ENCAPSULATION PROCESS, issued Feb. 14, 1978; U.S. Pat. No. 4,082,678, Pracht et al., FABRIC CONDITIONING ARTICLES AND PROCESS, issued Apr. 4, 1978; U.S. Pat. No. 4,108,600, Wong, FABRIC CONDITIONING ARTICLES AND PROCESSES, issued, Aug. 22, 1978; U.S. Pat. No. 4,176,079, Guerry et al., WATER-SOLUBLE ENZYME-CONTAINING ARTICLE, issued Nov. 27, 1979; U.S. Pat. No. 4,416,791, Haq, PACKAGING FILM AND PACKAGING OF DETERGENT COMPOSITIONS THEREWITH, issued Nov. 22, 1983; U.S. Pat. No. 4,481,326, Sonenstein, WATER SOLUBLE FILMS OF POLYVINYL ALCOHOL POLYVINYL PYRROLIDONE, Nov. 6, 1984; U.S. Pat. No. 4,544,693, Surgant, WATER-SOLUBLE FILM, issued Oct. 1, 1985; U.S. Pat. No 4,557,852, Schultz et al., POLYMER SHEET FOR DELIVERING LAUNDRY CARE ADDITIVE AND LAUNDRY CARE PRODUCT FORMED FROM SAME, issued Dec. 10, 1985; U.S. Pat. No. 4,654,395, WATER-SOLUBLE POLYMER SHEET FOR DELIVERING LAUNDRY CARE ADDITIVE AND LAUNDRY CARE PRODUCT FORMED FROM SAME, issued Mar. 31, 1987; U.S. Pat. No. 4,765,916, Ogar, Jr. et al., POLYMER FILM COMPOSITION FOR RINSE RELEASE OF WASH ADDITIVES, issued Aug. 23, 1988; U.S. Pat. No. 4,801,636, Smith et al., RINSE SOLUBLE POLYMER FILM COMPOSITION FOR WASH ADDITIVES, issued Jan. 31, 1989; U.S. Pat. No. 4,972,017, Smith et al., RINSE SOLUBLE POLYMER FILM COMPOSITION FOR WASH ADDITIVES, issued Nov. 20, 1990; U.S. Pat. No. 5,272,191, Ibrahim et al., COLD WATER SOLUBLE FILMS AND FILM FORMING COMPOSITIONS, issued Dec. 21, 1993; European Patent Application No. 0 382 464 A2, Akay, COATING PROCESS, filed Sep. 2, 1990; International Application No. PCT/GB97/00838, Publication No. WO 97/35537, Brown, IMPROVEMENTS IN OR RELATING TO ENCAPSULATION, filed Mar. 25, 1997; and International Application No. PCT/EP98/05050, Publication No. WO 99/09136, Gassenmeier et al., HIGH-DOSE FRAGRANCED SHAPED BODIES, filed Aug. 8, 1998 each relating to compositions for water soluble films, their manufacture and use in forming articles for the delivery of laundry additives.

U.S. Pat. No. 4,642,197, Kruse et al., PROCESS FOR THE PRODUCTION OF A WASHING ADDITIVE IN TABLET FORM, issued Feb. 10, 1987; U.S. Pat. No. 4,678,661, Gergely et al., EFFERVESCENT COMPOSITION AND METHOD OF MAKING SAME, Jul. 7, 1987; U.S. Pat. No. 5,858,959, Surutzidis et al., DELIVERY SYSTEMS COMPRISING ZEOLITES AND A STARCH HYDROLYSATE GLASS, issued Jan. 12, 1999; U.S. Pat. No. 5,965,515, Rau, COATED AMINE FUNCTIONALITY-CONTAINING MATERIALS, issued Oct. 12, 1999; and U.S. Pat. No. 5,993,854, Needleman et al., EXOTHERMIC EFFERVESCENT COMPOSITION FOR IMPROVED FRAGRANCE DISPERSION, issued Nov. 30, 1999, WO 93/08255, Kruse et al. SCENT TABLETS, Oct. 5, 1992, each relating to compositions and their use in forming tablets and other solid articles for the delivery of laundry additives.

SUMMARY OF THE INVENTION

The instant invention is based on the discovery that superior fabric conditioning and treatment, convenience and flexibility can be achieved by dispensing an effective amount of a laundry additive composition in a laundry wash and/or rinse bath. This is accomplished in the present invention by providing a composition comprising a fabric care active or mixture of actives that is between about 1% and about 99% by weight of the composition, said composition having less than about 5%, preferably less than about 3% and more preferably less than about 1% detergent surfactant, and less than about 5%, preferably less than about 3% and more preferably less than about 1% fabric softener active. Even more preferred is a fabric care composition free of detergent surfactant and fabric softener actives.

The present invention likewise provides an article containing a unitized dose of such a fabric care composition that may be used to customize a laundry solution to deliver one or more fabric care benefits desired by a consumer or needed for proper fabric care of the consumers fabrics. An article of the present invention contains a unitized dose of a composition comprising a fabric care active or mixture of actives that is between about 1% and about 99% by weight of the composition, said composition having less than about 5%, preferably less than about 3% and more preferably less than about 1% detergent surfactant, and less than about 5%, preferably less than about 3% and more preferably less than about 1% fabric softener active. Even more preferred is a fabric care article that is free of detergent surfactant and fabric softener actives. An article of the present invention will weigh between about 0.05 g and about 60 g and will rapidly dissolve in aqueous solutions under a variety of temperatures and in the presence of other materials, e.g. detergents or fabric softeners. The articles of the present invention may optionally have a binder, carrier, emulsifier, dissolution agent, disintegration agent, non-detergent surfactant, film, coating, and identification means, and mixtures thereof.

More specifically, the present invention provides for improved deposition of fragrance on fabrics by providing a laundry perfume article wherein the active is a perfume or mixture of perfume ingredients between about 1% and about 99% of the article and less than about 5%, preferably less than about 3% and more preferably less than about 1% detergent surfactant, and less than about 5%, preferably less than about 3% and more preferably less than about 1% fabric softener active. Even more preferred is a perfume article that is free of detergent surfactant and fabric softener actives. The laundry perfume article of the present invention may optionally contain an emulsifier, perfume fixative, perfume binder, perfume carrier and mixtures thereof.

Further, the present invention provides an effervescent laundry article for dispensing in a laundry wash and/or rinse bath solution, the article having a fabric care composition comprising an active or mixture of actives that is between about 1% and about 99% of the composition and less than about 5%, preferably less than about 3% and more preferably less than about 1% detergent surfactant, and less than about 5%, preferably less than about 3% and more preferably less than about 1% fabric softener active, the composition having an effervescent system comprising an acid, carbon dioxide source and optionally a binder. Even more preferred is an effervescent laundry article that is free of detergent surfactant and fabric softener actives, the article having a fabric care composition comprising an active or mixture of actives that is between about 1% and about 99% of the composition and an effervescent system comprising an acid, carbon dioxide source and optionally a binder. Optionally, the effervescent system will comprise an effervescent granule to improve the release of the active or actives from the effervescent laundry article.

The present invention also provides a laundry kit which a consumer may use to prepare a customized laundry solution to deliver one or more desired fabric care benefits. The kit comprises a plurality of unitized doses of fabric care compositions, each composition having a fabric care active or mixture of actives between about 1% and about 99% by weight of the composition and having less than about 5%, preferably less than about 3% and more preferably less than about 1% detergent surfactant actives, and less than about 5%, preferably less than about 3% and more preferably less than about 1% fabric softener active. Prefereably, each unitized dose or article in the kit weighs between about 0.05 g and about 60 g. The laundry kit of the present invention may optionally contain multiple doses or articles of similar and/or dissimilar fabric care compositions. The laundry kit of the present invention may optionally contain a detergent and/or fabric softener composition for use in combination with the articles in preparing a customized laundry solution.

Therefore, the present invention also provides a customized laundry solution prepared with the fabric care additive compositions and articles described herein. The customized laundry solution comprises water and one or more unitized doses or articles containing a fabric care composition having a fabric care active or mixture of actives between about 1% and about 99% by weight of the composition and having less than about 5% detergent surfactant actives and less than about 5% fabric softener actives before being dispensed in the laundry solution. Each of these unitized doses or articles having a weight of between about 0.05 g and about 60 g before being dispensed in solution. The customized laundry solution of the present invention may optionally contain detergent and/or fabric softening actives.

A process aspect of the present invention provides methods for delivering a pre-measured or unitized amount of a fabric care active or mixture of actives to a laundry solution. The methods include the steps of providing a laundry article having a unitized amount of a fabric care composition having a fabric care active that is between about 1% and about 99% by weight of the article and having less than about 5% detergent surfactants, preferably less than about 3% and more preferably less than about 1%, and less than about 5% fabric softener active, preferably less than about 3% and more preferably less than about 1%, and dispensing the article in a laundry solution. The article may be dispensed into the solution by placing the article directly in the solution or by placing it in a dispensing device that is provided with the washing machine or a self-contained device that is placed in the washing machine tub during the laundering operation. In addition, when a pre-soak laundry solution is desired, the article is dispensed in a tub with the fabrics. When a washing machine dispensing device is used, it is preferred that the article have a diameter or width between about 1 mm and about 9 mm and more preferably between about 5 mm and about 8 mm. When a self-contained dispensing device is used, it is preferred that the diameter or width be between about 1 mm and about 20 mm, more preferably between about 5 mm and about 19 mm, and even more preferably between about 8 mm and 18 mm.

In another process aspect, the present invention provides methods for customizing a laundry solution for a load of fabrics to deliver a fabric care benefit. The methods comprise the steps of selecting a desired fabric care benefit and dispensing into a wash and/or rinse bath solution an article containing a unitized dose of a fabric care composition that will provide that benefit. The dispensed article having a fabric care composition having a fabric care active or mixture of actives between about 1% and about 99% by weight of the composition and less than about 5%, preferably less than about 3% and more preferably less than about 1% detergent surfactant, and less than about 5%, preferably less than about 3% and more preferably less than about 1% fabric softener active. The article dispensed in the laundry solution having a weight of between about 0.05 g and about 60 g before being dispensed in that solution.

In another process aspect, the invention provides methods for identifying a system of laundry products to a consumer for their use in customizing the laundering of fabrics. The methods comprise the steps of collecting information regarding a fabric care benefit or combination of benefits desired by the consumer, selecting a system of laundry products comprising a detergent and/or fabric softener and an article containing a unitized dose of a fabric care composition having a fabric care active or mixture of actives that is between about 1% and about 99% of the composition and less than about 5%, preferably less than about 3% and more preferably less than about 1% detergent surfactant, and less than about 5%, preferably less than about 3% and more preferably less than about 1% fabric softener active, and providing information to said consumer identifying the selected system of laundry products. The system selected is based upon the information collected from the consumer. Optionally, such information may be collected and provided through the use of a computer or through other collection means.

In a further process aspect, the invention provides methods for dispensing packaged laundry additive products for use by individuals in customizing a laundry solution to deliver a fabric care benefit desired by the individual. The method comprises the step of providing a supply of at least two different types of packaged articles, each having a unitized dose of a fabric care composition, each fabric care composition having a fabric care active or mixture of actives that is between about 1% and about 99% of the composition. The method also includes the step of providing a dispensing device for housing the supply of packaged articles that is capable of allowing an individual to select one or more types of fabric enhancing articles and removing the packaged article from the dispensing device.

The present invention also provides a merchandising display for use in a retail environment that comprises a supply of fabric care articles, each article containing a unitized dose of a fabric care composition having a fabric care active or mixture of actives that is about 1% to about 99% of the fabric care composition, and each article having a weight between about 0.05 g and about 60 g. The display of the present invention further comprises information to assist the consumer in selecting a fabric care article for use in combination with a detergent, a fabric softener or other fabric care article to achieve one or more fabric care benefits desired by the consumer. Optionally, the display may include a computer or other interactive means to assist the consumer in selecting a fabric care article.

In still another process aspect, the invention provides an interactive method for dispensing fabric care articles for use by individuals in customizing a laundry solution to deliver a desired fabric care benefit. The method comprises the step of providing a supply of a detergent and/or fabric softener and one or more fabric care articles, each article having a unitized dose of a fabric care composition that has a fabric care active or mixture of actives that is between about 1% and about 99% of the composition. The method further includes the steps of providing a dispensing device for housing the supply and for communicating information to a consumer describing a suitable laundry system comprising a detergent and/or fabric softener and at least one fabric care article. The dispensing device may optionally be capable of allowing a consumer to select and remove the detergent and/or fabric softener and one or more fabric care articles from the supply housed within the dispensing device.

In yet a further process aspect, the present invention provides methods for providing information concerning the fabric care needs for fabrics to a consumer. These methods comprise the steps of identifying one or more fabric care compositions useful in the proper laundering of the fabric and providing information identifying those compositions with the distribution of the fabric so that the consumer may properly maintain that fabric using the compositions, articles and methods of the present invention.

All percentages, ratios and proportions herein are by weight, unless otherwise specified. All temperatures are in degrees Celsius (° C.) unless otherwise specified. All documents cited are, in relevant part, incorporated herein by reference.

DETAILED DESCRIPTION OF THE PREFERRED EMBODIMENTS

The present invention concerns the unitized delivery of fabric care actives to a laundry solution, regardless of whether the delivery is to a wash and/or rinse bath solution, the temperature of the solution or the presence of other materials in the solution. The delivery of a fabric care active or mixture of actives to a laundry solution in a unitized dose enables a consumer to impart specific fabric care benefits to the fabrics while maximizing convenience and flexibility.

Because the fabric care actives are dispensed through unitized dosing isolated from detergent and fabric softening actives, fabric care actives that could not previously be formulated with other materials may be used in the present invention. Likewise, fabric care that are presently formulated with detergent and/or fabric softeners in limited amounts because of stability issues or otherwise, may be used in higher, more effective concentrations in the compositions and articles of the present invention. For example, the level of perfume that can be incorporated into a concentrated liquid fabric softener that is a dispersion is typically less than about 2%. Perfumes may be incorporated into the articles of the present invention to deliver virtually any level of perfume to the laundry solution desired by the consumer. Further, the use of unitized dosing to separate actives that are unstable in combination with one another, eliminates the need for stabilizers, viscosity modifiers and the like, further simplifying the compositions of the present invention.

The invention is described herein in terms of the fabric care compositions, the different dosage forms and articles that may be utilized to deliver those compositions, the different actives or mixtures of actives that may be included in those compositions as well as the different methods relating to the use, manufacture and selection of the dosage forms and compositions.

I. Fabric Care Additive Compositions

The fabric care compositions of the present invention comprise in their most simplified form a fabric care active or mixture of actives that is between about 1% and about 99%, preferably from about 2% to about 80%, more preferably from between about 4% and about 60% and most preferably from about 10% to about 50% by weight of the composition. Further, the composition of the present invention should contain less than about 5%, more preferably less than about 3%, and even more preferably less than about 1% detergent surfactant and less than about 5%%, more preferably less than about 3%, and even more preferably less than about 1% fabric softening active. Most preferably the fabric care compositions of the present invention will be free of these types of actives. While the compositions may be used in solutions containing detergent and fabric softener actives, the compositions themselves prior to their delivery to solution will preferably not contain these types of materials.

As used herein, "detergent actives" refers to detergent surfactants, detergent builders, chlorine bleaching agents and mixtures thereof. "Detergent surfactants" should be understood to refer to surfactants, primarily anionic surfactants, that are most well known for their detersive action in removing soil and stains from fabrics. "Fabric softening actives" as used herein is a reference to the class of compounds that may be deposited on fabrics through a rinse solution or in the dryer to provide a softening effect to the laundered fabrics and includes cationic softening compounds among other softeners that are well known in the art.

The fabric care actives used in the compositions and articles of the present invention may be virtually any active or mixture of actives that will produce a fabric care benefit when deposited on a fabric. It is preferred that the fabric care actives used in the present invention be less water soluble to promote their deposition from the laundry solution to the fabrics. As such, it is preferred that where the active is an organic compound it will have a ClogP equal to or greater than about 3. Where the fabric care active consists of a mixture of organic actives it is preferred that at least about 25%, more preferably at least about 50%, even more preferably at least about 75%, of the actives in the mixture, have a ClogP equal to or greater than about 3.

As described in U.S. Pat. No. 5,500,138, issued Mar. 19, 1996 to Bacon and Trinh, incorporated herein by reference, the ClogP of an active is a reference to the "calculated" octanol/water partitioning coefficient of the active and serves as a measure of the hydrophobicity of the active. The ClogP of an active may be calculated according to the methods quoted in "The Hydrophobic Fragmental Constant" R. F. Rekker, Elsevier, Oxford or Chem. Rev, Vol. 71, No. 5, 1971, C. Hansch and A. I. Leo, or by using a ClogP program from Daylight Chemical Information Systems, Inc. Such a program also lists experimental logP values when they are available in the Pomona92 database. The "calculated logP" (ClogP) may be determined by the fragment approach of Hansch and Leo (cf., A. Leo in Comprehensive Medicinal Chemistry, Vol. 4, C. Hansch, P. G. Sammens, J. B. Taylor, and C. A. Ramsden, Eds. p 295, Pergamon Press, 1990). The fragment approach is based on the chemical structure of each compound and takes into account the numbers and types of atoms, the atom connectivity, and chemical bonding. The ClogP values, which are the most reliable and widely used estimates for this physicochemical property, can be used instead of the experimental $_1$logP values in the selection of active ingredients to define a minimum level of hydrophobicity which corresponds with efficient deposition of the active on fabrics.

Because the compositions of the present invention may be used in a variety of dose forms or articles for delivering the fabric care active to a wash and/or rinse bath solution, the composition should rapidly dissolve or disperse in the bath under a variety of conditions. Specifically, where the composition is in the form of a solid, it is preferable that the composition be capable of dissolving in an aqueous bath at about 30° C. within between about 0.5 min and about 15 min with minimal agitation. More preferably, dissolution of such a solid composition will occur in less than 10 min and most preferably within 6 min of placing the composition in the bath. Likewise, it is preferable that a solid form of the composition will rapidly dissolve in cold water, preferably dissolving in an aqueous bath at about 10° C. between about 0.5 min and about 15 min with minimal agitation. More preferably, dissolution of such a solid composition will occur in less than 10 min and most preferably within 6 min of placing the composition in such a cold water bath.

The fabric care active or mixture of actives that may be used in the compositions of the present invention may include perfumes, bodying agents, drape and form control agents, smoothness agents, static control agents, wrinkle control agents, sanitization agents, drying agents, stain resistance agents, soil release agents, malodor control agents, dye fixatives, dye transfer inhibitors, color maintenance agents, anti-fading agents, whiteness enhancers, anti-abrasion agents, fabric integrity agents, anti-wear agents, color appearance restoration agents, brightness restoration agents, defoamers and anti-foaming agents, rinse aids, UV protection agents, sun fade inhibitors, insect repellents, mite control agents, enzymes and mixtures thereof. Additional description concerning the fabric care actives that may be used in the compositions and articles of the present invention is provided herein.

In addition, the compositions of the present invention may optionally include various agents to aid in the manufacture of the dose form or article containing these compositions. These agents may include carriers, binders, coatings, disintegration agents, effervescent systems, emulsifying agents and dispersing agents that will aid in the release and distribution of the actives in the laundry solution. Each of these agents is described in more detail below.

The compositions of the present invention may also include a solvent or mixture of solvents. When used, it is preferred that the solvent is an organic solvent or a mixture of water and organic solvent.

Active Ingredients

A. Perfumes

1. Perfume Active

As used herein the term "perfume" is used to indicate any odoriferous material that is subsequently released into the aqueous bath and/or onto fabrics contacted therewith. The perfume will most often be liquid at ambient temperatures. A wide variety of chemicals are known for perfume uses, including materials such as aldehydes, ketones, and esters. More commonly, naturally occurring plant and animal oils and exudates comprising complex mixtures of various chemical components are known for use as perfumes. The perfumes herein can be relatively simple in their compositions or can comprise highly sophisticated complex mixtures of natural and synthetic chemical components, all chosen to provide any desired odor. Typical perfumes can comprise, for example, woody/earthy bases containing exotic materials such as sandalwood, civet and patchouli oil. The perfumes can be of a light floral fragrance, e.g. rose extract, violet extract, and lilac. The perfumes can also be formulated to provide desirable fruity odors, e.g. lime, lemon, and orange. Further, it is anticipated that so-called "designer fragrances" that are typically applied directly to the skin will be used when desired by the consumer. Likewise, the perfumes delivered in the compositions and articles of the present invention may be selected for an aromatherapy effect, such as providing a relaxing or invigorating mood. As such, any material that exudes a pleasant or otherwise desirable odor can be used as a perfume active in the compositions and articles of the present invention.

Preferably, at least about 25%, more preferably at least about 50%, even more preferably at least about 75%, by weight of the perfume is composed of fragrance material selected from the group consisting of aromatic and aliphatic esters having molecular weights from about 130 to about 250; aliphatic and aromatic alcohols having molecular weights from about 90 to about 240; aliphatic ketones having molecular weights from about 150 to about 260; aromatic ketones having molecular weights from about 150 to about 270; aromatic and aliphatic lactones having molecular weights from about 130 to about 290; aliphatic aldehydes having molecular weights from about 140 to about 200; aromatic aldehydes having molecular weights from about 90 to about 230; aliphatic and aromatic ethers having molecular weights from about 150 to about 270; and condensation products of aldehydes and amines having molecular weights from about 180 to about 320; and essentially free from nitromusks and halogenated fragrance materials.

More preferably, at least about 25%, more preferably at least about 50%, most preferably at least about 75%, by weight of the perfume is composed of fragrance material selected from the group consisting of:

| Common Name | Chemical Type | Chemical Name | Approx. M.W. |
|---|---|---|---|
| Adoxal | aliphatic aldehyde | 2,6,10-trimethyl-9-undecen-1-al | 210 |
| allyl amyl glycolate | ester | allyl amyl glycolate | 182 |
| allyl cyclohexane propionate | ester | allyl-3-cyclohexyl propionate | 196 |
| amyl acetate | ester | 3-methyl-1-butanol acetate | 130 |
| amyl salicylate | ester | amyl salicylate | 208 |
| anisic aldehyde | aromatic aldehyde | 4-methoxy benzaldehyde | 136 |
| aurantiol | schiff base | condensation product of methyl anthranilate and hydroxycitronellal | 305 |
| bacdanol | aliphatic alcohol | 2-ethyl-4-(2,2,3-trimethyl-3-cyclopenten-1-yl)-2-buten-1-ol | 208 |
| benzaldehyde | aromatic aldehyde | benzaldehyde | 106 |
| benzophenone | aromatic ketone | benzophenone | 182 |
| Benzyl acetate | ester | benzyl acetate | 150 |
| Benzyl salicylate | ester | benzyl salicylate | 228 |
| beta damascone | aliphatic ketone | 1-(2,6,6-trimethyl-1-cyclohexen-1-yl)-2-buten-1-one | 192 |
| beta gamma hexanol | alcohol | 3-hexen-1-ol | 100 |
| buccoxime | aliphatic ketone | 1,5-dimethyl-oxime bicyclo[3,2,1] octan-8-one | 167 |
| Cedrol | alcohol | octahydro-3,6,8,8-tetramethyl-1H-3A,7-methanoazulen-6-ol | 222 |
| cetalox | ether | dodecahydro-3A,6,6,9A-tetramethylnaphtho[2,1B]-furan | 236 |
| cis-3-hexenyl acetate | ester | cis-3-hexenyl acetate | 142 |
| cis-3-hexenyl salicylate | ester | beta, gamma-hexenyl salicylate | 220 |
| citronellol | alcohol | 3,7-dimethyl-6-octenol | 156 |
| citronellyl nitrile | nitrile | geranyl nitrile | 151 |
| clove stem oil | natural | | |
| coumarin | lactone | coumarin | 146 |
| cyclohexyl salicylate | ester | cyclohexyl salicylate | 220 |
| cymal | aromatic aldehyde | 2-methyl-3-(para iso propyl phenyl)propionaldehyde | 190 |
| decyl aldehyde | aliphatic aldehyde | decyl aldehyde | 156 |
| delta damascone | aliphatic ketone | 1-(2,6,6-trimethyl-3-cyclohexen-1-yl)-2-buten-1-one | 192 |
| dihydromyrcenol | alcohol | 3-methylene-7-methyl octan-7-ol | 156 |
| dimethyl benzyl carbinyl acetate | ester | dimethyl benzyl carbinyl acetate | 192 |
| ethyl vanillin | aromatic aldehyde | ethyl vanillin | 166 |
| ethyl-2-methyl butyrate | ester | ethyl-2-methyl butyrate | 130 |
| ethylene brassylate | macrocyclic lactone | ethylene tridecan-1,13-dioate | 270 |
| eucalyptol | aliphatic epoxide | 1,8-epoxy-para-menthane | 154 |

-continued

| Common Name | Chemical Type | Chemical Name | Approx. M.W. |
|---|---|---|---|
| eugenol | alcohol | 4-allyl-2-methoxy phenol | 164 |
| exaltolide | macrocyclic lactone | cyclopentadecanolide | 240 |
| flor acetate | ester | dihydro-nor-cyclopentadienyl acetate | 190 |
| florhydral | aromatic aldehyde | 3-(3-isopropylphenyl) butanal | 190 |
| frutene | ester | dihydro-nor-cyclopentadienyl propionate | 206 |
| galaxolide | ether | 1,3,4,6,7,8-hexahydro-4,6,6,7,8,8-hexamethylcyclopenta-gamma-2-benzopyrane | 258 |
| gamma decalactone | lactone | 4-N-hepty-4-hydroxybutanoic acid lactone | 170 |
| gamma dodecalactone | lactone | 4-N-octyl-4-hydroxy-butanoic acid lactone | 198 |
| geraniol | alcohol | 3,7-dimethyl-2,6-octadien-1-ol | 154 |
| geranyl acetate | ester | 3,7-dimethyl-2,6-octadien-1-yl acetate | 196 |
| geranyl nitrile | ester | 3,7-diemthyl-2,6-octadienenitrile | 149 |
| helional | aromatic aldehyde | alpha-methyl-3,4, (methylenedioxy) hydrocinnamaldehyde | 192 |
| heliotropin | aromatic aldehyde | heliotropin | 150 |
| Hexyl acetate | ester | hexyl acteate | 144 |
| Hexyl cinnamic aldehyde | aromatic aldehyde | alpha-n-hexyl cinnamic aldehyde | 216 |
| Hexyl salicylate | ester | hexyl salicylate | 222 |
| hydroxyambran | aliphatic alcohol | 2-cyclododecyl-propanol | 226 |
| hydroxycitronellal | aliphatic aldehdye | hydroxycitronellal | 172 |
| ionone alpha | aliphatic ketone | 4-(2,6,6-trimethyl-1-cyclohexenyl-1-yl)-3-buten-2-one | 192 |
| ionone beta | aliphatic ketone | 4-(2,6,6-trimethyl-1-cyclohexen-1-yl)-3-butene-2-one | 192 |
| ionone gamma methyl | aliphatic ketone | 4-(2,6,6-trimethyl-2-cyclohexyl-1-yl)-3-methyl-3-buten-2-one | 206 |
| iso E super | aliphatic ketone | 7-acetyl-1,2,3,4,5,6,7,8-octahydro-1,1,6,7,tetramethyl naphthalene | 234 |
| iso eugenol | ether | 2-methoxy-4-(1-propenyl) phenol | 164 |
| iso jasmone | aliphatic ketone | 2-methyl-3-(2-pentenyl)-2-cyclopenten-1-one | 166 |
| koavone | aliphatic aldehyde | acetyl di-isoamylene | 182 |
| Lauric aldehyde | aliphatic aldehyde | lauric aldehyde | 184 |
| lavandin | natural | | |
| lavender | natural | | |
| lemon CP | natural | major component d-limonene | |
| d-limonene/orange terpenes | alkene | 1-methyl-4-iso-propenyl-1-cyclohexene | 136 |
| linalool | alcohol | 3-hydroxy-3,7-dimethyl-1,6-octadiene | 154 |
| linalyl acetate | ester | 3-hydroxy-3,7-dimethyl-1,6-octadiene acetate | 196 |
| lrg 201 | ester | 2,4-dihydroxy-3,6-dimethyl benzoic acid methyl ester | 196 |
| Lyral | aliphatic aldehyde | 4-(4-hydroxy-4-methyl-pentyl) 3-cylcohexene-1-carboxaldehyde | 210 |
| majantol | aliphatic alcohol | 2,2-dimethyl-3-(3-methylphenyl)-propanol | 178 |

-continued

| Common Name | Chemical Type | Chemical Name | Approx. M.W. |
|---|---|---|---|
| mayol | alcohol | 4-(1-methylethyl) cyclohexane methanol | 156 |
| methyl anthranilate | aromatic amine | methyl-2-aminobenzoate | 151 |
| methyl beta naphthyl ketone | aromatic ketone | methyl beta naphthyl ketone | 170 |
| methyl cedrylone | aliphatic ketone | methyl cedrenyl ketone | 246 |
| methyl chavicol | ester | 1-methyloxy-4,2-propen-1-yl benzene | 148 |
| methyl dihydro jasmonate | aliphatic ketone | methyl dihydro jasmonate | 226 |
| methyl nonyl acetaldehyde | aliphatic aldehyde | methyl nonyl acetaldehyde | 184 |
| Musk indanone | aromatic ketone | 4-acetyl-6-tert butyl-1,1-dimethyl indane | 244 |
| Nerol | alcohol | 2-cis-3,7-dimethyl-2,6-octadien-1-ol | 154 |
| nonalactone | lactone | 4-hydroxynonanoic acid, lactone | 156 |
| norlimbanol | aliphatic alcohol | 1-(2,2,6-trimethyl-cyclohexyl)-3-hexanol | 226 |
| orange CP | natural | major component d-limonene | |
| P. T. bucinal | aromatic aldehyde | 2-methyl-3(para tert butylphenyl) propionaldehyde | 204 |
| para hydroxy phenyl butanone | aromatic ketone | para hydroxy phenyl butanone | 164 |
| patchouli | natural | | |
| phenyl acetaldehyde | aromatic aldehyde | 1-oxo-2-phenylethane | 120 |
| phenyl acetaldehyde dimethyl acetal | aromatic aldehyde | phenyl acetaldehyde dimethyl acetal | 166 |
| phenyl ethyl acetate | ester | phenyl ethyl acetate | 164 |
| phenyl ethyl alcohol | alcohol | phenyl ethyl alcohol | 122 |
| phenyl ethyl phenyl acetate | ester | 2-phenylethyl phenyl acetate | 240 |
| phenyl hexanol/phenoxanol | alcohol | 3-methyl-5-phenylpentanol | 178 |
| polysantol | aliphatic alcohol | 3,3-dimethyl-5-(2,2,3-trimethyl-3-cyclopenten-1-yl)-4-penten-2-ol | 221 |
| Prenyl acetate | ester | 2-methylbuten-2-ol-4-acetate | 128 |
| rosaphen | aromatic alcohol | 2-methyl-5-phenyl pentanol | 178 |
| sandalwood | natural | | |
| alpha-terpinene | aliphatic alkane | 1-methyl-4-iso-propylcyclohexadiene-1,3 | 136 |
| terpineol (alpha terpineol and beta terpineol) | alcohol | para-menth-1-en-8-ol, para-menth-1-en-1-ol | 154 |
| terpinyl acetate | ester | para-menth-1-en-8-yl acetate | 196 |
| tetra hydro linalool | aliphtic alcohol | 3,7-dimethyl-3-octanol | 158 |
| tetrahydromyrcenol | aliphatic alcohol | 2,6-dimethyl-2-octanol | 158 |
| Tonalid/musk plus | aromatic ketone | 7-acetyl-1,1,3,4,4,6-hexamethyl tetralin | 258 |
| undecalactone | lactone | 4-N-heptyl-4-hydroxybutanoic acid lactone | 184 |
| undecavertol | alcohol | 4-methyl-3-decen-5-ol | 170 |
| undecyl aldehyde | aliphatic aldehyde | undecanal | 170 |
| undecylenic aldehyde | aliphatic aldehyde | undecylenic aldehyde | 168 |
| vanillin | aromatic aldehyde | 4-hydroxy-3-methoxybenzaldehyde | 152 |
| verdox | ester | 2-tert-butyl cyclohexyl acetate | 198 |
| vertenex | ester | 4-tert-butyl cyclohexyl acetate | 198 |

and mixtures thereof.

During the laundry process, a substantial amount of perfume that is added to the wash and/or the rinse cycle is lost with the water and in the subsequent drying cycle (either line drying or machine drying). This has resulted in both a waste of unusable perfume that are not deposited on the laundered fabrics, and a contribution to the general air pollution from the release of volatile organic compounds to the air. It is therefore preferable that at least about 25%, more preferably at least about 50%, even more preferably at least about 75%, by weight of the perfume is composed of enduring perfume ingredients. These enduring perfume ingredients are characterized by their boiling points (B.P.) and their ClogP value. The enduring perfume ingredients of this invention have a B.P, measured at the normal, standard pressure of 760 mm Hg, of about 240° C. or higher, preferably of about 250° C. or higher, and a ClogP of about 2.7 or higher, preferably of about 2.9 or higher, and even more preferably of about 3.0 or higher. The enduring perfume ingredients tend to be substantive and remain on fabric after the laundry washing and drying process.

The boiling points of many perfume ingredients are given in, e.g., "Perfume and Flavor Chemicals (Aroma Chemicals)," Steffen Arctander, published by the author, 1969, incorporated herein by reference. Other boiling point values can be obtained from different chemistry handbooks and data bases, such as the Beilstein Handbook, Lange's Handbook of Chemistry, and the CRC Handbook of Chemistry and Physics. When a boiling point is given only at a different pressure, usually lower pressure than the normal pressure of 760 mm Hg, the boiling point at normal pressure can be approximately estimated by using boiling point-pressure nomographs, such as those given in "The Chemist's Companion," A. J. Gordon and R. A. Ford, John Wiley & Sons Publishers, 1972, pp. 30–36. The boiling point values can also be estimated via a computer program that is described in "Development of a Quantitative Structure—Property Relationship Model for Estimating Normal Boiling Points of Small Multifunctional Organic Molecules", David T. Stanton, Journal of Chemical Information and Computer Sciences, Vol. 40, No. 1, 2000, pp. 81–90.

Perfume compositions composed of enduring perfume ingredients that have both a boiling point of about 250° C. or higher and a ClogP of about 3.0 or higher, are very effectively deposited on fabrics and remain substantive on fabrics after rinsing and drying.

Non-limiting examples of the preferred enduring perfume ingredients of the present invention include: benzyl salicylate, adoxal, allyl cyclohexane propionate (trade name for allyl-3-cyclohexyl propionate), alpha damascone, ambrettolide (trade name for oxacycloheptadec-10-en-2-one), ambretone (trade name for 5-cyclohexadecen-1-one), ambroxan, amyl cinnamic aldehyde,amyl cinnamic aldehyde dimethyl acetal, amyl salicylate, ambrinol 20t (trade name for 2,5,5-trimethyl-octahydro-2-naphthol), iso E super (trade name for 7-acetyl-1,2,3,4,5,6,7,8-octahydro-1,1,6,7, tetramethylnaphthalene), anandol (trade name for 2-ethyl-4-(2,2,3-trimethyl-3-cyclopenten-1-yl)-2-buten-1-ol), aurantiol (trade name for hydroxycitronellal-methyl anthranilate), benzyl benzoate, nirvanol (trade name for 4-penten-2-ol,3,3-dimethyl-5-(2,2,3 trimethyl-3-cyclopenten-1-yl)-), undecalactone (trade name for 4-N-heptyl-4-hydroxybutanoic acid lactone), beta naphthol methyl ether, bourgeonal (trade name for 3-(4-tert butylphenyl)-propanal), cyclohexadecenone (trade name for cis-/trans-cyclohexadec-8-en-1-one), caryophyllene extra, methyl cedrylone (trade name for methyl cedrenyl ketone), neobutenone (trade name for 4-penten-1-one, 1-(5,5-dimethyl-1-cyclohexen-1-yl)), cedramber, cedac (trade name for cedrynyl acetate), cedrol (trade name for octahydro-3,6,8,8-tetramethyl-1H-3A,7-methanoazulen-6-ol), musk C-14 (trade name for ethylene dodecane dioate), cis-3-hexenyl salicylate (trade name for beta, gamma-hexenyl salicylate), citrathal, citronellyl propionate, galaxolide (trade name for 1,3,4,6,7,8-hexahydro-4,6,6,7,8,8-hexamethlycyclopenta-gamma-2-benzopyrane), cyclohexyl salicylate, cymal (trade name for 2-methyl-3-(para iso propyl phenyl)propionaldehyde), damascone beta (trade name for 1-(2,6,6-trimethylcyclohexen-1-yl)-2-buten-1-one), damascenone (trade name for 1-(2,6,6-trimethyl-1, 3-cyclohexadien-1-yl)-2-buten-1-one), delta damascone (trade name for 1-(2,6,6-trimethyl-3-cyclo-hexen-1-yl)-2-buten-1-one), dihydro iso jasmonate, diphenyl methane, dupical (trade name for 4-(tricyclo(5.2.1.0 2,6)decylidene-8)-butanal), diphenyl oxide, gamma-dodecalactone (trade name for 4-N-octyl-4-hydroxy-butanoic acid lactone), delta-dodecalactone, ethyl cinnamate, ebanol, ethylene brassylate (trade name for ethylene tridecan-1,13-dioate), florhydral (trade name for 3-(3-isopropylphenyl) butanol), habanolide (trade name for oxacyclohexadec-12+13-en-2-one), hexyl cinnamic aldehyde (trade name for alpha-n-hexyl cinnamic aldehyde), hexyl salicylate, hydroxyambran (trade name for 2-cyclododecyl-propanol), ionone alpha (trade name for 4-(2,6,6-trimethyl-1-cyclohexenyl-1-yl)-3-buten-2-one), ionone beta (trade name for 4-(2,6,6-trimethyl-1-cyclohexen-1-yl)-3-butene-2-one), ionone gamma methyl (trade name for 4-(2,6,6-trimethyl-2-cyclohexyl-1-yl)-3-methyl-3-buten-2-one), ionone methyl, iralia, iso butyl quinoline, lauric aldehyde, p. t. bucinal (trade name for 2-methyl-3 (para tertbutylphenyl) propionaldehyde), musk ketone, musk indanone (trade name for 4-acetyl-6-tert butyl-1,1-dimethyl indane), musk plus (trade name for 7-acetyl-1,1, 3,4,4,6-hexamethyl tetralin), octalynol (trade name for 1-naphthalenol, 1,2,3,4,4a,5,8,8a,octahydro-2,2,6,8-tetramethyl), ozonil (trade name for tridecen-2-nitrile), phantolide (trade name for 5-acetyl-1,1,2,3,3,6-hexamethylindan), phenafleur (trade name for cyclohexyl phenyl ethyl ether), phenyl ethyl benzoate, phenyl ethyl phenyl acetate (trade name for 2-phenylethyl phenyl acetate), vetiveryl acetate, sandalwood, amyl benzoate, amyl cinnamate, cadinene, cedryl acetate, cedryl formate, cinnamyl cinnamate, cyclamen aldehyde, exaltolide (trade name for 15-hydroxypentadecanoic acid, lactone), geranyl anthranilate, hexadecanolide, hexenyl salicylate, linayl benzoate, 2-methoxy naphthalene, methyl cinnamate, methyl dihydrojasmonate, beta-methyl napthyl ketone, musk tibetine, myristicin, delta-nonalactone, oxahexadecanolide-10, oxahexadecanolide-11, patchouli alcohol, phenyl heptanol, phenyl hexanol (trade name for 3-methyl-5-phenylpentanol), alpha-santalol, thibetolide (trade name for 15-hydroxypentadecanoic acid, lactone), delta-undecalactone, gamma-undecalactone, yara-yara, methyl-N-methyl anthranilate, benzyl butyrate, benzyl iso valerate, citronellyl isobutyrate, delta nonalactone, dimethyl benzyl carbinyl acetate, dodecanal, geranyl acetate (trade name for 3,7-dimethyl-2,6-octadien-1-yl acetate), geranyl isobutyrate, gamma-ionone, para-isopropyl phenylacetaldehyde, tonalid (trade name for 7-acetyl-1,1,3,4,4,6-hexamethyl tetralin), iso-amyl salicylate, ethyl undecylenate, benzophenone, beta-caryophyllene, dodecalactone, lilial (trade name for para-tertiary-butyl-alpha-methyl hydrocinnamic aldehyde), and mixtures thereof.

The preferred perfume compositions used in the present invention contain at least 4 different enduring perfume ingredients, preferably at least 5 enduring perfume ingredients, more preferably at least 6 different enduring perfume ingredients, and even more preferably at least 7 different enduring perfume ingredients. Most common perfume ingredients which are derived from natural sources, are composed of a multitude of components. When each such material is used in the formulation of the preferred perfume compositions of the present invention, it is counted as one single ingredient, for the purpose of defining the invention.

In the perfume art, some materials having no odor or very faint odor are used as diluents or extenders. Non-limiting examples of these materials are dipropylene glycol, diethyl phthalate, triethyl citrate, isopropyl myristate, and benzyl benzoate. These materials are used for, e.g., diluting and stabilizing some other perfume ingredients.

The perfume compositions of the present invention can also comprise some low odor detection threshold perfume ingredients. The odor detection threshold of an odorous material is the lowest vapor concentration of that material which can be olfactorily detected. The odor detection threshold and some odor detection threshold values are discussed in, e.g., "Standardized Human Olfactory Thresholds", M. Devos et al, IRL Press at Oxford University Press, 1990, and "Compilation of Odor and Taste Threshold Values Data", F. A. Fazzalari, editor, ASTM Data Series DS 48A, American Society for Testing and Materials, 1978, both of said publications being incorporated by reference. The use of small amounts of perfume ingredients that have low odor detection threshold values can improve perfume odor character, even though they are not as substantive as the enduring perfume ingredients disclosed hereinabove.

Perfume ingredients having a significantly low detection threshold, useful in the perfume composition of the present invention, are selected from the group consisting of allyl amyl glycolate, ambrox (trade name for 1,5,5,9-tetramethyl-1,3-oxatricyclotridecane), anethole, bacdanol (trade name for 2-ethyl-4-(2,2,3-trimethyl-3-cyclopenten-1-yl)-2-buten-1-ol), benzyl acetone, benzyl salicylate, butyl anthranilate, calone, cetalox (trade name for dodecahydro-3A,6,6,9A-tetramethylnaphtho[2,1B]-furan), cinnamic alcohol, coumarin, cyclogalbanate, Cyclal C (trade name for 3-cyclohexene-1-carboxaldehyde, 3,5-dimethyl-), cymal (trade name for 2-methyl-3-(para iso propylphenyl)propionaldehyde), damascenone (trade name for 1-(2,6,6-trimethyl-1,3-cyclohexadien-1-yl)-2-buten-1-one), alpha-damascone, 4-decenal, dihydro isojasmonate, gamma-dodecalactone (trade name for 4-N-octyl-4-hydroxy-butanoic acid lactone), ebanol, ethyl anthranilate, ethyl-2-methyl butyrate, ethyl methylphenyl glycidate, ethyl vanillin, eugenol (trade name for 4-allyl-2-methoxy phenol), flor acetate (trade name for dihydro-nor-cyclopentadienyl acetate), florhydral (trade name for 3-(3-isopropylphenyl) butanol), fructone (trade name for ethyl-2-methyl-1,3-dioxolane-2-acetate), frutene (trade name for dihydro-nor-cyclopentadienyl propionate), heliotropin, herbavert, cis-3-hexenyl salicylate (trade name for beta, gamma-hexenyl salicylate), indole, ionone alpha (trade name for 4-(2,6,6-trimethyl-1-cyclohexenyl-1-yl)-3-buten-2-one), ionone beta (trade name for 4-(2,6,6-trimethyl-1-cyclohexen-1-yl)-3-butene-2-one), iso cyclo citral, isoeugenol (trade name for 2-methoxy-4-(1-propenyl)phenol), alpha-isomethylionone, keone, lilial (trade name for para-tertiary butyl alpha-methyl hydrocinnamic aldehyde), linalool (trade name for 3-hydroxy-3,7-dimethyl-1,6-octadiene), lyral (trade name for 4-(4-hydroxy-4-methyl-pentyl) 3-cylcohexene-1-carboxaldehyde), methyl anthranilate (trade name for methyl-2-aminobenzoate), methyl dihydrojasmonate, methyl heptine carbonate, methyl isobutenyl tetrahydropyran, methyl beta naphthyl ketone, methyl nonyl ketone, beta naphthol methyl ether, nerol (trade name for 2-cis-3,7-dimethyl-2,6-octadien-1-ol), para-anisic aldehyde, para hydroxy phenyl butanone, phenyl acetaldehyde (trade name for 1-oxo-2-phenylethane), gamma-undecalactone, undecylenic aldehyde, vanillin (trade name for 4-hydroxy-3-methoxybenzaldehyde), and mixtures thereof. These materials are preferably present at low levels in addition to the enduring perfume ingredients, typically less than about 20%, preferably less than about 15%, more preferably less than about 10%, by weight of the total perfume compositions of the present invention. It is understood that these materials can be used a levels higher than 20% and even up to 100% of the total perfume composition. Some enduring perfume ingredients also have low odor detection threshold.

The following non-limiting examples exemplify enduring perfume compositions:

Enduring Perfume A

| Perfume Ingredients | Wt. % |
|---|---|
| Benzyl Salicylate | 10 |
| Coumarin | 5 |
| Ethyl Vanillin | 2 |
| Ethylene Brassylate | 10 |
| Galaxolide | 15 |
| Hexyl Cinnamic Aldehyde | 20 |
| Gamma Methyl Ionone | 10 |
| Lilial | 15 |
| Methyl Dihydrojasmonate | 5 |
| Patchouli | 5 |
| Tonalid | 3 |
| Total | 100 |

Enduring Perfume B

| Perfume Ingredients | Wt. % |
|---|---|
| Vertinex (4-tertiary butyl cyclohexyl acetate) | 3 |
| Methyl cedrylone | 2 |
| Verdox | 3 |
| Galaxolide | 14 |
| Tonalid | 5 |
| Hexyl salicylate | 4 |
| Benzyl salicylate | 4 |
| Hexyl cinnamic aldehyde | 6 |
| P. T. Bucinal | 6 |
| Musk indanone | 7 |
| Ambrettolide | 2 |
| Sandela | 5 |
| Phentolide | 2 |
| Vetivert acetate | 4 |
| Patchouli | 2 |
| Geranyl phenylacetate | 6 |
| Okoumal | 6 |
| Citronellyl acetate | 3 |
| Citronellol | 5 |
| Phenyl ethyl alcohol | 5 |
| Ethyl vanillin | 2 |
| Coumarin | 1 |
| Flor acetate | 1 |
| Linalool | 2 |
| Total | 100 |

The perfume active may also include pro-fragrances such as acetal profragrances, ketal pro-fragrances, ester pro-fragrances (e.g., digeranyl succinate), hydrolyzable inorganic-organic pro-fragrances, and mixtures thereof. These pro-fragrances may release the perfume material as a result of simple hydrolysis, or may be pH-change-triggered pro-fragrances (e.g. pH drop) or may be enzymatically releasable pro-fragrances.

The perfume active may also include one or more pro-fragrances, pro-perfumes, pro-accords, and mixtures thereof hereinafter known collectively as "pro-fragrances". The pro-fragrances of the present invention can exhibit varying release rates depending upon the pro-fragrance chosen. In addition, the pro-fragrances of the present invention can be admixed with the fragrance raw materials which are released therefrom to present the user with an initial fragrance, scent, accord, or bouquet.

The pro-fragrances of the present invention can be suitably admixed with any carrier provided the carrier does not catalyze or in other way promote the pre-mature release form the pro-fragrance of the fragrance raw materials.

The following are non-limiting classes of pro-fragrances according to the present invention.

The esters and polyester pro-fragrances of the present invention are capable of releasing one or more fragrance raw material alcohols. Preferred are esters having the formula:

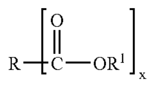

wherein R is substituted or unsubstituted $C_1$–$C_{30}$ alkylene, $C_2$–$C_{30}$ alkenylene, $C_6$–$C_{30}$ arylene, and mixtures thereof; —$OR^1$ is derived from a fragrance raw material alcohol having the formula $HOR^1$, or alternatively, in the case wherein the index x is greater than 1, $R^1$ is hydrogen thereby rendering at least one moiety a carboxylic acid, —$CO_2H$ unit, rather than an ester unit; the index x is 1 or greater. Non-limiting examples of preferred polyester pro-fragrances include digeranyl succinate, dicitronellyl succinate, digeranyl adipate, dicitronellyl adipate, and the like.

The b-ketoesters of the present invention are capable of releasing one or more fragrance raw materials. Preferred b-ketoesters according to the present invention have the formula:

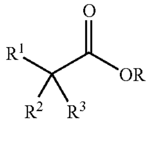

wherein —OR derives from a fragrance raw material alcohol; $R^1$, $R^2$, and $R^3$ are each independently hydrogen, $C_1$–$C_{30}$ alkyl, $C_2$–$C_{30}$ alkenyl, $C_1$–$C_{30}$ cycloalkyl, $C_2$–$C_{30}$ alkynyl, $C_6$–$C_{30}$ aryl, $C_7$–$C_{30}$ alkylenearyl, $C_3$–$C_{30}$ alkyleneoxyalkyl, and mixtures thereof, provided at least one $R^1$, $R^2$, or $R^3$ is a unit having the formula:

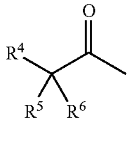

wherein $R^4$, $R^5$, and $R^6$ are each independently hydrogen, $C_1$–$C_{30}$ alkyl, $C_2$–$C_{30}$ alkenyl, $C_1$–$C_{30}$ cycloalkyl, $C_1$–$C_{30}$ alkoxy, $C_6$–$C_{30}$ aryl, $C_7$–$C_{30}$ alkylenearyl, $C_3$–$C_{30}$ alkyleneoxyalkyl, and mixtures thereof, or $R^4$, $R^5$, and $R^6$ can be taken together to form a $C_3$–$C_8$ aromatic or non-aromatic, heterocyclic or non-heterocyclic ring.

Non-limiting examples of b-ketoesters according to the present invention include 2,6-dimethyl-7-octen-2-yl 3-(4-methoxyphenyl)-3-oxo-propionate; 3,7-dimethyl-1,6-octadien-3-yl 3-(nonanyl)-3-oxo-propionate; 9-decen-1-yl 3-(b-naphthyl)-3-oxo-propionate; (a,a-4-trimethyl-3-cyclohexenyl)methyl 3-(b-naphthyl)-3-oxo-propionate; 3,7-dimethyl-1,6-octadien-3-yl 3-(4-methoxyphenyl)-3-oxo-propionate; 2,6-dimethyl-7-octen-2-yl 3-(b-naphthyl)-3-oxo-propionate; 2,6-dimethyl-7-octen-2-yl 3-(4-nitrophenyl)-3-oxo-propionate; 2,6-dimethyl-7-octen-2-yl 3-(4-methoxyphenyl)-3-oxo-propionate; 3,7-dimethyl-1,6-octadien-3-yl 3-(a-naphthyl)-3-oxo-propionate; cis 3-hexen-1-yl 3-(b-naphthyl)-3-oxo-propionate; 2,6-dimethyl-7-octen-2-yl 3-(nonanyl)-3-oxo-propionate; 2,6-dimethyl-7-octen-2-yl 3-oxo-butyrate; 3,7-dimethyl-1,6-octadien-3-yl 3-oxo-butyrate; 2,6-dimethyl-7-octen-2-yl 3-(b-naphthyl)-3-oxo-2-methylpropionate; 3,7-dimethyl-1,6-octadien-3-yl 3-(b-naphthyl)-3-oxo-2,2-dimethylpropionate; 3,7-dimethyl-1,6-octadien-3-yl 3-(b-naphthyl)-3-oxo-2-methylpropionate; 3,7-dimethyl-2,6-octadienyl 3-(b-naphthyl)-3-oxo-propionate; 3,7-dimethyl-2,6-octadienyl 3-heptyl-3-oxo-propionate.

Another class of compound useful as pro-accords according to the present invention are acetals and ketals having the formula:

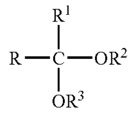

wherein hydrolysis of the acetal or ketal releases one equivalent of aldehyde or ketone and two equivalents of alcohol according to the following scheme:

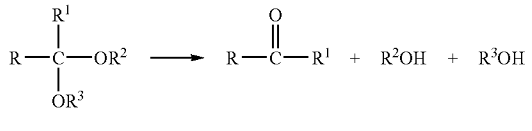

wherein R is $C_1$–$C_{20}$ linear alkyl, $C_4$–$C_{20}$ branched alkyl, $C_6$–$C_{20}$ cyclic alkyl, $C_6$–$C_{20}$ branched cyclic alkyl, $C_6$–$C_{20}$ linear alkenyl, $C_6$–$C_{20}$ branched alkenyl, $C_6$–$C_{20}$ cyclic alkenyl, $C_6$–$C_{20}$ branched cyclic alkenyl, $C_6$–$C_{20}$ substituted or unsubstituted aryl, preferably the moieties which substitute the aryl units are alkyl moieties, and mixtures thereof. $R^1$ is hydrogen, R, or in the case wherein the pro-accord is a ketal, R and $R^1$ can be taken together to form a ring. $R^2$ and $R^3$ are independently selected from the group consisting of $C_5$–$C_{20}$ linear, branched, or substituted alkyl; $C_4$–$C_{20}$ linear, branched, or substituted alkenyl; $C_5$–$C_{20}$ substituted or unsubstituted cyclic alkyl; $C_5$–$C_{20}$ substituted or unsubstituted aryl, $C_2$–$C_{40}$ substituted or unsubstituted alkyleneoxy; $C_3$–$C_{40}$ substituted or unsubstituted alkyleneoxyalkyl; $C_6$–$C_{40}$ substituted or unsubstituted alkylenearyl; $C_6$–$C_{32}$ substituted or unsubstituted aryloxy; $C_6$–$C_{40}$ substituted or unsubstituted alkyleneoxyaryl; $C_6$–$C_{40}$ oxyalkylenearyl; and mixtures thereof.

Non-limiting examples of aldehydes which are releasable by the acetals of the present invention include 4-(4-hydroxy-4-methylpentyl)-3-cyclohexene-1-carboxaldehyde (lyral), phenylacetaldehyde, methylnonyl acetaldehyde, 2-phenylpropan-1-al (hydrotropaldehyde), 3-phenylprop-2-en-1-al (cinnamaldehyde), 3-phenyl-2-pentylprop-2-en-1-al (a-amylcinnamaldehyde), 3-phenyl-2-hexylprop-2-enal (a-hexylcinnamaldehyde), 3-(4-isopropylphenyl)-2-methylpropan-1-al (cyclamen aldehyde), 3-(4-ethylphenyl)-2,2-dimethylpropan-1-al (floralozone), 3-(4-tert-butylphenyl)-2-methylpropanal, 3-(3,4-methylenedioxyphenyl)-2-methylpropan-1-al (helional), 3-(4-ethylphenyl)-2,2-dimethylpropanal, 3-(3-isopropylphenyl)butan-1-al (florhydral), 2,6-dimethylhep-5-en-1-al (melonal), n-decanal, n-undecanal, n-dodecanal, 3,7-dimethyl-2,6-octadien-1-al (citral), 4-methoxybenzaldehyde (anisaldehyde), 3-methoxy-4-hydroxybenzaldehyde (vanillin), 3-ethoxy-4-hydroxybenzaldehyde (ethyl vanillin), 3,4-methylenedioxybenzaldehyde (heliotropin), 3,4-dimethoxybenzaldehyde.

Non-limiting examples of ketones which are releasable by the ketals of the present invention include a-damascone, b-damascone, d-damascone, b-damascenone, muscone, 6,7-dihydro-1,1,2,3,3-pentamethyl-4(5H)-indanone (cashmeran), cis-jasmone, dihydrojasmone, a-ionone, b-ionone, dihydro-b-ionone, g-methyl ionone, a-iso-methyl ionone, 4-(3,4-methylenedioxyphenyl)butan-2-one, 4-(4-hydroxyphenyl)butan-2-one, methyl b-naphthyl ketone, methyl cedryl ketone, 6-acetyl-1,1,2,4,4,7-hexamethyltetralin (tonalid), l-carvone, 5-cyclohexadecen-1-one, acetophenone, decatone, 2-[2-(4-methyl-3-cyclohexenyl-1-yl)propyl]cyclopentan-2-one, 2-sec-butylcyclohexanone, b-dihydro ionone, allyl ionone, a-irone, a-cetone, a-irisone, acetanisole, geranyl acetone, 1-(2-methyl-5-isopropyl-2-cyclohexenyl)-1-propanone, acetyl diisoamylene, methyl cyclocitrone, 4-t-pentyl cyclohexanone, p-t-butylcyclohexanone, o-t-butylcyclohexanone, ethyl amyl ketone, ethyl pentyl ketone, menthone, methyl-7,3-dihydro-2H-1,5-benzodioxepine-3-one, fenchone.

Another class of compound useful as pro-accords according to the present invention are orthoesters having the formula:

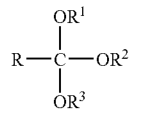

wherein hydrolysis of the orthoester releases one equivalent of an ester and two equivalents of alcohol according to the following scheme:

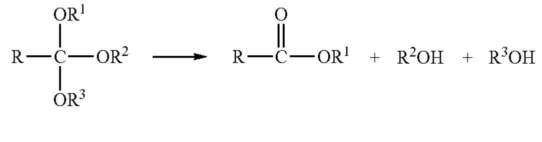

wherein R is hydrogen, $C_1$–$C_{20}$ alkyl, $C_4$–$C_{20}$ cycloalkyl, $C_6$–$C_{20}$ alkenyl, $C_6$–$C_{20}$ aryl, and mixtures thereof; $R^1$, $R^2$ and $R^3$ are each independently selected from the group consisting of $C_5$–$C_{20}$ linear, branched, or substituted alkyl; $C_4$–$C_{20}$ linear, branched, or substituted alkenyl; $C_5$–$C_{20}$ substituted or unsubstituted cyclic alkyl; $C_5$–$C_{20}$ substituted or unsubstituted aryl, $C_2$–$C_{40}$ substituted or unsubstituted alkyleneoxy; $C_3$–$C_{40}$ substituted or unsubstituted alkyleneoxyalkyl; $C_6$–$C_{40}$ substituted or unsubstituted alkylenearyl; $C_6$–$C_{32}$ substituted or unsubstituted aryloxy; $C_6$–$C_{40}$ substituted or unsubstituted alkyleneoxyaryl; $C_6$–$C_{40}$ oxyalkylenearyl; and mixtures thereof.

Non-limiting examples of orthoester pro-fragrances include tris-geranyl orthoformate, tris(cis-3-hexen-1-yl) orthoformate, tris(phenylethyl) orthoformate, bis(citronellyl) ethyl orthoacetate, tris(citronellyl) orthoformate, tris (cis-6-nonenyl) orthoformate, tris(phenoxyethyl) orthoformate, tris(geranyl, neryl) orthoformate (70:30 geranyl: neryl), tris(9-decenyl) orthoformate, tris(3-methyl-5-phenylpentanyl) orthoformate, tris(6-methylheptan-2-yl) orthoformate, tris([4-(2,2,6-trimethyl-2-cyclohexen-1-yl)-3-buten-2-yl]orthoformate, tris[3-methyl-5-(2,2,3-trimethyl-3-cyclopenten-1-yl)-4-penten-2-yl]orthoformate, trismenthyl orthoformate, tris(4-isopropylcyclohexylethyl-2-yl) orthoformate, tris-(6,8-dimethylnonan-2-yl) orthoformate, tris-phenylethyl orthoacetate, tris(cis-3-hexen-1-yl) orthoacetate, tris(cis-6-nonenyl) orthoacetate, tris-citronellyl orthoacetate, bis(geranyl) benzyl orthoacetate, tris(geranyl) orthoacetate, tris(4-isopropylcyclohexylmethyl) orthoacetate, tris(benzyl) orthoacetate, tris(2,6-dimethyl-5-heptenyl) orthoacetate, bis(cis-3-hexen-1-yl) amyl orthoacetate, and neryl citronellyl ethyl orthobutyrate.

Pro-fragrances are suitably described in the following: U.S. Pat. No. 5,378,468 Suffis et al., issued Jan. 3, 1995; U.S. Pat. No. 5,626,852 Suffis et al., issued May 6, 1997; U.S. Pat. No. 5,710,122 Sivik et al., issued Jan. 20, 1998; U.S. Pat. No. 5,716,918 Sivik et al., issued Feb. 10, 1998; U.S. Pat. No. 5,721,202 Waite et al., issued Feb. 24, 1998; U.S. Pat. No. 5,744,435 Hartman et al., issued Apr. 25, 1998; U.S. Pat. No. 5,756,827 Sivik, issued May 26, 1998; U.S. Pat. No. 5,830,835 Severns et al., issued Nov. 3, 1998; U.S. Pat. No. 5,919,752 Morelli et al., issued Jul. 6, 1999; WO 00/02986 published Jan. 20, 2000, Busch et al.; and WO 01/04248 published Jan. 18, 2001, Busch et al. all of which are incorporated herein by reference.

In addition, in the perfume actives that are preferred for use in the compositions and articles of the present invention will have at least about 80%, and more preferably at least about 90%, of the deliverable actives have a "ClogP value" greater than about 1.0. The ClogP value for an active or mixture of actives may be obtained as described above.

2. Perfume Fixative

Optionally, the perfume active or mixture of actives may be combined with a perfume fixative. The perfume fixative materials employed herein are characterized by several criteria that make them especially suitable in the practice of this invention. Dispersible, toxicologically acceptable, non-skin irritating, inert to the perfume, degradable and/or available from renewable resources, and relatively odorless fixatives are used. The use of perfume fixatives is believed to slow the evaporation of more volatile components of the perfume.

Examples of suitable fixatives include members selected from the group consisting of diethyl phthalate, musks, and mixtures thereof. If used, the perfume fixative may comprise from about 10% to about 50%, and preferably from about 20% to about 40%, by weight of the perfume.

3. Perfume Carrier Materials

It is preferable that at least a major part of the perfume be contained or encapsulated in a carrier to prevent premature loss, as well as to avoid a strong product perfume odor. The encapsulation can be in the form of molecular encapsulation, such as inclusion in a complex with cyclodextrin, coacevate microencapsulation wherein the perfume droplet is enclosed in a solid wall material, and "cellular matrix" encapsulation wherein solid particles containing perfume droplets are stably held in cells. In addition, perfumes and other organic fabric care actives can be absorbed onto the surface or adsorbed into the pores of porous carrier materials or embedded in a matrix, such as a starch or sugar matrix. As used herein, "porous carrier materials" includes porous solids selected from the group consisting of amorphous silicates, crystalline non-layer silicates, layered silicates, calcium carbonates, calcium/sodium carbonate double salts, sodium carbonates, clays, zeolites, sodalites, alkali metal phosphates, macroporous zeolites, chitin microbeads, carboxyalkylcelluloses, carboxyalkylstarches, foams, porous starches, chemically modified starches, and mixtures thereof.

The encapsulated perfume active useful in the present invention is preferably released by a moisture activation mechanism. Moisture-activated microcapsules release perfume upon being contacted with liquid water or humidity.

The selection of the most suitable method of perfume delivery takes into account the effectiveness, the efficiency, and the cost of each method. Cyclodextrin/perfume complex is preferred for its effectiveness and ease of processing. The complex protects and retains the perfume ingredients from physical effects (e.g., no rupture/perfume loss during processing, packaging, shipping, and storing of the product, or perfume loss from diffusion) and from chemical effects (e.g., degradation during storage). However, the perfume loading in the cyclodextrin complex is fairly low, e.g., from about 10% to about 18% in beta-cyclodextrin/perfume complex.

Perfume microcapsules, e.g., coacevate microcapsule where the perfume droplet is enclosed in a solid wall material or "cellular" microcapsule where a solid particle contains perfume droplets stably held in the cells, are preferred for their perfume loading which can be as high as 60–80%. However, the encapsulation process is more demanding, and perfume leakage due to breakage of the microcapsules during processing, packaging, shipping, and storing of the product tends to occur. There is a need to balance the rigidity of the microcapsule to avoid undesirable and untimely breakage and the desired frangibility to release perfume by pressure.

Porous particles can also be used to retain perfume and release it slowly in use. The crude matrix particles where the perfume is embedded in a matrix, such as a starch or sugar matrix are inexpensive and easy to produce. The perfume loading is medium. However, the activation to release perfume can be less effective than the encapsulation methods described herein above.

Preferred perfume carrier materials are cyclodextrins that may be used to form cyclodextrin/perfume inclusion complexes. Different forms and sources of cyclodextrins useful for complexing with perfumes are described in detail below in conjunction with the description of their use as malodor control agents.

Other preferred perfume carrier materials are zeolite X, zeolite Y and mixtures thereof. The term zeolite as used herein refers to a crystalline aluminosilicate material. The structural formula of a zeolite is based on the crystal unit cell, the smallest unit of structure represented by $$Mm/n[AlO_2)m(SiO_2)y]xH_2O$$

where n is the valence of the cation M, x is the number of water molecules per unit cell, m and y are the total number of tetrahedra per unit cell, and y/m is 1 to 100. Most preferably, y/m is 1 to 5. The cation M can be Group IA and Group IIA elements, such as sodium, potassium, magnesium and calcium.

The aluminosilicate zeolite materials useful in the practice of this invention are commercially available. The preferred zeolite is a faujasite-type zeolite including Type X Zeolite or Type Y Zeolite, both with nominal pore size of about 8 Angstrom units, typically in the range of 7.4 to 10 Angstrom units. Methods for producing X and Y-type zeolites are well known and available in standard texts.

For purposes of illustration and not by way of limitation, in a preferred embodiment, the crystalline aluminosilicate material is Type X and is selected from the following:

(I) $Na_{86}[AlO_2]_{86}\cdot(SiO_2)_{106}\cdot xH_2O$, (II) $K_{86}[AlO_2]_{86}\cdot(SiO_2)_{106}\cdot xH_2O$, (III) $Ca_{40}Na_6[AlO_2]_{86}\cdot(SiO_2)_{106}\cdot xH_2O$, (IV) $Sr_{21}Ba_{22}[AlO_2]_{86}\cdot(SiO_2)_{106}\cdot xH_2O$, and mixtures thereof, wherein x is from about 0 to about 276. Zeolites of Formula I and II have a nominal pore size or opening of 8.4 Angstrom units. Zeolites of Formulas III and IV have a nominal pore size or opening of 8.0 Angstrom units.

In another preferred embodiment, the crystalline aluminosilicate materials is Type Y and is selected from the following:

(V) $Na_{56}[AlO_2\}_{56}\cdot SiO_2)_{136}\cdot xH_2O$ (VI) $K_{56}[AlO_2]_{56}\cdot(SiO_2)_{136}\cdot xH_2O$ and mixtures thereof, wherein x is from about 0 to about 276. Zeolites of Formulas V and VI have a nominal pore size or opening of 8.0 Angstrom units.

Zeolites used in the present invention are in particle form having an average particle size from about 0.5 microns to about 120 microns, preferably from about 0.5 microns to about 30 microns, as measured by standard particle size analysis technique. Zeolites carrying perfume or other fabric care actives tend to agglomerate which facilitates the formation of an article and its dissolution when the active is displaced from the zeolite in solution. The size of the zeolite particles allows them to be entrained in the fabrics with which they come in contact. Once established on the fabric surface the zeolites can begin to release their incorporated fabric care actives, especially when subjected to warm and/or humid conditions.

Where zeolite is the preferred perfume carrier material, improved retention of the perfume with the zeolite may be achieved by selecting perfume raw materials or mixtures thereof in accordance with the methods described in U.S. Pat. No. 5,955,419, Barket, Jr., et al., issued Sep. 21, 1999, which is incorporated herein by reference. As described therein, it is important to identify and define several characteristic parameters of perfume molecules, namely, their longest and widest dimension, cross sectional area, molecular volume and molecular surface area. These values are calculated for individual perfume molecules using the CHEMX program (from Chemical Design, Ltd.) for molecules in a minimum energy conformation as determined by the standard geometry optimized in CHEMX and using standard atomic van der Waal radii.

Definitions of the parameters are as follows:

"Longest": the greatest distance (in Angstroms) between atoms in a molecule augmented by their van der Waals radii.

"Widest": the greatest distance (in Angstroms) between atoms in a molecule augmented by their van der Waals radii in the projection of the molecule on a plane perpendicular to the "longest" axis of the molecule.

"Cross Sectional Area": area (in square Angstrom units) filled by the projection of the molecule in the plane perpendicular to the longest axis.

"Molecular Volume": the volume (in cubic Angstrom units) filled by the molecule in it energy configuration.

"Molecular Surface Area": arbitrary units that scale as square Angstroms (for calibration purposes, the molecules methyl beta naphthyl ketone, benzyl salicylate, and camphor gum have surface areas measuring 128+/−3, 163.5+/−3 and 122.5+/−3 units respectively).

The shape of the molecule may also be important for its incorporation in a carrier. For example, a symmetric perfectly spherical molecule that is small enough to be included into the zeolite channels has no preferred orientation and is incorporated from any approach direction. However, for molecules that have a length that exceeds the pore dimension, there is a preferred "approach orientation" for inclusion. Calculation of a molecule's volume/surface area ratio is used herein to express the "shape index" for a molecule. The higher the value, the more spherical the molecule.

For purposes of the present invention, perfume actives are classified according to their ability to be incorporated into zeolite pores, and hence their utility as components for delivery from a zeolite carrier through an aqueous environment. Plotting these agents in a volume/surface area ratio vs. cross sectional area plane permits convenient classification of the agents in groups according to their incorporability into zeolite or some other carrier. In particular, for the zeolite X and Y carriers, perfume actives are incorporated if they fall below the line (herein referred to as the "incorporation line") defined by the equation:

$$y=0.01068X+1.497$$

where x is cross sectional area and y is volume/surface area ratio. Agents that fall below the incorporation line are referred to herein as "deliverable agents" while those above the line are referred to herein as "non-deliverable agents."

For containment through the wash, deliverable agents are retained in the zeolite carrier as a function of their affinity for the carrier relative to competing deliverable agents. Affinity is impacted by the molecule's size, hydrophobicity, functionality, volatility, etc., and can be affected via interaction between deliverable agents within the zeolite carrier. These interactions permit improved through the wash containment for the deliverable agents. Specifically, for the present invention, the use of deliverable agents having at least one dimension that is closely matched to the zeolite carrier pore dimension slows the loss of other deliverable agents in the aqueous wash environment. Deliverable agents that function in this manner are referred to herein as "blocker agents", and are defined herein in the volume/surface area ratio vs. cross sectional area plane as those deliverable agent molecules falling below the "incorporation line" but above the line (herein referred to as the "blocker line") defined by the equation:

$$y=0.01325X+1.46$$

where x is cross sectional area and y is volume/surface area ratio.

For the present invention, fabric care actives that utilize zeolite X and/or Y as carriers, are deliverable agents below the "incorporation line" that can be delivered and released from the compositions and articles of the present invention, the preferred materials being those that fall below the "blocker line". Also preferred are mixtures of blocker agents and other deliverable agents. Laundry perfume actives useful for the present invention preferably comprise from about 5% to about 100% (preferably from about 25% to about 100% and more preferably from about 50% to about 100%) deliverable agents, and preferably comprising from about 0.1% to about 100% (preferably 0.1% to about 50%) blocker agents, by weight of the laundry perfume active or mixture of actives.

Also preferred are perfumes carried through the laundry process and thereafter released into the air around the dried fabrics (e.g. such as the space around the fabric during storage). This requires movement of the perfume out of the zeolite pores with subsequent partitioning into the air around the fabric. Preferred perfume agents are therefore further identified on the basis of their volatility. Boiling point is used herein as a measure of volatility and preferred materials have a boiling point less than about 300° C. Perfume actives and mixtures of actives useful for the present invention preferably comprise at least about 50% of deliverable actives with boiling points less than about 300° C. (preferably at least about 60%; more preferably at least about 70% of such actives).

4. Incorporation of Perfume Active in Carrier Material a) Cyclodextrin/Active Inclusion Complexes The cyclodextrin/perfume inclusion complexes useful herein are formed in any of the ways known in the art. Typically, the complexes are formed either by bringing the perfume and the cyclodextrin together in a suitable solvent, e.g., water, or, preferably, by kneading/slurrying the ingredients together in the presence of a suitable, preferably minimal, amount of solvent, preferably water. The kneading/slurrying method is particularly desirable because it produces smaller complex particles and requires the use of less solvent, eliminating or reducing the need to further reduce particle size and separate excess solvent. Disclosures of complex formation can be found in Atwood, J. L., J. E. D. Davies & D. D. MacNichol, (Ed.): *Inclusion Compounds, Vol. III*, Academic Press (1984), especially Chapter 11, Atwood, J. L. and J. E. D. Davies (Ed.): *Proceedings of the Second International Symoosium of Cyclodextrins* Tokyo, Japan, (July, 1984), and J. Szejtli, *Cyclodextrin Technology*, Kluwer Academic Publishers (1988).

In general, perfume/cyclodextrin complexes have a molar ratio of perfume compound to cyclodextrin of about 1:1. However, the molar ratio can be either higher or lower, depending on the size of the perfume compound and the identity of the cyclodextrin compound. The molar ratio can be determined by forming a saturated solution of the cyclodextrin and adding the perfume to form the complex. In general the complex will precipitate readily. If not, the complex can usually be precipitated by the addition of electrolyte, change of pH, cooling, etc. The complex can then be analyzed to determine the ratio of perfume to cyclodextrin.

The actual complexes are determined by the size of the cavity in the cyclodextrin and the size of the perfume molecule. Desirable complexes can be formed using mixtures of cyclodextrins since perfumes are normally mixtures of materials that vary widely in size. It is usually desirable that at least a majority of the material be alpha-, beta-, and/or gamma-cyclodextrin, more preferably beta-cyclodextrin.

The content of the perfume in the beta-cyclodextrin complex is typically from about 5% to about 15%, more normally from about 7% to about 12%.

Continuous complexing operation usually involves the use of supersaturated solutions, kneading/slurrying method, and/or temperature manipulation, e.g., heating and then either cooling, freeze-drying, etc. The complexes are dried to a dry powder to make the desired composition. In general, the fewest possible process steps are preferred to avoid loss of perfume.

Complexes having a particle size of less than about 12 microns, preferably less than about 10 microns, more preferably less than about 8 microns, and even more preferably less than about 5 microns, improve the release, especially the speed of release of the perfume when the complexes are wetted. The particle size is typically between about 0.001 and 10 microns, preferably between about 0.05 and 5 microns. It is highly desirable that at least an effective amount of the perfume be in complexes having the such particle sizes. It is desirable that at least about 75%, preferably at least about 80%, more preferably at least about 90%, and even more preferably at least about 100%, of the complex that is present have the such particle sizes.

These small particles are conveniently prepared by kneading methods and/or grinding techniques. Cyclodextrin complexes with large particle sizes can be pulverized to obtain the desired smaller particles of less than about 12 microns by using, e.g., a fluid energy mill. Some caution should be observed in that some of the dry complex particles may remain agglomerated, and the aggregates can be easily broken by mechanical action.

b) Moisture-Activated Cellular Perfume Microcapsules

Water-soluble cellular matrix perfume microcapsules are solid particles containing perfume stably held in the cells. The water-soluble matrix material comprises mainly polysaccharide and polyhydroxy compounds. The polysaccharides are preferably higher polysaccharides of the non-sweet, colloidally-soluble types, such as natural gums, e.g., gum arabic, starch derivatives, dextrinized and hydrolyzed starches, and the like. The polyhydroxy compounds are preferably alcohols, plant-type sugars, lactones, monoethers, and acetals. The cellular matrix microcapsules useful in the present invention are prepared by, e.g., (1) forming an aqueous phase of the polysaccharide and polyhydroxy compound in proper proportions, with added emulsifier if necessary or desirable; (2) emulsifying the perfumes in the aqueous phase; and (3) removing moisture while the mass is plastic or flowable, e.g., by spray drying droplets of the emulsion. The matrix materials and process details are disclosed in, e.g., U.S. Pat. No. 3,971,852, Brenner et al., issued Jul. 27, 1976, which is incorporated herein by reference.

Moisture-activated perfume microcapsules of the cellular type can be obtained commercially, e.g., as IN-CAP® from Polak's Frutal Works, Inc., Middletown, N.Y.; and as Optilok System® encapsulated perfumes from Encapsulated Technology, Inc., Nyack, N.Y.

Water-soluble cellular matrix perfume microcapsules preferably have size of from about 0.5 micron to about 300 microns, more preferably from about 1 micron to about 200 microns, most preferably from about 2 microns to about 100 microns.

Sufficient amount of moisture-activated perfume microcapsules should be used to deliver the desired levels of perfume, depending on the perfume loading of the microcapsules.

Cruder starch matrix perfume particles can be prepared according to the disclosure in U.S. Pat. No. 5,267,531. The perfume oil is emulsified with various starches and water for a period of two hours. The emulsion is then spray dried and checked for proper oil content.

c) Incorporation of Perfume in Zeolites

The Type X or Type Y zeolites to be used herein preferably contain less than about 10% desorbable water, more preferably less than about 8% desorbable water and most preferably less than about 5% desorbable water. Such materials may be obtained by first activating/dehydrating by heating to about 150 to about 350° C., optionally with reduced pressure (from about 0.001 to about 20 Torr) for at least 12 hours. After activation, the perfume active or mixture of actives is slowly and thoroughly mixed with the activated zeolite and, optionally, heated to about 60° C. for up to two hours to accelerate absorption equilibrium within the zeolite particles. The perfume zeolite mixture is then cooled to room temperature at which time the mixture is in the form of a free flowing powder.

It is often desirable to mix the zeolite containing a perfume into a fluidizing agent to convert the mixture into a slurry. For example, this would facilitate the filling of a gelatin capsule or a polyvinyl alcohol film bead or pouch to provide a convenient unitized dose. Liquid silicones are good fluidizing agents since they have low or no moisture content and they do not act to extract the perfume from the zeolite carrier even when stored at higher temperatures (e.g. 37° C.). A preferred fluidizing agent for use in combination with perfume-zeolite complexes is decamethylcyclopentane siloxane (D5) sold by Dow Corning as DC 245.

The amount of fabric care active incorporated into the zeolite carrier is less than about 20%, typically less than about 18.5% and more typically less than about 15% by weight of the loaded particles, given the limits on the pore volume of the zeolite. It is to be recognized, that although the perfume/zeolite particles may exceed this level of actives by weight of the particle the excess levels of fabric care active will not be incorporated into the zeolite, even if only deliverable agents are used. Therefore, the perfume/zeolite particles may comprise more than 20% by weight of fabric care actives. Since any excess actives (as well as non-deliverable actives that are present) are not incorporated into the zeolite pores, these materials are likely to be immediately released to the wash or rinse solution upon contact with the aqueous medium. This can be desirable to give an immediate release of the fabric care active to the laundry solution. In the case of perfume articles, the excess perfume provides an immediate "bloom" of the fragrance upon dispensing.

Another preferred optional ingredient is free perfume, which is perfume that is not present as a perfume/zeolite complex or some other perfume/carrier complex. The presence of free perfume is also very useful for imparting odor benefits. Preferably, free perfume contains at least about 1%, more preferably at least about 10% by weight of substantive perfume materials. Such free perfume is preferably present at a level of from about 0.10% to about 10% by weight of the portion of the composition that is transferred to the fabrics.

Although the description of zeolites and cyclodextrins is provided herein with respect to their use as a carrier for perfume actives, it is to be noted that zeolites, cyclodextrins and other carrier materials may be used in the present invention to complex with non-perfume fabric care actives or mixtures of actives as well, and that the forgoing description is equally applicable to such non-perfume fabric care actives.

B. Bodying Agents, Form and Drape Control Agents, & Smoothness Agents

The composition may contain an effective amount of a fabric wrinkle control agent that will provide body, form and drape control or smoothness to the treated fabrics. Preferably, these agents will be selected from the group consisting of fiber lubricants, shape retention polymers, hydrophilic plasticizers, lithium salts, and mixtures thereof.

1. Fiber Lubricants

The present invention may utilize a fiber lubricant to impart a lubricating property or increased gliding ability to fibers in fabric, particularly clothing. Not to be bound by theory, it is believed that water and other alcoholic solvents break or weaken the hydrogen bonds that hold the wrinkles, thus the fabric lubricant facilitates the fibers to glide on one another to further release the fibers from the wrinkle condition in wet or damp fabric. After the fabric is dried, a residual silicone, for example can provide lubricity to reduce the tendency of fabric re-wrinkling.

a) Silicone Polymers

The present invention may utilize silicone to impart a lubricating property or increased gliding ability to fibers in fabric, particularly clothing. The silicone useful in providing fiber lubricity in the composition of the present invention should have pendant alkyl groups having less than about 8, preferably less than about 6, carbon atoms, and no pendant aryl groups. Nonlimiting examples of useful silicones include noncurable silicones such as polydimethylsilicone and volatile silicones, and curable silicones such as aminosilicones and hydroxysilicones. When the composition of this invention is to be dispensed from a spray dispenser, the noncurable silicones such as polydimethylsilicone, especially the volatile silicones, are preferred. Curable and/or reactive silicones such as amino-functional silicones silicones and silicones with reactive groups such as Si—OH, Si—H, silanes, and the like, are preferably dispensed to a laundry solution by some other dispensing means. Many types of aminofunctional silicones also cause fabric yellowing and such silicones are not preferred.

The word "silicone" as used herein preferably refers to emulsified and/or microemulsified silicones, including those that are commercially available and those that are emulsified and/or microemulsified in the composition, unless otherwise described. Some non-limiting examples of silicones which are useful in the present invention are: non-volatile silicone fluids such as polydimethyl siloxane gums and fluids; volatile silicone fluid which can be a cyclic silicone fluid of the formula $[(CH_3)_2\ SiO]_n$ where n ranges between about 3 to about 7, preferably about 5, or a linear silicone polymer fluid having the formula $(CH_3)_3\ SiO[(CH_3)_2\ SiO]_m\ Si(CH_3)_3$ where m can be 0 or greater and has an average value such that the viscosity at 25° C. of the silicone fluid is preferably about 5 centistokes or less.

Thus one type of silicone that is useful in the composition of the present invention is polyalkyl silicone with the following structure:

$$A\text{-}(Si(R_2)—O—[Si(R_2)—O—]_q—Si(R_2)\text{-}A$$

The alkyl groups substituted on the siloxane chain (R) or at the ends of the siloxane chains (A) can have any structure as long as the resulting silicones remain fluid at room temperature.

Each R group preferably is alkyl, hydroxy, or hydroxyalkyl group, and mixtures thereof, having less than about 8, preferably less than about 6 carbon atoms, more preferably, each R group is methyl, ethyl, propyl, hydroxy group, and mixtures thereof. Most preferably, each R group is methyl. Aryl, alkylaryl and/or arylalkyl groups are not preferred. Each A group which blocks the ends of the silicone chain is hydrogen, methyl, methoxy, ethoxy, hydroxy, propoxy, and mixtures thereof, preferably methyl. q is preferably an integer from about 7 to about 8,000.

The preferred silicones are polydimethyl siloxanes and preferably those polydimethyl siloxanes having a viscosity of from about 10 to about 1000,000 centistokes at 25° C. Mixtures of volatile silicones and non-volatile polydimethyl siloxanes are also preferred. Preferably, the silicones are hydrophobic, non-irritating, non-toxic, and not otherwise harmful when applied to fabric or when they come in contact with human skin. Further, the silicones are compatible with other components of the composition are chemically stable under normal use and storage conditions and are capable of being deposited on fabric.

Suitable methods for preparing these silicone materials are described in U.S. Pat. Nos. 2,826,551 and 3,964,500. Silicones useful in the present invention are also commercially available. Suitable examples include silicones offered by Dow Corning Corporation and General Electric Company.

Other useful silicone materials, but less preferred than polydimethyl polysiloxane, include materials of the formula:

$$HO—[Si(CH_3)_2—O]_x—\{Si(OH)[(CH_2)_3—NH—(CH_2)_2—NH_2]O\}_y—H$$

wherein x and y are integers which depend on the molecular weight of the silicone, preferably having a viscosity of from about 10,000 cst to about 500,000 cst at 25° C. This material is also known as "amodimethicone". Although silicones with a high number, e.g., greater than about 0.5 millimolar equivalent of amine groups can be used, they are not preferred because they can cause fabric yellowing.

Similarly, silicone materials which can be used correspond to the formulas:

$$(R^1)_aG_{3\text{-}a}\text{-}Si—(—OSiG_2)_n\text{-}(OSiG_b(R^1)_{2\text{-}b})_m—O—SiG_{3\text{-}a}(R^1)_a$$

wherein G is selected from the group consisting of hydrogen, OH, and/or $C_1$–$C_5$ alkyl; a denotes 0 or an integer from 1 to 3; b denotes 0 or 1; the sum of n+m is a number from 1 to about 2,000; $R^1$ is a monovalent radical of formula $CpH_{2p}$ L in which p is an integer from 2 to 4 and L is selected from the group consisting of:

$—N(R^2)CH_2—CH_2—N(R^2)_2$;

$—N(R^2)_2$;

$—N+(R^2)_3A^-$; and $—N+(R^2)CH_2—CH_2N+H_2A^-$ wherein each $R^2$ is chosen from the group consisting of hydrogen, a $C_1$–$C_5$ saturated hydrocarbon radical, and each $A^-$ denotes compatible anion, e.g., a halide ion; and $$R^3—N+(CH_3)_2\text{-}Z\text{-}[Si(CH_3)_2O]_f—Si(CH_3)_2\text{-}Z\text{-}N+(CH_3)_2—R^3.2CH_3COO^-$$

wherein $z=—CH_2—CH(OH)—CH_2O—CH_2)_2—$ $R^3$ denotes a long chain alkyl group; and f denotes an integer of at least about 2.

In the formulas herein, each definition is applied individually and averages are included.

Another silicone material which can be used, but is less preferred than polydimethyl siloxanes, has the formula:

$$(CH_3)_3—Si—[OSi(CH_3)_2]_n—\{—O—Si(CH_3)[(CH_2)_3—NH—(CH_2)_2—NH_2]\}_m OSi(CH_3)_3$$

wherein n and m are the same as before. The preferred silicones of this type are those which do not cause fabric discoloration.

Alternatively, the silicone material can be provided as a moiety or a part of a non-silicone molecule. Examples of such materials are copolymers containing silicone moieties, typically present as block and/or graft copolymers.

When silicone is present, it is present at least an effective amount to provide lubrication of the fibers.

b) Synthetic Solid Particles

Solid polymeric particles of average particle size smaller than about 10 microns, preferably smaller than 5 microns, more preferably smaller than about 1 micron, may be used as a lubricant, since they can provide a "roller-bearing" action. Polyethylene emulsions and suspensions are also suitable for providing this lubrication or smoothness effect to the fabrics on which they are deposited. Suitable smoothing agents are available under the tradename VELUSTROL from HOECHST Aktiengesellschaft of Frankfurt am Main, Germany. In particular, the polyethylene emulsions sold under the tradename VELUSTROL PKS, VELUSTROL KPA, or VELUSTROL P-40 may be employed in the compositions of the present invention. The use of such polymers in fabric softening compositions is described in U.S. Pat. Nos. 5,830,843, 2. Shape Retention Polymers Shape retention may be imparted to fabrics through the use of polymers that act by forming a film and/or by providing adhesive properties to the fabrics. These polymers may be natural, or synthetic. By "adhesive" it is meant that when applied as a solution or a dispersion, the polymer can attach to the surface of the fabric fibers and dry in place. The polymer can form a film on the fiber surfaces, or when residing between two fibers and in contact with the two fibers, it can bond the two fibers together. Other polymers such as starches can form a film and/or bond the fibers together when the treated fabric is pressed by a hot iron. Such a film will have adhesive strength, cohesive breaking strength, and cohesive breaking strain.

Nonlimiting examples of natural shape retention polymers are starches and their derivatives, and chitins and their derivatives. Starch is not normally preferred, since it makes the fabric resistant to deformation. However, it does provide increased "body" which is often desired. Starch is particularly preferred however, when the consumer intends to iron the fabrics after they have been washed and dried. When used, starch may be used as a solid or solubilized or dispersed to be combined with other materials in the composition. Any type of starch, e.g. those derived from corn, wheat, rice, grain sorghum, waxy grain sorghum, waxy maize or tapioca, or mixtures thereof and water soluble or dispersible modifications or derivatives thereof, can be used in the compositions of the present invention. Modified starches may include natural starches that have been degraded to obtain a lower viscosity by acidic, oxidative or enzymic depolymerization. Additionally, low viscosity commercially available propoxylated and/or ethoxylated starches are useable in the present composition and are preferred when the composition is to be dispensed with a sprayer because of their low viscosity at relatively high solid concentrations. Suitable alkoxylated, low viscosity starches are submicron-size particles of hydrophobic starch that are readily dispersed in water and are prepared by alkoxylation of granular starch with a monofunctional alkoxylating agent which provides the starch with ether linked hydrophilic groups. A suitable method for their preparation is taught in U.S. Pat. No. 3,462,283.

The synthetic polymers useful in the present invention are comprised of monomers. Nonlimiting examples of monomers which can be used to form the synthetic polymers useful in the present invention include: low molecular weight $C_1$–$C_6$ unsaturated organic mono- and polycarboxylic acids, such as acrylic acid, methacrylic acid, crotonic acid, maleic acid and its half esters, itaconic acid, and mixtures thereof; esters of said acids with $C_1$–$C_6$ alcohols, such as methanol, ethanol, 1-propanol, 2-propanol, 1-butanol, 2-methyl-1-propanol, 1-pentanol, 2-pentanol, 3-pentanol, 2-methyl-1-butanol, 1-methyl-1-butanol, 3-methyl-1-butanol, 1-methyl-1-pentanol, 2-methyl-1-pentanol, 3-methyl-1-pentanol, t-butanol, cyclohexanol, 2-ethyl-1-butanol, and the like, and mixtures thereof. Nonlimiting examples of said esters are methyl acrylate, ethyl acrylate, t-butyl acrylate, methyl methacrylate, hydroxyethyl methacrylate, methoxy ethyl methacrylate, and mixtures thereof; amides and imides of said acids, such as N,N-dimethylacrylamide, N-t-butyl acrylamide, maleimides; low molecular weight unsaturated alcohols such as vinyl alcohol (produced by the hydrolysis of vinyl acetate after polymerization), alkyl alcohol; esters of said alcohols with low molecular weight carboxylic acids, such as, vinyl acetate, vinyl propionate; ethers of said alcohols such as methyl vinyl ether; polar vinyl heterocyclics, such as vinyl pyrrolidone, vinyl caprolactam, vinyl pyridine, vinyl imidazole, and mixtures thereof; other unsaturated amines and amides, such as vinyl amine, diethylene triamine, dimethylaminoethyl methacrylate, ethenyl formamide; vinyl sulfonate; salts of acids and amines listed above; low molecular weight unsaturated hydrocarbons and derivatives such as ethylene, propylene, butadiene, cyclohexadiene, vinyl chloride; vinylidene chloride; and mixtures thereof and alkyl quaternized derivatives thereof, and mixtures thereof.

Preferably, said monomers are selected from the group consisting of vinyl alcohol; acrylic acid; methacrylic acid; methyl acrylate; ethyl acrylate; methyl methacrylate; t-butyl acrylate; t-butyl methacrylate; n-butyl acrylate; n-butyl methacrylate; dimethylaminoethyl methacrylate; N,N-dimethyl acrylamide; N,N-dimethyl methacrylamide; N-t-butyl acrylamide; vinylpyrrolidone; vinyl pyridine; adipic acid; diethylenetriamine; salts thereof and alkyl quaternized derivatives thereof, and mixtures thereof. Preferably, said monomers form homopolymers and/or copolymers (i.e., the film-forming and/or adhesive polymer) having a glass transition temperature (Tg) of from about −20° C. to about 150° C., preferably from about −10° C. to about 150° C., more preferably from about 0° C. to about 100° C. Most preferably, the adhesive polymer when dried to form a film will have a Tg of at least about 25° C., so that they are not unduly sticky or "tacky" to the touch.

Preferably the shape retention polymer is soluble and/or dispersible in water and/or alcohol. Said polymer typically has a molecular weight of at least about 500, preferably from about 1,000 to about 2,000,000, more preferably from about 5,000 to about 1,000,000, and even more preferably from about 30,000 to about 300,000 for some polymers.

Some non-limiting examples of homopolymers and copolymers which are useful as film-forming and/or adhesive polymers in the present invention are: adipic acid/dimethylaminohydroxypropyl diethylenetriamine copolymer; adipic acid/epoxypropyl diethylenetriamine copolymer; poly(vinylpyrrolidone/dimethylaminoethyl methacrylate); polyvinyl alcohol; polyvinylpyridine n-oxide; methacryloyl ethyl betaine/methacrylates copolymer; ethyl acrylate/methyl methacrylate/methacrylic acid/acrylic acid copolymer; polyamine resins; and polyquaternary amine resins; poly(ethenylformamide); poly(vinylamine) hydrochloride; poly(vinyl alcohol-co-6% vinylamine); poly (vinyl alcohol-co-12% vinylamine); poly(vinyl alcohol-co-6% vinylamine hydrochloride); and poly(vinyl alcohol-co-12% vinylamine hydrochloride). Preferably, said copolymer and/or homopolymers are selected from the group consisting of adipic acid/dimethylaminohydroxypropyl diethylenetriamine copolymer; poly(vinylpyrrolidone/dimethylaminoethyl methacrylate); polyvinyl alcohol; ethyl acrylate/methyl methacrylate/methacrylic acid/acrylic acid copolymer; methacryloyl ethyl betaine/methacrylates copolymer; polyquaternary amine resins; poly(ethenylformamide); poly (vinylamine) hydrochloride; poly(vinyl alcohol-co-6% vinylamine); poly(vinyl alcohol-co-12% vinylamine); poly (vinyl alcohol-co-6% vinylamine hydrochloride); and poly (vinyl alcohol-co-12% vinylamine hydrochloride).

Nonlimiting examples of preferred polymers that are commercially available are polyvinylpyrrolidone/dimethylaminoethyl methacrylate copolymer, such as Copolymer 958, molecular weight of about 100,000 and Copolymer 937, molecular weight of about 1,000,000, available from GAF Chemicals Corporation; adipic acid/dimethylaminohydroxypropyl diethylenetriamine copolymer, such as Cartaretin F-4® and F-23, available from Sandoz Chemicals Corporation; methacryloyl ethyl betaine/methacrylates copolymer, such as Diaformer Z-SM®, available from Mitsubishi Chemicals Corporation; polyvinyl alcohol copolymer resin, such as Vinex 2019®, available from Air Products and Chemicals or Moweol®, available from Clariant; adipic acid/epoxypropyl diethylenetriamine copolymer, such as Delsette 101®, available from Hercules Incorporated; polyamine resins, such as Cypro 515®, available from Cytec Industries; polyquaternary amine resins, such as Kymene 557H®, available from Hercules Incorporated; and polyvinylpyrrolidone/acrylic acid, such as Sokalan EG 310®, available from BASF.

The preferred polymers that are useful in the present invention are selected from the group consisting of copolymers of hydrophilic monomers and hydrophobic monomers. The polymer can be linear random or block copolymers, and mixtures thereof. Such hydrophobic/hydrophilic copolymers typically have a hydrophobic monomer/hydrophilic monomer ratio of from about 95:5 to about 20:80, preferably from about 90:10 to about 40:60, more preferably from about 80:20 to about 50:50 by weight of the copolymer. The hydrophobic monomer can comprise a single hydrophobic monomer or a mixture of hydrophobic monomers, and the hydrophilic monomer can comprise a single hydrophilic monomer or a mixture of hydrophilic monomers. The term "hydrophobic" is used herein consistent with its standard meaning of lacking affinity for water, whereas "hydrophilic" is used herein consistent with its standard meaning of having affinity for water. As used herein in relation to monomer units and polymeric materials, including the copolymers, "hydrophobic" means substantially water insoluble; "hydrophilic" means substantially water soluble. In this regard, "substantially water insoluble" shall refer to a material that is not soluble in distilled (or equivalent) water, at 25° C., at a concentration of about 0.2% by weight, and preferably not soluble at about 0.1% by weight (calculated on a water plus monomer or polymer weight basis). "Substantially water soluble" refers to a material that is soluble in distilled (or equivalent) water, at 25° C., at a concentration of about 0.2% by weight, and is preferably soluble at about 1% by weight. The terms "soluble", "solubility" and the like, for purposes hereof, corresponds to the maximum concentration of monomer or polymer, as applicable, that can dissolve in water or other solvents to form a homogeneous solution, as is well understood to those skilled in the art.

Nonlimiting examples of useful hydrophobic monomers are acrylic acid $C_1$–$C_6$ alkyl esters, such as methyl acrylate, ethyl acrylate, t-butyl acrylate; methacrylic $C_1$–$C_6$ alkyl esters, such as methyl methacrylate, methoxy ethyl methacrylate; vinyl alcohol esters of carboxylic acids, such as, vinyl acetate, vinyl propionate, vinyl ethers, such as methyl vinyl ether; vinyl chloride; vinylidene chloride; ethylene, propylene and other unsaturated hydrocarbons; and the like; and mixtures thereof. Some preferred hydrophobic monomers are methyl acrylate, methyl methacrylate, t-butyl acrylate, t-butyl methacrylate, n-butyl acrylate, n-butyl methacrylate, and mixtures thereof.

Nonlimiting examples of useful hydrophilic monomers are unsaturated organic mono- and polycarboxylic acids, such as acrylic acid, methacrylic acid, crotonic acid, maleic acid and its half esters, itaconic acid; unsaturated alcohols, such as vinyl alcohol, allyl alcohol; polar vinyl heterocyclics, such as vinyl pyrrolidone, vinyl caprolactam, vinyl pyridine, vinyl imidazole; vinyl amine; vinyl sulfonate; unsaturated amides, such as acrylamides, e.g., N,N-dimethylacrylamide, N-t-butyl acrylamide; hydroxyethyl methacrylate; dimethylaminoethyl methacrylate; salts of acids and amines listed above; and the like; and mixtures thereof. Some preferred hydrophilic monomers are acrylic acid, methacrylic acid, N,N-dimethyl acrylamide, N,N-dimethyl methacrylamide, N-t-butyl acrylamide, dimethylamino ethyl methacrylate, vinyl pyrrolidone, salts thereof and alkyl quaternized derivatives thereof, and mixtures thereof.

Non limiting examples of polymers for use in the present invention include the following, where the composition of the copolymer is given as approximate weight percentage of each monomer used in the polymerization reaction used to prepare the polymer: vinyl pyrrolidone/vinyl acetate copolymers (at ratios of up to about 30% by weight of vinyl pyrrolidone); vinyl pyrrolidone/vinyl acetate/butyl acrylate copolymer (10/78/12 and 10/70/20); vinyl pyrrolidone/vinyl propionate copolymer (5/95); vinyl caprolactam/vinyl acetate copolymer (5/95); and resins sold under the trade names Ultrahold CA 8® by Ciba Geigy (ethyl acrylate/acrylic acid/N-t-butyl acrylamide copolymer); Resyn 28-1310® by National Starch and Luviset CA 66® by BASF (vinyl acetate/crotonic acid copolymer 90/10); Luviset CAP® by BASF (vinyl acetate/vinyl propionate/crotonic acid 50/40/10); Amerhold DR-25® by Union Carbide (ethyl acrylate/methacrylic acid/methyl methacrylate/acrylic acid copolymer), and Poligen A® by BASF (polyacrylate dispersion).

One highly preferred polymer is composed of acrylic acid and t-butyl acrylate monomeric units, preferably with acrylic acid/t-butyl acrylate ratio of from about 90:10 to about 10:90, preferably from about 70:30 to about 15:85, more preferably from about 50:50 to about 20:80, by weight of the polymer. Nonlimiting examples of acrylic acid/tert-butyl acrylate copolymers useful in the present invention are those with an approximate acrylic acid/tert-butyl acrylate weight ratio of about 25:75 and an average molecular weight of from about 70,000 to about 100,000, and those with an approximate acrylic acid/tert-butyl acrylate weight ratio of about 35:65 and an average molecular weight of from about 60,000 to about 90,000.

The film-forming and/or adhesive polymer is present in at least an effective amount to provide shape retention. It is not intended to exclude the use of higher or lower levels of the polymers, as long as an effective amount is used to provide adhesive and film-forming properties to the composition and the composition can be formulated and effectively applied for its intended purpose.

Silicones, typical wrinkle reducing agents, and film-forming polymers can be combined to produce preferred wrinkle reducing actives. Typically the weight ratio of silicone to film-forming polymer is from about 10:1 to about 1:10, preferably from about 5:1 to about 1:5, and more preferably from about 2:1 to about 1:2.

Other preferred adhesive and/or film forming polymers that are useful in the composition of the present invention actually contain silicone moieties in the polymers themselves, typically present as block and/or graft copolymers.

The preferred polymers for use herein have the characteristic of providing a natural appearing "drape" in which the fabric does not form wrinkles, or resists deformation.

Compositions according to the present invention, which contain a shape retention polymer having hydrophilic monomers with an acid functional pending group, such as acrylic acid, methacrylic acid, crotonic acid, maleic acid and its half esters, itaconic acid, and mixtures thereof, preferably are adjusted to have a pH of greater than about 6.5, preferably from about 7 and about 0.5, more preferably from about 8 to about 10.5, most preferably from about 9 to about 10.5 to improve the solubility of the polymer. This is achieved by the addition of a caustic alkali. Example of suitable caustic alkalis for use herein include sodium and potassium hydroxide.

3. Hydrophilic Plasticizer

Compositions may also contain a hydrophilic plasticizer to soften the fabric fibers, especially cotton fibers, and the adhesive and/or film-forming shape retention polymers. Examples of the preferred hydrophilic plasticizers are short chain polyhydric alcohols, such as glycerol, ethylene glycol, propylene glycol, diethylene glycol, dipropylene glycol, sorbitol, erythritol or mixtures thereof, more preferably diethylene glycol, dipropylene glycol, ethylene glycol, propylene glycol and mixtures thereof.

The aqueous compositions containing these plasticizers also tend to provide a slower drying profile for clothing/fabrics, to allow time for any wrinkles to disappear when the clothing/fabrics are hung to dry. This is balanced by the desire by most consumer to have the garments to dry faster. Therefore, when needed, the plasticizers should be used at an effective, but as low as possible, level in the composition.

4. Lithium Salts

The compositions of the present invention may further contain lithium salts and lithium salt hydrates to provide improved fabric wrinkle control. Nonlimiting examples of lithium salts that are useful in the present invention are lithium bromide, lithium bromide hydrate, lithium chloride, lithium chloride hydrate, lithium acetate, lithium acetate dihydrate, lithium lactate, lithium sulfate, lithium sulfate monohydrate, lithium tartrate, lithium bitartrate, and mixtures thereof, preferably lithium bromide, lithium lactate, and mixtures thereof.

5. Mixtures

As stated hereinbefore, the compositions of the present invention may also contain mixtures of fiber lubricant, shape retention polymer, plasticizer, and/or lithium salts to impart improved wrinkle control to the fabrics.

C. Static Control Agents

The composition of the present invention may also contain an effective amount of anti-static or static control agent to provide laundered fabrics with improved in-wear static control. Preferred anti-static agents are those that are water soluble. Nonlimiting examples of these antistatic agents are polymeric quaternary ammonium salts, such as polymers conforming to the general formula:

$$[N(CH_3)_2—(CH_2)_3—NH—CO—NH—(CH_2)_3—N(CH_3)_2{}^+—CH_2CH_2OCH_2CH_2]_x{}^{2+}2x[Cl^-]$$

(commercially available under the trade name Mirapol A-15® from Rhône-Poulenc); and $$[N(CH_3)_2—(CH_2)_3—NH—CO—(CH_2)_4—CO—NH—(CH_2)_3—N(CH_3)_2—(CH_2CH_2OCH_2CH_2]_x{}^+x[Cl^-],$$

(commercially available under the trade name Mirapol AD-1® from Rhône-Poulenc), quaternized polyethyleneimines, vinylpyrrolidone/methacrylamidopropyltrimethylammonium chloride copolymer, available under the trade name Gafquat HS-100® from GAF; triethonium hydrolyzed collagen ethosulfate, available under the trade name Quat-Pro E® from Maybrook; neutralized sulfonated polystyrene, available, e.g., under the trade name Versa TL-130® from Alco Chemical, neutralized sulfonated styrene/maleic anhydride copolymers, available, e.g., under the trade name Versa TL-4® from Alco Chemical; polyethylene glycols; and mixtures thereof. Another useful anti-static agent is Variquat-66 available from Goldschmidt.

It is preferred that a no foaming, or low foaming agent is used to avoid foam formation during fabric treatment. It is also preferred that polyethoxylated agents such as polyethylene glycol or Variquat 66® are not used when alpha-cyclodextrin is used. The polyethoxylate groups have a strong affinity to, and readily complex with, alpha-cyclodextrin which in turn depletes the uncomplexed cyclodextrin available for odor control.

D. Sanitization Agents

Sanitization of fabrics can be achieved by the compositions and articles of the present invention containing, antimicrobial materials, e.g., antibacterial halogenated compounds, quaternary compounds, phenolic compounds and metallic salts, and preferably quaternary compounds. A typical disclosure of these antimicrobial can be found in International Patent Application No. PCT/US 98/12154 pages 17 to 20.

1. Biguanides

Some of the more robust antimicrobial halogenated compounds which can function as disinfectants/sanitizers as well as finish product preservatives (vide infra), and that are useful in the compositions of the present invention include 1,1'-hexamethylene bis(5-(p-chlorophenyl)biguanide), commonly known as chlorhexidine, and its salts, e.g., with hydrochloric, acetic and gluconic acids. The digluconate salt is highly water-soluble, about 70% in water, and the diacetate salt has a solubility of about 1.8% in water.

Other useful biguanide compounds include Cosmoci® CQ®, and Vantocil® IB that include poly (hexamethylene biguanide) hydrochloride. Other useful cationic antimicrobial agents include the bis-biguanide alkanes. Usable water soluble salts of the above are chlorides, bromides, sulfates, alkyl sulfonates such as methyl sulfonate and ethyl sulfonate, phenylsulfonates such as p-methylphenyl sulfonates, nitrates, acetates, gluconates, and the like.

Examples of suitable bis biguanide compounds are chlorhexidine; 1,6-bis-(2-ethylhexylbiguanidohexane)dihydrochloride; 1,6-di-($N_1$,$N_1$'-phenyldiguanido-$N_5$,$N_5$')-hexane tetrahydrochloride; 1,6-di-($N_1$,$N_1$'-phenyl-$N_1$,$N_1$'-methyldiguanido-$N_5$,$N_5$')-hexane dihydrochloride; 1,6-di($N_1$,$N_1$'-o-chlorophenyldiguanido-$N_5$,$N_5$')-hexane dihydrochloride; 1,6-di($N_1$,$N_1$'-2,6-dichlorophenyldiguanido-$N_5$,$N_5$')hexane dihydrochloride; 1,6-di[$N_1$,$N_1$'-.beta.-(p-methoxyphenyl) diguanido-$N_5$,$N_5$']-hexane dihydrochloride; 1,6-di($N_1$,$N_1$'-.alpha.-methyl-.beta.-phenyldiguanido-$N_5$,$N_5$')-hexane dihydrochloride; 1,6-di($N_1$,$N_1$'-p-nitrophenyldiguanido-$N_5$,$N_5$') hexane dihydrochloride;.omega.:.omega.'-di-($N_1$,$N_1$'-phenyldiguanido-$N_5$,$N_5$')-di-n-propylether dihydrochloride; omega:omega'-di($N_1$,$N_1$'-p-chlorophenyldiguanido-$N_5$,$N_5$')-di-n-propylether tetrahydrochloride; 1,6-di($N_1$,$N_1$'-2,4-dichlorophenyldiguanido-$N_5$,$N_5$')hexane tetrahydrochloride; 1,6-di($N_1$,$N_1$'-p-methylphenyldiguanido-$N_5$,$N_5$') hexane dihydrochloride; 1,6-di($N_1$,$N_1$'-2,4,5-trichlorophenyldiguanido-$N_5$,$N_5$')hexane tetrahydrochloride; 1,6-di[$N_1$,$N_1$'-.alpha.-(p-chlorophenyl) ethyldiguanido-$N_5$,$N_5$']hexane dihydrochloride;.omega.:.omega.'di($N_1$, $N_1$'-p-chlorophenyldiguanido-$N_5$,$N_5$')m-xylene dihydrochloride; 1,12-di($N_1$,$N_1$'-p-chlorophenyldiguanido-$N_5$,$N_5$')dodecane dihydrochloride; 1,10-di($N_1$, $N_1$'-phenyldiguanido-$N_5$,$N_5$')-decane tetrahydrochloride; 1,12-di($N_1$,$N_1$'-phenyldiguanido-$N_5$,$N_5$')dodecane tetrahydrochloride; 1,6-di($N_1$,$N_1$'-o-chlorophenyldiguanido-$N_5$, $N_5$') hexane dihydrochloride; 1,6-di($N_1$,$N_1$'-p-chlorophenyldiguanido-$N_5$,$N_5$')-hexane tetrahydrochloride; ethylene bis (1-tolyl biguanide); ethylene bis (p-tolyl biguanide); ethylene bis(3,5-dimethylphenyl biguanide); ethylene bis(p-tert-amylphenyl biguanide); ethylene bis(nonylphenyl biguanide); ethylene bis (phenyl biguanide); ethylene bis (N-butylphenyl biguanide); ethylene bis (2,5-diethoxyphenyl biguanide); ethylene bis(2,4-dimethylphenyl biguanide); ethylene bis(o-diphenylbiguanide); ethylene bis(mixed amyl naphthyl biguanide); N-butyl ethylene bis(phenylbiguanide); trimethylene bis(o-tolyl biguanide); N-butyl trimethylene bis(phenyl biguanide); and the corresponding pharmaceutically acceptable salts of all of the above such as the acetates; gluconates; hydrochlorides; hydrobromides; citrates; bisulfites; fluorides; polymaleates; N-coconutalkylsarcosinates; phosphites; hypophosphites; perfluorooctanoates; silicates; sorbates; salicylates; maleates; tartrates; fumarates; ethylenediaminetetraacetates; iminodiacetates; cinnamates; thiocyanates; arginates; pyromellitates; tetracarboxybutyrates; benzoates; glutarates; monofluorophosphates; and perfluoropropionates, and mixtures thereof. Preferred antimicrobials from this group are 1,6-di-($N_1$,$N_1$'-phenyldiguanido-$N_5$,$N_5$')-hexane tetrahydrochloride; 1,6-di($N_1$, $N_1$'-o-chlorophenyldiguanido-$N_5$,$N_5$')-hexane dihydrochloride; 1,6-di($N_1$,$N_1$'-2,6-dichlorophenyldiguanido-$N_5$,$N_5$')hexane dihydrochloride; 1,6-di($N_1$,$N_1$'-2,4-dichlorophenyldiguanido-$N_5$,$N_5$')hexane tetrahydrochloride; 1,6-di[$N_1$,$N_1$'-.alpha.-(p-chlorophenyl) ethyldiguanido-$N_5$,$N_5$']hexane dihydrochloride;.omega.:.omega.'di($N_1$, $N_1$'-p-chlorophenyldiguanido-$N_5$,$N_5$')m-xylene dihydrochloride; 1,12-di($N_1$,$N_1$'-p-chlorophenyldiguanido-$N_5$,$N_5$')dodecane dihydrochloride; 1,6-di($N_1$,$N_1$'-o-chlorophenyldiguanido-$N_5$,$N_5$')hexane dihydrochloride; 1,6-di($N_1$,$N_1$'-p-chlorophenyldiguanido-$N_5$,$N_5$')-hexane tetrahydrochloride; and mixtures thereof; more preferably, 1,6-di($N_1$,$N_1$'-o-chlorophenyldiguanido-$N_5$,$N_5$')-hexane dihydrochloride; 1,6-di($N_1$,$N_1$'-2,6-dichlorophenyldiguanido-$N_5$,$N_5$')hexane dihydrochloride; 1,6-di($N_1$,$N_1$'-2,4-dichlorophenyldiguanido-$N_5$,$N_5$')hexane tetrahydrochloride; 1,6-di[$N_1$,$N_1$'-.alpha.-(p-chlorophenyl) ethyldiguanido-$N_5$,$N_5$']hexane dihydrochloride;.omega.:.omega.'di($N_1$, $N_1$'-p-chlorophenyldiguanido-$N_5$,$N_5$')m-xylene dihydrochloride; 1,12-di($N_1$,$N_1$'-p-chlorophenyldiguanido-$N_5$,$N_5$')dodecane dihydrochloride; 1,6-di($N_1$,$N_1$'-o-chlorophenyldiguanido-$N_5$,$N_5$')hexane dihydrochloride; 1,6-di($N_1$,$N_1$'-p-chlorophenyldiguanido-$N_5$,$N_5$')-hexane tetrahydrochloride; and mixtures thereof. As stated hereinbefore, the bis biguanide of choice is chlorhexidine its salts, e.g., digluconate, dihydrochloride, diacetate, and mixtures thereof.

2. Quaternary Compounds

A wide range of quaternary compounds can also be used as antimicrobial actives for the compositions of the present invention. Non-limiting examples of useful quaternary compounds include: (1) benzalkonium chlorides and/or substituted benzalkonium chlorides such as commercially available Barquat® (available from Lonza), Maquat® (available from Mason), Variquat® (available from Goldschmidt), and Hyamine® (available from Lonza); (2) di($C_6$–$C_{14}$)alkyl di short chain ($C_{1-4}$ alkyl and/or hydroxyalkyl) quaternary such as Bardac® products of Lonza, (3) N-(3-chloroallyl) hexaminium chlorides such as Dowicide® and Dowicil® available from Dow; (4) benzethonium chloride such as Hyamine® 1622 from Rohm & Haas; (5) methylbenzethonium chloride represented by Hyamine® 10× supplied by Rohm & Haas, (6) cetylpyridinium chloride such as Cepacol chloride available from of Merrell Labs. Examples of the preferred dialkyl quaternary compounds are di($C_8$–$C_{12}$)dialkyl dimethyl ammonium chloride, such as didecyldimethylammonium chloride (Bardac 22), and dioctyldimethylammonium chloride (Bardac 2050).

Surfactants, when added to the antimicrobials tend to provide improved antimicrobial action. This is especially true for the siloxane surfactants, and especially when the siloxane surfactants are combined with the chlorhexidine antimicrobial actives.

Examples of bactericides used in the compositions and articles of this invention include glutaraldehyde, formaldehyde, 2-bromo-2-nitro-propane-1,3-diol sold by Inolex Chemicals, located in Philadelphia, Pa., under the trade name Bronopol®, and a mixture of 5-chloro-2-methyl-4-isothiazoline-3-one and 2-methyl-4-isothiazoline-3-one sold by Rohm and Haas Company under the trade name Kathon CG/ICP®.

3. Metallic Salts

Many metallic salts are known for their antimicrobial effects. These metallic salts may be selected from the group consisting of copper salts, zinc salts, and mixtures thereof.

Copper salts have some antimicrobial benefits. Specifically, cupric abietate acts as a fungicide, copper acetate acts as a mildew inhibitor, cupric chloride acts as a fungicide, copper lactate acts as a fungicide, and copper sulfate acts as a germicide. Copper salts also possess some malodor control abilities as described in more detail below. For instance, U.S. Pat. No. 3,172,817, Leupold, et al., describes deodorizing compositions for treating disposable articles, comprising at least slightly water-soluble salts of acylacetone, including copper salts and zinc salts E. Drying Agents Optionally, the composition may contain a humectant, such as glycerine, or an inorganic hygroscopic material, to provide slower drying for clothing/fabrics. Slower drying times may be preferred where the fabrics are also being treated with a wrinkle control agent or other active that requires additional time to effect the associated benefit. This is particularly preferred where laundered fabrics are hung to dry. For most purposes however, this is preferably not present, since normally the user wants the clothing/fabrics to dry sooner.

F. Stain Resistant Agents and Soil Release Agents

1. Soil Releasing Polymers

In the present invention, a soil release agent may be incorporated into compositions and articles for distribution in the laundry solution and deposition on the laundered fabrics. Preferably, such a soil release agent is a polymer. One type of preferred soil release agent is a copolymer having random blocks of ethylene terephthalate and polyethylene oxide (PEO) terephthalate. The molecular weight of this polymeric soil release agent is in the range of from about 25,000 to about 55,000. Descriptions of such copolymers and their uses are provided in U.S. Pat. No. 3,959,230 to Hays, issued May 25, 1976 and U.S. Pat. No. 3,893,929 to Basadur issued Jul. 8, 1975.

Another preferred soil release polymer is a crystallizable polyester with repeating units of ethylene terephthalate containing from about 10% to about 15% by weight of ethylene terephthalate units together with from about 10% to about 50% by weight of polyoxyethylene terephthalate units that are derived from a polyoxyethylene glycol of average molecular weight of from about 300 to about 6,000. The molar ratio of ethylene terephthalate units to polyoxyethylene terephthalate units in such a crystallizable polymeric compound is between 2:1 and 6:1. Examples of this polymer include the commercially available materials Zelcon 4780® and Zelcon 5126 (from Dupont) and Milease T® (from ICI). See also U.S. Pat. No. 4,702,857, issued Oct. 27, 1987 to Gosselink.

Highly preferred soil release agents are polymers of the generic formula:

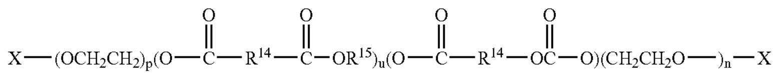

in which each X can be a suitable capping group, with each X typically being selected from the group consisting of H, and alkyl or acyl groups containing from about 1 to about 4 carbon atoms. p is selected for water solubility and generally is from about 6 to about 113, preferably from about 20 to about 50. u is critical to formulation in a liquid composition having a relatively high ionic strength. There should be very little material in which u is greater than 10. Furthermore, there should be at least 20%, preferably at least 40%, of material in which u ranges from about 3 to about 5.

The $R^{14}$ moieties are essentially 1,4-phenylene moieties. As used herein, the term "the $R^{14}$ moieties are essentially 1,4-phenylene moieties" refers to compounds where the $R^{14}$ moieties consist entirely of 1,4-phenylene moieties, or are partially substituted with other arylene or alkarylene moieties, alkylene moieties, alkenylene moieties, or mixtures thereof. Arylene and alkarylene moieties which can be partially substituted for 1,4-phenylene include 1,3-phenylene, 1,2-phenylene, 1,8-naphthylene, 1,4-naphthylene, 2,2-biphenylene, 4,4-biphenylene, and mixtures thereof. Alkylene and alkenylene moieties which can be partially substituted include 1,2-propylene, 1,4-butylene, 1,5-pentylene, 1,6-hexamethylene, 1,7-heptamethylene, 1,8-octamethylene, 1,4-cyclohexylene, and mixtures thereof.

For the $R^{14}$ moieties, the degree of partial substitution with moieties other than 1,4-phenylene should be such that the soil release properties of the compound are not adversely affected to any great extent. Generally the degree of partial substitution which can be tolerated will depend upon the backbone length of the compound, i.e., longer backbones can have greater partial substitution for 1,4-phenylene moieties. Usually, compounds where the $R^{14}$ comprise from about 50% to about 100% 1,4-phenylene moieties (from 0% to about 50% moieties other than 1,4-phenylene) have adequate soil release activity. For example, polyesters made with a 40:60 mole ratio of isophthalic (1,3-phenylene) to terephthalic (1,4-phenylene) acid have adequate soil release activity. However, because most polyesters used in fiber making comprise ethylene terephthalate units, it is usually desirable to minimize the degree of partial substitution with moieties other than 1,4-phenylene for best soil release activity. Preferably, the $R^{14}$ moieties consist entirely of (i.e., comprise 100%) 1,4-phenylene moieties, i.e., each $R^{14}$ moiety is 1,4-phenylene.

For the $R^{15}$ moieties, suitable ethylene or substituted ethylene moieties include ethylene, 1,2-propylene, 1,2-butylene, 1,2-hexylene, 3-methoxy-1,2-propylene, and mixtures thereof. Preferably, the $R^{15}$ moieties are essentially ethylene moieties, 1,2-propylene moieties, or mixtures thereof. Inclusion of a greater percentage of ethylene moieties tends to improve the soil release activity of compounds.

Surprisingly, inclusion of a greater percentage of 1,2-propylene moieties tends to improve the water solubility of compounds. Therefore, the use of 1,2-propylene moieties or a similar branched equivalent is desirable for incorporation of any substantial part of the soil release polymer where the fabric care composition will be added to a laundry solution containing fabric softening actives. Preferably, from about 75% to about 100%, are 1,2-propylene moieties.

The value for each p is at least about 6, and preferably is at least about 10. The value for each n usually ranges from about 12 to about 113. Typically the value for each p is in the range of from about 12 to about 43.

A more complete disclosure of soil release agents is contained in U.S. Pat. No. 4,018,569, Trinh, Gosselink and Rattinger, issued Apr. 4, 1989; U.S. Pat. No. 4,661,267, Decker, Konig, Straathof, and Gosselink, issued Apr. 28, 1987; U.S. Pat. No. 4,702,857, Gosselink, issued Oct. 27, 1987; U.S. Pat. No. 4,711,730, Gosselink and Diehl, issued Dec. 8, 1987; U.S. Pat. No. 4,749,596, Evans, Huntington, Stewart, Wolf, and Zimmerer, issued Jun. 7, 1988; U.S. Pat. No. 4,808,086, Evans, Huntington, Stewart, Wolf, and Zimmerer, issued Feb. 24, 1989; U.S. Pat. No. 4,818,569, Trinh, Gosselink, and Rattinger, issued Apr. 4, 1989; U.S. Pat. No. 4,877,896, Maldonado, Trinh, and Gosselink, issued Oct. 31, 1989; U.S. Pat. No. 4,956,447, Gosselink et al., issues Sep. 11, 1990; U.S. Pat. No. 4,968,451, Scheibel and Gosselink, issued Nov. 6, 1990; and U.S. Pat. No. 4,976,879, Maldonado, Trinh, and Gosselink, issued Dec. 11, 1990.

Polymeric soil release actives useful in the present invention may also include cellulosic derivatives such as hydroxyether cellulosic polymers, and the like. Such agents are commercially available and include hydroxyethers of cellulose such as METHOCEL (Dow). Cellulosic soil release agents for use herein also include those selected from the group consisting of $C_1$–$C_4$ alkyl and $C_4$ hydroxyalkyl cellulose; see U.S. Pat. No. 4,000,093, issued Dec. 28, 1976 to Nicol, et al.

Soil release agents characterized by poly(vinyl ester) hydrophobe segments include graft copolymers of poly (vinyl ester), e.g., $C_1$–$C_6$ vinyl esters, preferably poly(vinyl acetate) grafted onto polyalkylene oxide backbones, such as polyethylene oxide backbones. See European Patent Application 0 219 048, published Apr. 22, 1987 by Kud, et al. Commercially available soil release agents of this kind include the SOKALAN type of material, e.g., SOKALAN HP-22, available from BASF (Germany).

Still another preferred soil release agent is an oligomer with repeat units of terephthaloyl units, sulfoisoterephthaloyl units, oxyethyleneoxy and oxy-1,2-propylene units. The repeat units form the backbone of the oligomer and are preferably terminated with modified isethionate end-caps. A particularly preferred soil release agent of this type comprises about one sulfoisophthaloyl unit, 5 terephthaloyl units, oxyethyleneoxy and oxy-1,2-propyleneoxy units in a ratio of from about 1.7 to about 1.8, and two end-cap units of sodium 2-(2-hydroxyethoxy)-ethanesulfonate. Said soil release agent also comprises from about 0.5% to about 20%, by weight of the oligomer, of a crystalline-reducing stabilizer, preferably selected from the group consisting of xylene sulfonate, cumene sulfonate, toluene sulfonate, and mixtures thereof.

The compositions and articles of the present invention may also contain soil release and anti-redeposition agents such as water-soluble ethoxylated amines, most preferably ethoxylated tetraethylenepentamine. Exemplary ethoxylated amines are further described in U.S. Pat. No. 4,597,898, VanderMeer, issued Jul. 1, 1986.

Another group of preferred clay soil removal-antiredeposition agents are the cationic compounds disclosed in European Patent Application 111,965, Oh and Gosselink, published Jun. 27, 1984. Other clay soil removal/antiredeposition agents which can be used include the ethoxylated amine polymers disclosed in European Patent Application 111,984, Gosselink, published Jun. 27, 1984; the zwitterionic polymers disclosed in European Patent Application 112,592, Gosselink, published Jul. 4, 1984; and the amine oxides disclosed in U.S. Pat. No. 4,548,744, Connor, issued Oct. 22, 1985. Other clay soil removal and/or anti redeposition agents known in the art can also be utilized in the compositions herein. Another type of preferred antiredeposition agent includes the carboxymethylcellulose (CMC) materials. These materials are well known in the art.

2. Scum Dispersants

These soil release actives will typically also act as scum dispersants. However, the composition and articles of the present invention may also contain a scum dispersant other than these soil release agents. The preferred scum dispersants herein are formed by highly ethoxylating hydrophobic materials. The hydrophobic material can be a fatty alcohol, fatty acid, fatty amine, fatty acid amide, amine oxide, quaternary ammonium compound, or the hydrophobic moieties used to form soil release polymers. The preferred scum dispersants are highly ethoxylated, e.g., more than about 17, preferably more than about 25, more preferably more than about 40, molecules of ethylene oxide per molecule on the average, with the polyethylene oxide portion being from about 76% to about 97%, preferably from about 81% to about 94%, of the total molecular weight.

The level of scum dispersant is sufficient to keep the scum at an acceptable, preferably unnoticeable to the consumer, level under the conditions of use. However, it is to be noted that excessive scum dispersant may adversely affect softening where the use of fabric softener actives are to be added to the laundry solution.

For some purposes it is desirable that the scum is nonexistent. Depending on the amount of anionic or nonionic detergent, etc., used in the wash cycle of a typical laundering process, the efficiency of the rinsing steps prior to the introduction of the compositions herein, and the water hardness, the amount of anionic or nonionic detergent surfactant and detergency builder (especially phosphates and zeolites) entrapped in the fabric (laundry) will vary. Normally, the minimum amount of scum dispersant should be used to avoid adversely affecting softening properties.

Preferred scum dispersants are: Brij 700®; Varonic U-250®; Genapol T-500®, Genapol T-800®; Plurafac A-79®; and Neodol 25-50®.

G. Malodor Control Agents

The compositions for odor control are of the type disclosed in U.S. Pat. Nos. 5,534,165; 5,578,563; 5,663,134; 5,668,097; 5,670,475; and 5,714,137, Trinh et al. issued Jul. 9, 1996; Nov. 26, 1996; Sep. 2, 1997; Sep. 16, 1997; Sep. 23, 1997; and Feb. 3, 1998 respectively, all of said patents being incorporated herein by reference. Such compositions can contain several different optional odor control agents.

1. Cyclodextrin

As used herein, the term "cyclodextrin" includes any of the known cyclodextrins such as unsubstituted cyclodextrins containing from six to twelve glucose units, especially, alpha-cyclodextrin, beta-cyclodextrin, gamma-cyclodextrin and/or their derivatives and/or mixtures thereof. The alpha-cyclodextrin consists of six glucose units, the beta-cyclodextrin consists of seven glucose units, and the gamma-cyclodextrin consists of eight glucose units arranged in donut-shaped rings. The specific coupling and conformation of the glucose units give the cyclodextrins rigid, conical molecular structures with hollow interiors of specific volumes. The "lining" of each internal cavity is formed by hydrogen atoms and glycosidic bridging oxygen atoms; therefore, this surface is fairly hydrophobic. The unique shape and physical-chemical properties of the cavity enable the cyclodextrin molecules to absorb (form inclusion complexes with) organic molecules or parts of organic molecules which can fit into the cavity. Many odorous molecules can fit into the cavity including many malodorous molecules and perfume molecules. Therefore, cyclodextrins, and especially mixtures of cyclodextrins with different size cavities, can be used to control odors caused by a broad spectrum of organic odoriferous materials, which may, or may not, contain reactive functional groups.

The complexing between cyclodextrin and odorous molecules occurs rapidly in the presence of water. However, the extent of the complex formation also depends on the polarity of the absorbed molecules. In an aqueous solution, strongly hydrophilic molecules (those which are highly water-soluble) are only partially absorbed, if at all. Therefore, cyclodextrin does not complex effectively with some very low molecular weight organic amines and acids when they are present at low levels. As the water is being removed however, e.g., the fabric is being dried off, some low molecular weight organic amines and acids have more affinity and will complex with the cyclodextrins more readily.

The cavities within the cyclodextrin should remain essentially unfilled (the cyclodextrin remains uncomplexed) while in solution, in order to allow the cyclodextrin to absorb various odor molecules when the solution is applied to a surface. Non-derivatised (normal) beta-cyclodextrin can be present at a level up to its solubility limit of about 1.85% (about 1.85 g in 100 grams of water) at room temperature. Beta-cyclodextrin is not preferred in compositions which call for a level of cyclodextrin higher than its water solubility limit. Non-derivatised beta-cyclodextrin is generally not preferred when the composition contains surfactant since it affects the surface activity of most of the preferred surfactants that are compatible with the derivatised cyclodextrins.

Cyclodextrins that are useful in the present invention are highly water-soluble such as, alpha-cyclodextrin and/or derivatives thereof, gamma-cyclodextrin and/or derivatives thereof, derivatised beta-cyclodextrins, and/or mixtures thereof. The derivatives of cyclodextrin consist mainly of molecules wherein some of the OH groups are converted to OR groups. Cyclodextrin derivatives include, e.g., those with short chain alkyl groups such as methylated cyclodextrins, and ethylated cyclodextrins, wherein R is a methyl or an ethyl group; those with hydroxyalkyl substituted groups, such as hydroxypropyl cyclodextrins and/or hydroxyethyl cyclodextrins, wherein R is a $-CH_2-CH(OH)-CH_3$ or a $-CH_2CH_2-OH$ group; branched cyclodextrins such as maltose-bonded cyclodextrins; cationic cyclodextrins such as those containing 2-hydroxy-3-(dimethylamino)propyl ether, wherein R is $CH_2-CH(OH)-CH_2-N(CH_3)_2$ which is cationic at low pH; quaternary ammonium, e.g., 2-hydroxy-3-(trimethylammonio)propyl ether chloride groups, wherein R is $CH_2-CH(OH)-CH_2-N^+(CH_3)_3Cl^-$; anionic cyclodextrins such as carboxymethyl cyclodextrins, cyclodextrin sulfates, and cyclodextrin succinylates; amphoteric cyclodextrins such as carboxymethyl/quaternary ammonium cyclodextrins; cyclodextrins wherein at least one glucopyranose unit has a 3-6-anhydro-cyclomalto structure, e.g., the mono-3-6-anhydrocyclodextrins, as disclosed in "Optimal Performances with Minimal Chemical Modification of Cyclodextrins", F. Diedaini-Pilard and B. Perly, The 7th International Cyclodextrin Symposium Abstracts, April 1994, p. 49, said references being incorporated herein by reference; and mixtures thereof. Other cyclodextrin derivatives are disclosed in U.S. Pat. Nos. 3,426,011; 3,453,257; 3,453,258; 3,453,259; 3,453,260; 3,459,731; 3,553,191; 3,565,887; 4,535,152; 4,616,008; 4,678,598; 4,638,058; and 4,746,734.

Highly water-soluble cyclodextrins are those having water solubility of at least about 10 g in 100 ml of water at room temperature, preferably at least about 20 g in 100 ml of water, more preferably at least about 25 g in 100 ml of water at room temperature. The availability of solubilized, uncomplexed cyclodextrins is essential for effective and efficient odor control performance. Solubilized, water-soluble cyclodextrin can exhibit more efficient odor control performance than non-water-soluble cyclodextrin when deposited onto surfaces, especially fabric.

Examples of preferred water-soluble cyclodextrin derivatives suitable for use herein are hydroxypropyl alpha-cyclodextrin, methylated alpha-cyclodextrin, methylated beta-cyclodextrin, hydroxyethyl beta-cyclodextrin, and hydroxypropyl beta-cyclodextrin. Hydroxyalkyl cyclodextrin derivatives preferably have a degree of substitution of from about 1 to about 14, more preferably from about 1.5 to about 7, wherein the total number of OR groups per cyclodextrin is defined as the degree of substitution. Methylated cyclodextrin derivatives typically have a degree of substitution of from about 1 to about 18, preferably from about 3 to about 16. A known methylated beta-cyclodextrin is heptakis-2,6-di-O-methyl-,-cyclodextrin, commonly known as DIMEB, in which each glucose unit has about 2 methyl groups with a degree of substitution of about 14. A preferred, more commercially available, methylated beta-cyclodextrin is a randomly methylated beta-cyclodextrin, commonly known as RAMEB, having different degrees of substitution, normally of about 12.6. RAMEB is more preferred than DIMEB, since DIMEB affects the surface activity of the preferred surfactants more than RAMEB. The preferred cyclodextrins are available, e.g., from Cerestar USA, Inc. and Wacker Chemicals (USA), Inc.

It is also preferable to use a mixture of cyclodextrins. Such mixtures absorb odors more broadly by complexing with a wider range of odoriferous molecules having a wider range of molecular sizes. Preferably at least a portion of the cyclodextrins is alpha-cyclodextrin and its derivatives thereof, gamma-cyclodextrin and its derivatives thereof, and/or derivatised beta-cyclodextrin, more preferably a mixture of alpha-cyclodextrin, or an alpha-cyclodextrin derivative, and derivatised beta-cyclodextrin, even more preferably a mixture of derivatised alpha-cyclodextrin and derivatised beta-cyclodextrin, most preferably a mixture of hydroxypropyl alpha-cyclodextrin and hydroxypropyl beta-cyclodextrin, and/or a mixture of methylated alpha-cyclodextrin and methylated beta-cyclodextrin.

2. Low Molecular Weight Polyols

Low molecular weight polyols with relatively high boiling points, as compared to water, such as ethylene glycol, propylene glycol and/or glycerol are preferred optional ingredients for improving odor control performance of the composition of the present invention, especially when cyclodextrin is present. The incorporation of a small amount of low molecular weight glycols into the compositions and articles of the present invention typically enhances the formation of the cyclodextrin inclusion complexes as the treated fabrics dry.

The polyols' ability to remain on the fabric for a longer period of time than water, as the fabrics dry, typically allows it to form ternary complexes with the cyclodextrin and some malodorous molecules. The addition of the glycols tends to fill up void space in the cyclodextrin cavity that is unable to be filled by some malodor molecules of relatively smaller sizes. Preferably the glycol used is glycerin, ethylene glycol, propylene glycol, diethylene glycol, dipropylene glycol or mixtures thereof, and more preferably ethylene glycol and/or propylene glycol. Cyclodextrins prepared by processes that result in a level of such polyols are highly desirable, since they can be used without removal of the polyols.

Some polyols, e.g., dipropylene glycol, are also useful to facilitate the solubilization of some perfume ingredients in the composition of the present invention.

Typically, glycol is added to a composition of the present invention at a level of from about 0.01% to about 3%, by weight of the composition, preferably from about 0.05% to about 1%, more preferably from about 0.1% to about 0.5%, by weight of the composition. The preferred weight ratio of low molecular weight polyol to cyclodextrin is from about 2:1,000 to about 20:100, more preferably from about 3:1,000 to about 15:100, even more preferably from about 5:1,000 to about 10:100, and most preferably from about 1:100 to about 7:100.

3. Metal Salts

Optionally, but highly preferred, the present invention can include metallic salts for added odor absorption and/or antimicrobial benefit particularly when cyclodextrin is present. The metallic salts are selected from the group consisting of copper salts, zinc salts, and mixtures thereof.

Copper salts have some antimicrobial benefits. Specifically, cupric abietate acts as a fungicide, copper acetate acts as a mildew inhibitor, cupric chloride acts as a fungicide, copper lactate acts as a fungicide, and copper sulfate acts as a germicide. Copper salts also possess some malodor control abilities. See U.S. Pat. No. 3,172,817, which discloses deodorizing compositions for treating disposable articles, comprising at least slightly water-soluble salts of acylacetone, including copper salts and zinc salts, all of said patents are incorporated herein by reference.

The preferred zinc salts possess malodor control abilities. Zinc has been used most often for its ability to ameliorate malodor, e.g., in mouth wash products, as disclosed in U.S. Pat. Nos. 4,325,939, and 4,469,674. Highly-ionized and soluble zinc salts such as zinc chloride, provide the best source of zinc ions. Zinc borate functions as a fungistat and a mildew inhibitor, zinc caprylate functions as a fungicide, zinc chloride provides antiseptic and deodorant benefits, zinc ricinoleate functions as a fungicide, zinc sulfate heptahydrate functions as a fungicide and zinc undecylenate functions as a fungistat.

Preferably, the metallic salts are water-soluble zinc salts, copper salts or mixtures thereof, and more preferably zinc salts, especially $ZnCl_2$. These salts are preferably present in the present invention primarily to absorb amine and sulfur-containing compounds that have molecular sizes too small to be effectively complexed with the cyclodextrin molecules. Low molecular weight sulfur-containing materials, e.g., sulfide and mercaptans, are components of many types of malodors, e.g., food odors (garlic, onion), body/perspiration odor, breath odor, etc. Low molecular weight amines are also components of many malodors, e.g., food odors, body odors, urine, etc.

When metallic salts are added to the composition of the present invention they are typically present at a level of from about 0.1% to about 10%, preferably from about 0.2% to about 8%, more preferably from about 0.3% to about 5% by weight of the composition.

4. Soluble Carbonate and/or Bicarbonate Salts

Water-soluble alkali metal carbonate and/or bicarbonate salts, such as sodium bicarbonate, potassium bicarbonate, potassium carbonate, cesium carbonate, sodium carbonate, and mixtures thereof can be added to the composition of the present invention in order to help to control certain acid-type odors. Preferred salts are sodium carbonate monohydrate, potassium carbonate, sodium bicarbonate, potassium bicarbonate, and mixtures thereof. When these salts are used in a composition of the present invention, they are typically present at a level of from about 0.1% to about 5%, preferably from about 0.2% to about 3%, more preferably from about 0.3% to about 2%, by weight of the composition. When these salts are added to a composition of the present invention it is preferable that incompatible metal salts are not present in the composition. Preferably, when these salts are used the composition should be essentially free of zinc and other incompatible metal ions, e.g., Ca, Fe, Ba, etc. which form water-insoluble salts 5. Enzymes Enzymes can be used to control certain types of malodor, especially malodor from urine and other types of excretions, including regurgitated materials.

Proteases are especially desirable. The activity of commercial enzymes depends very much on the type and purity of the enzyme being considered. Enzymes that are water soluble proteases like pepsin, tripsin, ficin, bromelin, papain, rennin, and mixtures thereof are particularly useful. Nonlimiting examples of suitable, commercially available, water soluble proteases are pepsin, tripsin, ficin, bromelin, papain, rennin, and mixtures thereof. Papain can be isolated, e.g., from papaya latex, and is available commercially in the purified form of up to, e.g., about 80% protein, or cruder, technical grade of much lower activity. Other suitable examples of proteases are the subtilisins which are obtained from particular strains of *B. subtilis* and *B. licheniforns*. Another suitable protease is obtained from a strain of *Bacillus*, having maximum activity throughout the pH range of 8–12, developed and sold by Novo Industries A/S under the registered trade name ESPERASE®. The preparation of this enzyme and analogous enzymes is described in British Patent Specification No. 1,243,784. Proteolytic enzymes suitable for removing protein-based stains that are commercially available include those sold under the trade names ALCALASE® and SAVINASE® by Novo Industries A/S (Denmark) and MAXATASE® by International Bio-Synthetics, Inc. (The Netherlands). Other proteases include Protease A (see European Patent Application 130,756, published Jan. 9, 1985); Protease B (see European Patent Application Serial No. 87303761.8, and European Patent Application 130,756); and proteases made by Genencor International, Inc., according to one or more of the following patents: U.S. Pat. Nos. 5,185,258, 5,204,015 and 5,244,791.

A wide range of enzyme materials and means for their incorporation into compositions are also disclosed in U.S. Pat. No. 3,553,139. Enzymes are further disclosed in U.S. Pat. No. 4,101,457 and in U.S. Pat. No. 4,507,219. Other enzyme materials useful for liquid formulations, and their incorporation into such formulations, are disclosed in U.S. Pat. No. 4,261,868. Enzymes can be stabilized by various techniques, e.g., those disclosed and exemplified in U.S. Pat. No. 3,600,319, European Patent Application Publication No. 0 199 405, and in U.S. Pat. No. 3,519,570.

Enzyme-polyethylene glycol conjugates are also preferred. Such polyethylene glycol (PEG) derivatives of enzymes, wherein the PEG or alkoxy-PEG moieties are coupled to the protein molecule through, e.g., secondary amine linkages. Suitable derivatization decreases immunogenicity, thus minimizes allergic reactions, while still maintaining some enzymatic activity. An example of protease-PEG's is PEG-subtilisin Carlsberg from *B. lichenniformis* coupled to methoxy-PEGs through secondary amine linkage, and is available from Sigma-Aldrich Corp., St. Louis, Mo.

6. Zeolites

When the clarity of the solution is not needed, and the solution is not sprayed on fabrics, other optional odor absorbing materials, e.g., zeolites and/or activated carbon, can also be used. A preferred class of zeolites is characterized as "intermediate" silicate/aluminate zeolites. The intermediate zeolites are characterized by $SiO_2/AlO_2$ molar ratios of less than about 10. Preferably the molar ratio of $SiO_2/AlO_2$ ranges from about 2 to about 10. The intermediate zeolites have an advantage over the "high" zeolites. The intermediate zeolites have a higher affinity for amine-type odors, they are more weight efficient for odor absorption because they have a larger surface area, and they are more moisture tolerant and retain more of their odor absorbing capacity in water than the high zeolites. A wide variety of intermediate zeolites suitable for use herein are commercially available as Valfor® CP301-68, Valfor® 300-63, Valfor® CP300-35, and Valfor® CP300-56, available from PQ Corporation, and the CBV100® series of zeolites from Conteka.

Zeolite materials marketed under the trade name Abscents® and Smellrite®, available from The Union Carbide Corporation and UOP are also preferred. These materials are typically available as a white powder in the 3–5 micron particle size range. Such materials are preferred over the intermediate zeolites for control of sulfur-containing odors, e.g., thiols, mercaptans.

7. Activated Carbon

The carbon material suitable for use in the present invention is the material well known in commercial practice as an absorbent for organic molecules and/or for air purification purposes. Often, such carbon material is referred to as "activated" carbon or "activated" charcoal. Such carbon is available from commercial sources under such trade names as; Calgon-Type CPG®; Type PCB®; Type SGL®; Type CAL®; and Type OL®. Activated carbon fibers and cloth may also be used in combination with the compositions and/or articles of manufacture disclosed herein to provide malodor removal and/or freshness benefits. Such activated carbon fibers and fabrics can be acquired from Calgon.

8. Mixtures Thereof

Mixtures of the optional odor control agents described above are desirable, especially when the mixture provides control over a broader range of odors.

H. Dye Fixatives—Dye Transfer Inhibitors

In the laundry operation, especially an operation involving automatic washing machines such as is anticipated in the use of the compositions and articles of the present invention, dye transfer occurs primarily during the wash cycle. This dye transfer during the wash cycle is caused by higher water temperature, longer cycle times, and much higher surfactant concentration in the wash cycle, as compared to the less stringent conditions of the rinse cycle. Thus, it is well known to those skilled in the art to inhibit dye transfer by adding dye transfer inhibitors to detergent compositions in the wash bath solution. For example, European Patent Application 265,257, Clements et al., published Apr. 27, 1988, discloses detergent compositions containing a detergent active, a detergent builder, and a polyvinylpyrrolidone (PVP) mixture. German Pat. No. 3,519,012, Weber et al., published Nov. 27, 1986, teaches a detergent composition comprising nonionic surfactants, PVP components, water-soluble cationic components, and builders, to prevent dye transfer during the wash.

In addition, the use of chlorine scavengers, dye fixatives, dye transfer inhibitors and chelants in a rinse solution is likewise well known to inhibit dye transfer and color degradation during the present rinse cycle as well as during subsequent wash cycles.

1. Chlorine Scavengers

Chlorine scavengers are actives that react with chlorine, or with chlorine-generating materials, such as hypochlorite, to eliminate or reduce the bleaching activity of the chlorine materials. When used in combination with a rinse-added fabric softener, compositions of this invention should incorporate enough chlorine scavenger to neutralize about 0.1 ppm to about 40 ppm, preferably from about 0.2 ppm to about 20 ppm, and even more preferably from about 0.3 ppm to about 10 ppm of chlorine in rinse water.

Chlorine is used in many parts of the world to sanitize water. To make sure that the water is safe, a small amount, typically about 1 to 2 ppm of chlorine is left in the water. It has been found that this small amount of chlorine in the tap water can cause fading of some fabric dyes. Incorporation of a chlorine scavenger in the wash bath solution can provide a benefit by placing the chlorine scavenger at a point where it can intercept the chlorine in the wash water, especially when the chlorine scavenger is highly water soluble, e.g., an ammonium salt as disclosed hereinafter. The chlorine scavenger in the rinse bath solution neutralizes the chlorine in the rinse water where there is no other product added. Further, better distribution of the chlorine scavenger is achieved in the rinse which provides better protection by spreading the scavenger over the fabric more evenly.

The compositions of the present invention should comprise enough chlorine scavenger to react with about 0.1 ppm to about 40 ppm, preferably from about 0.2 ppm to about 20 ppm, and more preferably from about 0.3 ppm to about 10 ppm of chlorine present in an average wash liquor. If both the cation and the anion of the scavenger react with chlorine, which is desirable, the level is adjusted to react with an equivalent amount of available chlorine.

A chlorine scavengers is preferably selected from the group consisting of:

a. amines and their salts;
b. ammonium salts;
c. amino acids and their salts;
d. polyamino acids and their salts;
e. polyethyleneimines and their salts;
f. polyamines and their salts;
g. polyamineamides and their salts;
h. polyacrylamides; and
i. mixtures thereof.

Non-limiting examples of chlorine scavengers include amines, preferably primary and secondary amines, including primary and secondary fatty amines, and alkanolamines; and their salts; ammonium salts, e.g., chloride, bromide, citrate, sulfate; amine-functional polymers and their salts; amino acid homopolymers with amino groups and their salts, such as polyarginine, polylysine, polyhistidine; amino acid copolymers with amino groups and their salts, including 1,5-di-ammonium-2-methyl-panthene dichloride and lysine monohydrochloride; amino acids and their salts, preferably those having more than one amino group per molecule, such as arginine, histidine, and lysine, reducing anions such as sulfite, bisulfite, thiosulfate, nitrite, and antioxidants such as ascorbate, carbamate, phenols; and mixtures thereof.

Preferred chlorine scavengers are water soluble, especially, low molecular weight primary and secondary amines of low volatility, e.g., monoethanolamine, diethanolamine, tris(hydroxymethyl) aminomethane, hexamethylenetetramine, and their salts, and mixtures thereof. Suitable chlorine scavenger polymers include: water soluble amine-functional polymers, e.g., polyethyleneimines, polyamines, polyamineamides, polyacrylamides, and their salts, and mixtures thereof. The preferred polymers are polyethyleneimines, the polyamines, including di(higher alkyl)cyclic amines and their condensation products, polyamineamides, and their salts, and mixtures thereof. Preferred polymers for use in the fabric care compositions of the present invention are polyethyleneimines and their salts. Preferred polyethyleneimines have a molecular weight of less than about 2000, more preferably from about 200 to about 1500. The water solubility is preferably at least about 1 g/100 g water, more preferably at least about 3 g/100 g water, even more preferably at least about 5 g/100 g water.

Some polyamines with the general formula $(R^1)_2N(CX_2)_nN(R^2)_2$ can serve both as a chlorine scavenger and a "chelant" color care agent. Non-limiting examples of such preferred polyamines are N,N,N',N'-tetrakis(2-hydroxypropyl) ethylenediamine and N,N,N',N",N"-penta(2-hydroxypropyl) diethylenetriamine. Other suitable dual agents of this type are disclosed herein after in the Chelants section.

Chlorine scavengers for use in the solid fabric care compositions preferably are solid, e.g., water soluble amines, amine salts, and/or polymers. It is preferred that the chlorine scavenging amine-functional materials be neutralized by an acid, before they are added into the compositions. This neutralization actually converts the amines into ammonium salts. In the salt form, even simple amines and ammonia ($NH_3$) can be used. Preferred salts of this kind are the ammonium salts such as $NH_4Cl$, $(NH_4)_2SO_4$, and the like. Preferred polymeric chlorine scavengers have an average molecular weight of less than about 5,000, more preferably from about 200 to about 2,000, even more preferably from about 200 to about 1,000. Low molecular weight polymers are easier to remove from fabrics, resulting in less buildup of the chlorine scavenger and therefore less discoloration of the fabrics. The above chlorine scavenger is also suitable for use mixtures containing liquid fabric care actives with many of the preferred chlorine scavengers being at least partially water soluble.

2. Dye Transfer Inhibitors

Dye transfer inhibitors (DTI), such as polyvinyl pyrrolidone (PVP), appear to solubilize into the rinse and/or wash water to scavenge the free dye molecules, thus suspending the dyes and preventing them from redepositing onto fabrics. DTI may interact with some detergent actives and thus, it is preferable to provide DTI by adding them to the rinse bath solution, thus minimizing the interaction with surfactants.

The compositions of the present invention may contain an effective amount of polymeric dye transfer inhibiting agent (dye transfer inhibitor or DTI). An effective amount is typically an amount of DTI which will provide at least about 0.1 ppm, preferably from about 0.1 ppm to about 100 ppm, more preferably from about 0.2 ppm to about 20 ppm, in the subsequent wash or rinse liquor.

Suitable polymer DTIs are disclosed in WO 94/11482, published May 26, 1994, which is the same as copending, U.S. patent application of Trinh et al., Ser. No. 08/209,694, filed Mar. 10, 1994, for FABRIC SOFTENING COMPOSITIONS WITH DYE TRANSFER INHIBITORS FOR IMPROVED FABRIC APPEARANCE.

As disclosed in said application, dye transfer inhibitors useful in the present invention include water-soluble polymers containing nitrogen and oxygen atoms, selected from the group consisting of:

(1) polymers, which preferably are not enzymes, with one or more monomeric units containing at least one =N—C(=O)— group;

(2) polymers with one or more monomeric units containing at least one N-oxide group;

(3) polymers containing both =N—C(=O)— and N-oxide groups of (A) and (B); and (4) mixtures thereof;

wherein the nitrogen of the =N—C(=O)— group can be bonded to either one or two other atoms (i.e., can have two single bonds or one double bond).

Dye transfer inhibitors useful in the present invention include water-soluble polymers having the structure:

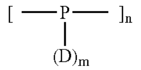

wherein each P is selected from homopolymerizable and copolymerizable moieties which attach to form the polymer backbone, preferably each P being selected from the group consisting of: vinyl moieties, e.g., [—C(R)$_2$—C(R)$_2$—]; other monomeric moieties, e.g., —[[C(R)$_2$]$_x$-L-], wherein each x is an integer from 1 to 6 and each L is independently selected from the group consisting of:

—N(R)—; —O—; —S—; —O—(O)C—; —C(O)—O—; —S(→O)—; —S(→O)$_2$—; —S(O)—O—; —O—(O)S—; —O—S(O)$_2$—O—;

—O—[Si(R$_2$)—O]$_p$—; —C(O)—; and —O—C(O)—O—; and DTI-active groups

—N(→O)(R)—; —N(R)C(O)—; —C(O)—N(R)— wherein each R is H, $C_{1-12}$ (preferably $C_{1-4}$) alkyl(ene), $C_6$–$C_{12}$ aryl(ene) and/or D, m is from 0 to 2, and p is from 1 to about 6; wherein each D contains moieties selected from the group consisting of: L moieties; structural moieties selected from the group consisting of linear and cyclic $C_{1-12}$ (preferably $C_{1-4}$) alkyl; $C_{1-12}$ alkylene; $C_{1-12}$ heterocyclic groups, which can also contain the DTI active groups; aromatic $C_{6-12}$ groups; and Rs to complete the group, wherein any linking groups which are attached to each other form linkages that are substantially stable under conditions of use; and wherein the nitrogen atoms can be attached to one, two, or three other atoms, the number of =N—C(O)— and/or ≡N→O groups present being sufficient to provide dye transfer inhibition, the total molecular weight being from about 500 to about 1,000,000, preferably from about 1,000 to about 500,000, n being selected to provide the indicated molecular weight, and the water solubility being at least about 100 ppm, preferably at least about 300 ppm, and more preferably at least about 1,000 ppm in water at ambient temperature of about 25° C.

a) Polymers with Active =N—C(=O)— Groups

The most common polymer of this type is polyvinyl pyrrolidone (PVP). PVP is commercially available from ISP, Wayne, N.J., and BASF Corp., Parsippany, N.J., as a powder or aqueous solutions in several viscosity grades, designated as, e.g., K-12, K-15, K-25, and K-30. These K-values indicate the viscosity average molecular weight, as follows: PVP Viscosity Avg. Mol. Wt.=2,500 (K-12); 10,000 (K-15); 24,000 (K-25); and 40,000 (K-30). PVP K-12, K-15, and K-30 are also available from Polysciences, Inc. Warrington, Pa., and PVP K-15, K-25, and K-30 and poly(2-ethyl-2-oxazoline) are available from Aldrich Chemical Co., Inc., Milwaukee, Wis.

The average molecular weight for water-soluble polymers with =N—C(=O)— groups useful in the present invention is from about 500 to about 100,000, preferably from about 500 to about 40,000, and more preferably from about 1,000 to about 30,000.

b) Polymers with Active N-Oxide Groups

Another useful group of polymeric DTI include water-soluble polymers containing active ≡N→O groups. The nitrogen of the ≡N→O group can be bonded to either one, two, or three other atoms.

One or more of the ≡N→O groups can be part of the pendant D group or one or more ≡N→O groups can be part of the polymerizable P unit or a combination of both.

Where the $\equiv N \rightarrow O$ group is part of the pendant D group, preferred D groups contain cyclic structures with the nitrogen atom of the $\equiv N \rightarrow O$ group being part of the ring or outside the ring. The ring in the D group may be saturated, unsaturated, or aromatic.

Examples of D groups containing the nitrogen atom of the $\equiv N \rightarrow O$ group include N-oxides of heterocyclic compounds such as the N-oxides of pyridine, pyrrole, imidazole, pyrazole, pyrazine, pyrimidine, pyridazine, piperidine, pyrrolidone, azolidine, morpholine, and derivatives thereof. A preferred dye transfer inhibitor is poly(4-vinylpyridine N-oxide) (PVNO). Examples of D groups with the nitrogen atom of the $\equiv N \rightarrow O$ group being outside the ring include aniline oxide and N-substituted aniline oxides.

An example of a polymer wherein the $\equiv N \rightarrow O$ group is part of the monomeric P backbone group is polyethyleneimine N-oxide.

Mixtures of these groups can be present in the polymeric DTIs of (2) and (3).

The amine N-oxide polymers of the present invention typically have a ratio of amine N-oxide to the amine of from about 1:0 to about 1:2. The amount of amine oxide groups present in the polyamine oxide polymer can be varied by appropriate copolymerization or by appropriate degree of N-oxidation. Preferably, the ratio of amine N-oxide to amine is from about 1:0 to about 1:1, most preferred from 1:0 to about 3:1.

The amine oxide unit of the polyamine N-oxides has a PKa of $\leqq 10$, preferably PKa$\leqq 7$, more preferably PKa$\leqq 6$.

The average molecular weight of (2) useful in the present invention is from about 500 to about 1,000,000; more preferably from about 1,000 to about 500,000; most preferably from about 2,000 to about 100,000.

Any polymer backbone above can be used in (1) or (2) as long as the polymer formed is water soluble and has dye transfer inhibiting properties. Examples of suitable polymeric backbones are polyvinyls, polyalkylenes, polyesters, polyethers, polyamide, polyimides, polyacrylates, and copolymers and block copolymers thereof, and mixtures thereof.

c) Copolymers Including Active $=N—C(=O)—$ and/or $\equiv N \rightarrow O$ Groups Effective polymeric DTI agents can include those formed by copolymerizing mixtures of monomeric, oligomeric, and/or polymeric units containing active $=N—C(=O)—$ and/or active $\equiv N \rightarrow O$ groups (e.g., copolymers and/or block copolymers of PVP and PVNO). Other suitable DTI copolymers include those in which an effective amount of monomeric, oligomeric, and/or polymeric units containing active $=N—C(=O)—$ groups and/or active $\equiv N \rightarrow O$ groups is copolymerized with "filler" monomeric, oligomeric, and/or polymeric units which do not contain active $=N—C(=O)—$ or $\equiv N \rightarrow O$ groups but which impart other desirable properties to the DTI copolymer, such as increased water solubility or enhanced fabric substantivity [e.g., block copolymer of PVP ($\geqq$ about 60%) and polyvinylimidazole].

Some of the preferred dye transfer inhibitors are fairly water soluble. When these dye transfer inhibitors are present in the compositions of the present invention, the softener composition's dissolution rate criterion (as defined herein before) is determined with the composition not containing the dye transfer inhibitors.

3. Dye Fixatives

Dye fixatives are similar to dye transfer inhibitors, but tend to be more water insoluble. They act primarily by inhibiting removal of the dye rather than intercepting it in the water phase and keeping it suspended like the dye transfer inhibitors.

Suitable dye fixatives are disclosed in U.S. Pat. No. 5,632,781, Shinichi et al., issued May 27, 1997; U.S. Pat. No. 4,583,989, Toshio et al., issued Apr. 22, 1986; U.S. Pat. No. 3,957,574, Edward, issued May 18, 1975; U.S. Pat. No. 3,957,427, Chambers, issued May 18, 1976; and U.S. Pat. No. 3,940,247, Derwin et al., issued Feb. 24, 1976.

4. Chelants

The compositions may also comprise a "chelant" color care agent, preferably color care agent having the formula:

$$(R^1)_2N(CX_2)_nN(R^2)_2$$

wherein each X is selected from the group consisting of hydrogen (preferred), linear or branched, substituted or unsubstituted alkyl groups having from 1 to about 10 (preferably 1 or 2) carbons atoms and substituted or unsubstituted aryl having at least 6 carbon atoms (preferably from 6 to about 22), and mixtures thereof; n is an integer from 0 to 6, preferably 2 or 3; each $R^1$ and $R^2$ is independently selected from the group consisting of hydrogen; alkyl; aryl; alkaryl; aralkyl; hydroxyalkyl; polyhydroxyalkyl; $C_{1-10}$, preferably $C_{2-3}$, alkyl groups substituted with one (preferred), or more (preferably 2 or 3) carboxylic acid or phosphonic acid groups, or salts thereof; polyalkylether having the formula $—((CH_2)_yO)_zR^3$ where each $R^3$ is hydrogen (preferred) or a linear, branched, substituted or unsubstituted alkyl chain having from 1 to about 10 (preferably from about 1 to about 4) carbon atoms and where y is an integer from 2 to about 10 (preferably 2 or 3) and z is an integer from 1 to 30 (preferably from 2 to about 5); the group $—C(O)R^4$ where each $R^4$ is selected from the alkyl; alkaryl; aralkyl; hydroxyalkyl; polyhydroxyalkyl, polyalkylether, and alkyl groups substituted with one (preferred), or more (preferably 2 or 3) carboxylic acid or phosphonic acid groups, or salts thereof as defined in $R^1$ and $R^2$; and $—CX_2CX_2N(R^5)_2$ with no more than one of $R^1$ and $R^2$ being $CX_2CX_2N(R^5)_2$ and wherein each $R^5$ is selected from the alkyl; alkaryl; aralkyl; hydroxyalkyl; polyhydroxyalkyl, polyalkylether, and alkyl groups substituted with one (preferred), or more (preferably 2 or 3) carboxylic acid or phosphonic acid groups, or salts thereof as defined in $R^1$ and $R^2$; and one $R^1$ and one $R^2$ can combine to form a cyclic compound.

The available alkyl groups include linear or branched, substituted or unsubstituted alkyl groups typically having from about 1 to about 22 carbon atoms, preferably from about 1 to about 10 carbon atoms. Most preferred alkyl groups include methyl, ethyl, propyl, isopropyl, and mixtures thereof. The available aryl groups include substituted or unsubstituted aryl groups typically having from 6 to about 22 carbon atoms. Substitutions can include alkyl chains as earlier described thereby providing alkaryl or aralkyl groups having from about 6 to about 22 carbon atoms. Preferred aryl, aralkyl and alkaryl groups include phenyl, benzyl and mesityl. The available hydroxyalkyl and polyhydroxyalkyl groups include linear or branched, hydroxy substituted groups typically having from 1 to about 22 carbon atoms. Preferred groups include hydroxymethyl, hydroxyethyl, 1-hydroxypropyl and 2-hydroxypropyl. The available polyalkoxy (polyalkylether) groups include those having the formula: $—((CH_2)_yO)_zR^3$ wherein the integer y typically ranges from 2 to about 10 with 2 and 3 the most preferred; the group $—(CH_2)_y—$ can include both linear and branched chains; preferred groups include ethoxy and isopropoxy groups; the integer z typically ranges from about 1 to about 30 with lower levels of alkoxylation, preferably ethoxylation, being preferred; $R^3$ is typically hydrogen or an alkyl groups having 1 to 5 carbon atoms. The group —C(O)$R^4$ can also be employed where $R^4$ is alkyl; alkaryl; aralkyl; hydroxyalkyl; polyhydroxyalkyl, polyalkylether, carboxylic acid, alkyl dicarboxylic acid, phosphonic acid, alkyl phosphonic acid as defined above, and mixtures thereof.

Remaining $R^1$ and $R^2$ possibilities include linear or branched alkyl carboxylic acid groups and water soluble salts thereof having the general formula $—(CH_p(R^7)_q)_t C(O)O^{(-)}\text{-}M^{(+)}$ wherein t is an integer from 1 to about 5, p is an integer from 1 to 3, p+q=2 and $M^{(+)}$ is a water soluble monovalent cation such as hydrogen, alkali metal, etc. As t typically ranges from about 1 to about 5, the total number of carbons typically does not exceed 6 and $M^{(+)}$ is a water soluble cation such as alkali metal or other available groups such as ammonium or substituted ammonium. Also available are dicarboxylic acid groups, including the water soluble salts, which have from about 2 to about 5 carbons atoms, and linear, branched or polyfunctional substituted branched alkyldicarboxylic acids and water soluble salts thereof also having from about 2 to about 5 carbon atoms. Preferred carboxylate chelants include ethylenediaminetetraacetic acid (EDTA), N-hydroxyethylethylenediamintriacetic acid, nitrilotriacetic acid (NTA), ethylenediamine tetraproprionic acid, ethylenediamine-N,N'-diglutamic acid, 2-hydroxypropylenediamine-N,N'-disuccinic acid, triethylenetetraaminehexaacetic acid, diethylenetriaminepentaacetic acid (DETPA), and ethanoldiglycines, including their water-soluble salts such as the alkali metal, ammonium, and substituted ammonium salts thereof, and mixtures thereof Phosphonic acid chelants and water soluble salts thereof and linear, branched or polyfunctional substituted branched alkylphosphonic acids and water soluble salts thereof can be employed as $R^1$ and $R^2$. In both cases, the number of carbon atoms typically ranges from about 1 to about 5. Preferred groups include ethylenediaminetetrakis (methylenephosphonic acid), diethylenetriamine-N,N,N',N",N"-pentakis (methane phosphonic acid) (DETMP) and 1-hydroxyethane-1,1-diphosphonic acid (HEDP), including their water-soluble salts such as the alkali metal, ammonium, and substituted ammonium salts thereof, and mixtures thereof.

$R^1$ and $R^2$ can also be the group $CX_2CX_2N(R^5)_2$. However, when the group is present, no more than one of $R^1$ and $R^2$ at any one time can be the group $CX_2CX_2N(R^5)_2$. Furthermore, each $R^5$ can be alkyl; alkaryl; aralkyl; hydroxyalkyl; polyhydroxyalkyl, polyalkylether, alkoxy, polyalkoxy alkyl carboxylic acid, alkyl dicarboxylic acid, phosphonic acid and alkyl phosphonic acid as defined above for $R^1$ and $R^2$. Preferably, when any one of $R^1$ and $R^2$ is present as the group $CX_2CX_2N(R^5)_2$, then each $R^5$ is preferably, alkyl or hydroxyalkyl group as defined above. Additionally, either of $R^1$ and of $R^2$ can combine to form a cyclic substituent. Suitable examples include the moiety:

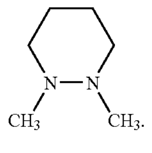

To provide suitable color care properties, the preferred color care chelants consist of at least about 3% by weight of the compound of nitrogen, preferably at least about 7% and more preferably at least about 9%. The preferred color care chelants have a total number of carbon atoms in the groups $R^1$ and $R^2$ of about 50 or less, more preferably of about 40 or less and more preferably of about 20 or less.

Most preferably, each $R^1$ and $R^2$ is independently selected from the group consisting of hydrogen, linear alkyl groups having from 1 to 5 carbon atoms and linear hydroxyalkyl groups having from 1 to 5 carbon atoms. Especially preferred are the groups ethyl, methyl, hydroxyethyl, hydroxypropyl, and mixtures thereof. While each of $R^1$ and $R^2$ can be individually selected, the preferred color care component according to the present invention involves the situation wherein each of $R^1$ and $R^2$ is hydroxyalkyl group having from 1 to 5 carbon atoms. A preferred list of chelants includes N,N,N',N'-tetraethylethylenediamine, 2-{[2-(dimethylamino)ethyl]-methylamino}ethanol, bis-(2-hydroxyethyl)N,N'-dimethylethylenediamine, bis(octyl)-N,N'-dimethylethylenediamine, N,N,N'N'-tetrakis(2-hydroxypropyl) ethylenediamine, N,N,N',N",N"-penta(2-hydroxypropyl) diethlyenetriamine, N,N'-diethylethyldiamine, N,N,N'-trimethylethylenediamine, 1,3-pentadiamine, N,N-dimethylethylenediamine, 2-(2-aminoethylamino)ethanol, N,N'-dimethylethylenediamine, 1,3-diamino-2-hydroxypropane, N'-methyl-2,2'-diaminodiethylamine, N-(2-aminoethyl)-1,3-propanediamine. Particularly preferred are N,N,N',N'-tetrakis(2-hydroxypropyl)ethylenediamine and N,N,N',N",N"-penta(2-hydroxypropyl)diethylenetriamine. Such materials are commercially available from a number of sources including BASF of Washington, N.J. under the tradename QUADROL and PENTROL.

These compounds are believed to provide protection as chelants and are preferred. However, other chelants can also be used, so long as they are compatible and can bind with metals that cause hue shifts in fabric dyes. Other suitable chelants are described in the copending allowed U.S. patent application of Rusche et al., Ser. No. 08/753,167, filed Nov. 25, 1996 for CHELATING AGENTS FOR IMPROVED COLOR FIDELITY.

These chelants (which as used herein also includes materials effective not only for binding metals in solution but also those effective for precipitating metals from solution) include citric acid, citrate salts (e.g., trisodium citrate), isopropyl citrate, 1-hydroxyethylidene-1,1-diphosphonic acid (etidronic acid), available from Monsanto as Dequest RTM 2010, 4,5-dihydroxy-m-benzene-sulfonic acid/sodium salt, available from Kodak as Tiron RTM, diethylenetriaminepentaacetic acid, available from Aldrich, ethylene diaminetetraacetic acid (EDTA), ethylene diamine-N,N'-disuccinic acid (EDDS, preferably the S, S isomer), 8-hydroxyquinoline, sodium dithiocarbamate, sodium tetraphenylboron, ammonium nitrosophenyl hydroxylamine, and mixtures thereof. Most preferred of these chelants are EDTA and especially citric acid and citrate salts.

The compositions and articles herein may also contain one or more iron and/or manganese chelating agents. Such chelating agents can be selected from the group consisting of amino carboxylates, amino phosphonates, polyfunctionally-substituted aromatic chelating agents and mixtures therein, all as hereinafter defined. Without intending to be bound by theory, it is believed that the benefit of these materials is due in part to their exceptional ability to remove iron and manganese ions from washing solutions by formation of soluble chelates. In some cases, a conventional chelant in the laundry wash product may function in part to "regenerate" the fabric substantive chelants. This is accomplished when the heavy metal chelant while remaining adsorbed to the fabric surface, exchanges any presently bound heavy metal ion to a conventional chelant. The metal exchanged is carried away with the conventional metal chelant, while the heavy metal chelant is substantively held on the fabric, free to chelate a new metal ion (i.e., in a subsequent rinse cycle).

Amino carboxylates useful as chelating agents include ethylenediaminetetracetates, N-hydroxyethylethylenediaminetriacetates, nitrilotriacetates, ethylenediamine tetraproprionates, triethylenetetraaminehexacetates, diethylenetriaminepentaacetates, and ethanoldiglycines, alkali metal, ammonium, and substituted ammonium salts therein and mixtures therein.

Amino phosphonates are also suitable for use as chelating agents in the compositions of the invention when at least low levels of total phosphorus are permitted in detergent compositions, and include ethylenediaminetetrakis (methylenephosphonates) as DEQUEST. Preferred, these amino phosphonates to not contain alkyl or alkenyl groups with more than about 6 carbon atoms.

Polyfunctionally-substituted aromatic chelating agents are also useful in the compositions herein, as described in U.S. Pat. No. 3,812,044, issued May 21, 1974, to Connor et al. Preferred compounds of this type in acid form are dihydroxydisulfobenzenes such as 1,2-dihydroxy-3,5-disulfobenzene.

A preferred biodegradable chelator for use herein is ethylenediamine disuccinate ("EDDS"), especially the [S,S] isomer, as described in U.S. Pat. No. 4,704,233, Nov. 3, 1987, to Hartman and Perkins.

I. Color Maintenance Agents

The compositions and articles of the present invention may also comprise color maintenance agents that provide for increased color protection for both white and colored fabrics. The dinginess and yellow cast that develops on white fabrics is reduced while the color fading and changing of color-hue of dyed fabrics are marginalized.

Modified polyamines may be used as color maintenance agents to chelate heavy metal ions in the laundry liquor, that might otherwise contribute significantly to both the yellowing of white fabrics and the fading or change of hue of colored materials. Heavy metal ions, such as copper, chelate with dye molecules creating a perturbation and change in the absorption spectrum of these molecules. Although by this process no dye molecules are lost, the result of this chelation is a change of hue or a dimming or loss of intensity to the color of the fabric. Preventing the association of these heavy metal ions to the fabric dye molecules results in a reduction of fabric hue changing or color fading.

The use of an article containing conventional chelants is particularly desirable in the rinse bath solution where chelants that were included with the detergent composition are generally washed from the fabrics and additional heavy metal ions are introduced through the rinse water. Further, the use of heavy metal chelants that will deposit onto fabrics and slowly release during subsequent exposures to laundry cycles is preferred. These chelants will include modified polyamines, especially polyalkyleneimines, that have less than 100% of their nitrogen moieties modified, that is about 0.5% to 90% of their nitrogen moieties modified. The modifying groups are polyalkoxylates such as ethoxylates or carboxylate-related moieties. Chelant compounds that are modified by attachment of polyalkoxylate moieties to the polyamines are in general highly effective against the heavy metal ions responsible for color fidelity problems (e.g., copper), while the polyamines modified for use by attachment of carboxylate moieties are superior in their protection against ions (e.g., manganese) that effect the dinginess of white fabrics and in addition are still highly effective against heavy metals responsible for color fidelity problems.

Therefore, the present invention relates to fabric care compositions comprising water soluble or dispersible heavy metal ion control agents comprising:

i) a modified polyamine having a backbone of the formula

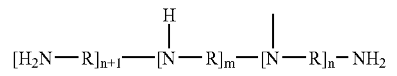

wherein R is $C_2$–$C_{22}$ alkylene, $C_3$–$C_{22}$ alkyl substituted alkylene, $—CH_2CH(OH)CH_2—$, $—(R^1O)_xR^1—$, $—CH_2CH(OH)CH_2O(R^1O)_x$, $—CH_2CH(OH)CH_2—$, and mixtures thereof; and ii) from 0.5% to 90% of the polyamine backbone —NH units are substituted by units independently selected from:

a) units having the formula $$—(CH_2CH(OH)CH_2O)_w(R^1O)_xR^2$$

wherein $R^1$ is $C_2$–$C_6$ alkylene, $C_3$–$C_6$ alkyl substituted alkylene, and mixtures thereof; $R^2$ is hydrogen, $_1$–$C_{22}$ alkyl, and mixtures thereof;

b) units having the formula $$—CR^3R^4R^5$$

wherein each $R^3$, $R^4$, and $R^5$ is independently selected from the group consisting of hydrogen, $—(CH_2)_y(L)_zR^6$, and mixtures thereof provided that one $R^3$, $R^4$, or $R^5$ is not a hydrogen atom, wherein $R^6$ is $—CO_2H$, $—C(NH)NH_2$, $—CH(CO_2H)CH_2CO_2H$, $—C(SH)S$, $—C(O)NHOH$, $—C(NOH)NH_2$, $—CH_2P(O)(OH)_2$, $—OP(O)(OH)_2$, and mixtures thereof; L is —NH—, —S—, and mixtures thereof; and c) units having the formula $—C(O)CH_2N(CH_2CO_2H)_2$, $—C(O)CH_2N(CH_2CO_2H)CH_2CH_2N(CH_2CO_2H)_2$, $—(CH_2)_pCH(CO_2H)N(CH_2CO_2H)_2$, and mixtures thereof; and wherein m is from 2 to about 700, n is from 0 to about 350, p is from 1 to 20, w is 0 or 1, x is from 1 to 100, y is from 0 to 3, z is 0 or 1 as well as a method for protecting dyed or colored fabric from fading and white fabric from developing dinginess.

The heavy metal ion control agents of the present invention comprise a modified polyamine backbone of the formula

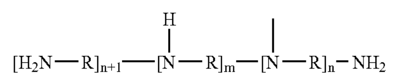

wherein the value of m is from 2 to about 700 and the value of n is from 0 to about 350. Preferably the compounds of the present invention comprise polyamines having a ratio of m to n that is at least 1:1 but may include linear polymers (n equal to 0) as well as a range as high as 10:1, preferably the ratio is 2:1. When the ratio of m to n is 2:1, the ratio of primary to secondary to tertiary amine moieties, that is the ratio of $—RNH_2$, —RNH, and —RN moieties, is 1:2:1.

R units are $C_2$–$C_6$ alkylene, $C_3$–$C_{22}$ alkyl substituted alkylene, $—CH_2—CH(OH)CH_2—$, $—(R^1O)_xR^1—$, $—CH_2CH(OH)CH_2O(R^1O)_xCH_2CH(OH)CH_2—$, and mixtures thereof, preferably ethylene, 1,2-propylene, 1,3-propylene, and mixtures thereof, more preferably ethylene. R units serve to connect the amine nitrogens of the backbone.

The preferred heavy metal chelating agents of the present invention comprise polyamine backbones wherein less than 50% of the R groups comprise more than 3 carbon atoms. The use of two and three carbon spacers as R moieties between nitrogen atoms in the backbone is advantageous for controlling the chelation properties of the molecules, whereas inclusion of longer chain length spacers, and spacers other than alkylene moieties, are advantageous for controlling properties such as substantivity and molecular weight. For example, ethylene, 1,2-propylene, and 1,3-propylene comprise 3 or less carbon atoms and compositions of the present invention can comprise any amount of these three moieties in excess of 50%. For the preferred embodiments of the present invention moieties such as $-(R^1O)_xR^1-$, and $-CH_2CH(OH)CH_2O(R^1O)_xR^1CH_2CH(OH)CH_2-$ cannot comprise 50% or more of the R moieties present in the polymer backbone. More preferably the compositions of the present invention comprise less than 25% moieties having more than 3 carbon atoms. Most preferred backbones comprise less than 10% moieties having more than 3 carbon atoms.

The heavy metal chelants of the present invention comprise homogeneous or non-homogeneous polyamine backbones. For the purpose of the present invention the term "homogeneous polyamine backbone" is defined as a polyamine backbone having R units that are the same (i.e., all ethylene). However, this sameness definition does not exclude polyamines that comprise other extraneous units comprising the polymer backbone and that are present due to an artifact of the chosen method of chemical synthesis. For example, it is known to those skilled in the art that ethanolamine may be used as an "initiator" in the synthesis of polyethyleneimines, therefore a sample of polyethyleneimine that comprises one hydroxyethyl moiety resulting from the polymerization "initiator" would be considered to comprise a homogeneous polyamine backbone for the purposes of the present invention.

For the purposes of the present invention the term "non-homogeneous polymer backbone" refers to polyamine backbones that are a composite of shorter chained polyamines that are coupled with suitable "chain elongation moieties". The proper manipulation of these "chain elongation moieties" provides the formulator with the ability to change the solubility and substantivity of the heavy metal ion control agents of the present invention. Examples of these "chain elongation moieties" are $C_4$–$C_{22}$ alkyl substituted alkylene, $-CH_2-CH(OH)CH_2-$, $-(R^1O)_xR^1-$, $-CH_2CH(OH)CH_2O(R^1O)_xCH_2CH(OH)CH_2-$, preferably $-CH_2-CH(OH)CH_2-$, $-(R^1O)_xR^1-$, $-CH_2CH(OH)CH_2O(R^1O)_xCH_2CH(OH)CH_2-$, however this list is not meant to be totally inclusive of those moieties suitable for use in the present invention.

However, not all of the preferred heavy metal ion controlling agents comprise backbones that include a "chain elongation moiety". The preferred polyamines that comprise the backbone of the compounds are generally polyalkyleneamines (PAA's), polyalkyleneimines (PAI's), preferably polyethyleneamine (PEA's), polyethyleneimines (PEI's), or PEA's or PEI's connected by moieties having longer R units than the parent PAA's, PAI's, PEA's or PEI's. A common polyalkyleneamine (PAA) is tetrabutylenepentamine. PEA's are obtained by reactions involving ammonia and ethylene dichloride, followed by fractional distillation. The common PEA's obtained are triethylenetetramine (TETA) and teraethylenepentamine (TEPA). Above the pentamines, i.e., the hexamines, heptamines, octamines and possibly nonamines, the cogenerically derived mixture does not appear to separate by distillation and can include other materials such as cyclic amines and particularly piperazines. There can also be present cyclic amines with side chains in which nitrogen atoms appear. See U.S. Pat. No. 2,792,372, Dickinson, issued May 14, 1957, which describes the preparation of PEA's.

The PEI's which comprise the preferred backbones of the polyamines of the present invention can be prepared, for example, by polymerizing ethyleneimine in the presence of a catalyst such as carbon dioxide, sodium bisulfite, sulfuric acid, hydrogen peroxide, hydrochloric acid, acetic acid, etc. Specific methods for preparing PEI's are disclosed in U.S. Pat. No. 2,182,306, Ulrich et al., issued Dec. No. 5, 1939; U.S. Pat. No. 3,033,746, Mayle et al., issued May 8, 1962; U.S. Pat. No. 2,208,095, Esselmann et al., issued Jul. 16, 1940; U.S. Pat. No. 2,806,839, Crowther, issued Sep. 17, 1957; and U.S. Pat. No. 2,553,696, Wilson, issued May 21, 1951 (all herein incorporated by reference). In addition to the linear and branched PEI's, cyclic amines that are typically formed as artifacts of synthesis may also be included. The presence of these materials may be increased or decreased depending on the conditions chosen by the formulator.

The polyamines of the present invention may develop undesirable off-colors due to impurities present as artifacts of their preparation, processing or handling. In the case where the presence of color is unacceptable in the final formulation, the processor or formulator may apply one or more known procedures for "de-colorizing" the polyamines of the present invention. For instance, treatment with activated charcoal in the presence of a suitable solvent is a common procedure for de-colorizing organic materials and may be applied to polyamines. Further, contact with silicates or diatomaceous earth are additional de-colorizing measures. Treatment with bleaching agents (e.g., hypohalites or peracids) also serves as a suitable method for de-colorizing the chelants of the present invention provided that once de-colorizing with a bleaching agent is accomplished, the formulator insures that little or no active bleaching agent is carried through to the formulation, as described in detail hereinafter. De-colorizing by any of these methods may be accomplished at any stage in the processing of the polyamines disclosed herein, provided said processing does not limit or diminish the effectiveness of the final heavy metal ion control agents.

The amine units of the polyamine backbone are substituted by one or more independently selected moieties further described herein below. Each nitrogen atom of the backbone having a hydrogen atom is a potential site of substitution. Primary amines, $-NH_2$, have two sites of substitution, secondary amines, $-NH-$, have one site of substitution, while tertiary amines, $-N-$, comprising the polyamine backbone have no sites of substitution. The percentage of the total $-NH$ sites that are preferably substituted are from 0.5% to less than about 90%, more preferably from 0.5% to less than about 50%, yet more preferably from about 0.5% to less than about 45%, most preferably 0.5% to less than about 25%. The substituents may comprise moieties that are all identical or that are a mixture selected from the moieties described further herein below.

However, prior to substitution, some polyamine backbones may comprise a "chain elongation moiety", for example:

$$-CH_2CH(OH)CH_2O(R^1O)_xCH_2CH(OH)CH_2-$$

wherein two free hydroxyl moieties ($-OH$) are available to undergo substitution under some of the same chemical conditions that are used to substitute one or all of the $-NH$ units. When calculating the degree of backbone substitution (per cent of backbone substitution) these hydroxyl moieties will be included for calculation purposes if the substituting moieties will react with the —OH moieties as well as the $-NH_2$ and —NH moieties of the backbone. The hydroxyl groups are excluded from this calculation if the process used by the formulator restricts in some manner the reactivity of said hydroxyl moieties (such as use of an —OH protecting group or alkylation without the presence of strong base).

N—H Substituent Groups: Moieties used to Modify the Polyamine Backbone

The substituent groups of the present invention comprise polyoxyalkyleneoxy moieties that are either capped or uncapped, and carboxylate-like or carboxylate-derived moieties.

Substituents according to the present invention having the formula $$-(CH_2CH(OH)CH_2)_w(R^1O)_xR^2$$

are polyoxyalkyleneoxy moieties, wherein $R^1$ units are $C_2$–$C_6$ alkylene, $C_3$–$C_6$ substituted alkylene, preferably ethylene, 1,2-propylene, and 1,3-propylene, more preferably ethylene. $R^2$ units are hydrogen, or $C_1$–$C_{22}$ alkyl, preferably hydrogen or $C_1$–$C_4$ alkyl, more preferably hydrogen or methyl. The index w is 0 or 1; the index x is from 1 to about 100, preferably 1 to about 50, more preferably 1 to about 25, most preferably from about 3 to about 20.

Substituents according to the present invention having the formula $$-CR^3R^4R^5$$

are carboxylate-derived or carboxylate-like moieties, wherein each $R^3$, $R^4$, and $R^5$ is independently selected from the group consisting of hydrogen, $-(CH_2)_y(L)_zR^6$, and mixtures thereof, provided that at least one $R^3$, $R^4$, or $R^5$ is not a hydrogen atom. $R^6$ units are $-CO_2H$, $-C(NH)NH_2$, $-CH(CO_2H)CH_2CO_2H$, —C(SH)S, —C(OH)NOH, $-C(NOH)NH_2$, $-CH_2P(O)(OH)_2$, $-OP(O)(OH)_2$, and mixtures thereof, preferably $-CO_2H$. L is —NH—, —S—, or mixtures thereof, preferred L is —NH— when $R^6$ units are $-C(NH)NH_2$ or $-CH_2P(O)(OH)_2$. The value of the index y is from 0 to 3, preferably 0 or 1. The value of the index z is 0 or 1. The index z is 0 when $R^6$ comprises $-CO_2H$.

Preferred —NH substituents are carboxylate-like or carboxylate-derived moieties of the formula $$-CR^3R^4R^5$$

wherein at least two of the $R^3$, $R^4$, and $R^5$ units are substituted by $-(CH_2)_y(L)_zR^6$ having the formula

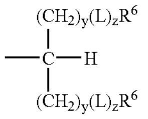

or all three of the $R^3$, $R^4$, and $R^5$ units are substituted by $-(CH^2)_y(L)_zR^6$ having the formula

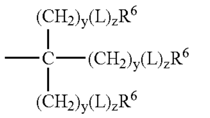

and each $R^6$ can comprise the same or different units, and each y and z car, assume different values. More preferred are the moieties having the formula

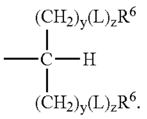

For the purposes of the present invention, when the —NH substituents are $-CR^3R^4R^5$ moieties, all of the $R^3$, $R^4$, and $R^5$ units cannot comprise a hydrogen atom, that is $-CR^3R^4R^5$ cannot be a methyl group.

For the purposes of the present invention the term "carboxylate derived moieties or carboxylate-like moieties" are defined as those units that either contain a carboxylate moiety (e.g., $-CO_2H$), units that comprise an $sp^2$ hybrid carbon atom bonded to an atom other than oxygen (e.g., $-C(NH)NH_2$) or units having an atom other than carbon doubly bonded to oxygen or to another more electronegative atom capable of forming a heavy metal chelate (e.g., the P=O bond of $-CH_2P(O)(OH)_2$).

Other suitable units for substitution onto the polyamine backbone are carboxylate containing units having the formula $-C(O)CH_2N(CH_2CO_2H)_2$, $-C(O)CH_2N(CH_2CO_2H)CH_2CH_2N(CH_2CO_2H)_2$, $-(CH_2)_pCH(CO_2H)N-(CH_2CO_2H)_2$, and mixtures thereof, wherein p is from 1 to 20.

Examples or preferred substituents according to the present invention having the formula $$-CR^3R^4R^5$$

that are derivatives of carboxylates are succinic acids, diacetic acids, triacetic acids, dipruprionic acids, amidines, thioureas, guanidines, dithiocarbamates, hydroxamic acids, amidoximes, and the like, although this list is not meant to be inclusive. Examples of most preferred carboxylate derived moieties or carboxylate-like moieties of the present invention include di-carboxylic acids having the formulas

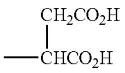 , 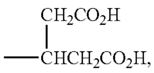 , 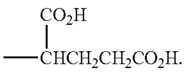

Examples of preferred carboxylate derived units or units "having an atom other than carbon doubly bonded to oxygen or to another more electronegative atom" have the formulas

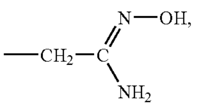 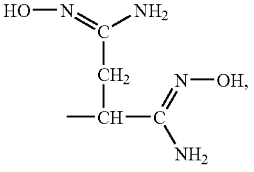

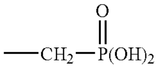

wherein combinations of the aforementioned moieties or any other carboxylate or carboxylate derived moiety are suitable for use in the present invention, for example, mixed moieties having the formula

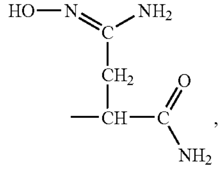,

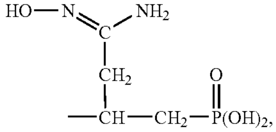,

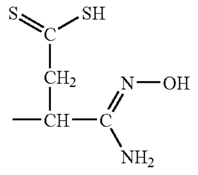

Determination of the Amount of the Total —NH Equivalents that are Substituted In general, the polyamines of the present invention will have a ratio of primary amine: secondary amine:tertiary amine of about 1:2:1, that is the starting polyamines having the general formula

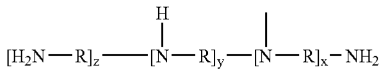

wherein R is the same as defined herein above, and generally have the indices x, y, and z represent the number of tertiary, secondary and primary amino moieties in the backbone. In general, the preferred ratio or x, y and z is the ratio of 1:2:1. The indices x, y, and z relate to the ratio of primary, secondary, and tertiary nitrogens present in the polyamine backbone and are not related to the relative ratio of moieties that comprise R units. For most cases, however, it is convenient to describe the polyamines of the present invention as having the general structure

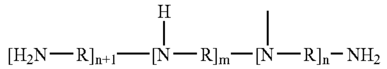

wherein preferably the value of m to n is 2:1, each R can be the same or different moiety, that is the backbone may be "homogeneous" or "non-homogeneous" as is further defined herein above.

The method for calculating "from about 0.5% to about 90% of the total polyamine backbone N—H equivalents" is defined as follows. Each hydrogen atom attached to each nitrogen atom of the backbone represents an active site for subsequent substitution (except for the case as described herein above wherein the backbone R unit comprises a substitutable —OH moiety). Therefore any —NH function capable of being substituted is considered one equivalent. Primary amine moieties, $—NH_2$, comprise two mole equivalents of —NH moieties and secondary amine moieties, —NH, comprise one mole equivalent of —NH moieties.

Preferred examples of the heavy metal ion chelants of the present invention comprise substituted polyamines wherein the polyamine backbones comprise polyethyleneimines (R is ethylene) and the substituent groups are partially selected from the polyoxyalkyleneoxy substituents and partially from the carboxylate-derived or carboxylate-like moieties.

The heavy metal chelating agents of the present invention may also consist of R units which comprise more than three carbon atoms. Backbones of this type may be prepared by coupling one or more substituted or un-substituted polyamines to form a longer "non-homogeneous" backbone. For example, as depicted in the scheme below, two moles of a shorter chain polyamine are reacted with four moles of a methyl capped polyethyleneglycol synthon, $CH_3(OCH_2CH_2)_4Cl$, to form a substituted polyamine subunit. The two shorter chain substituted polyamine subunits are then coupled to form a heavy metal chelant having a non-homogeneous backbone.

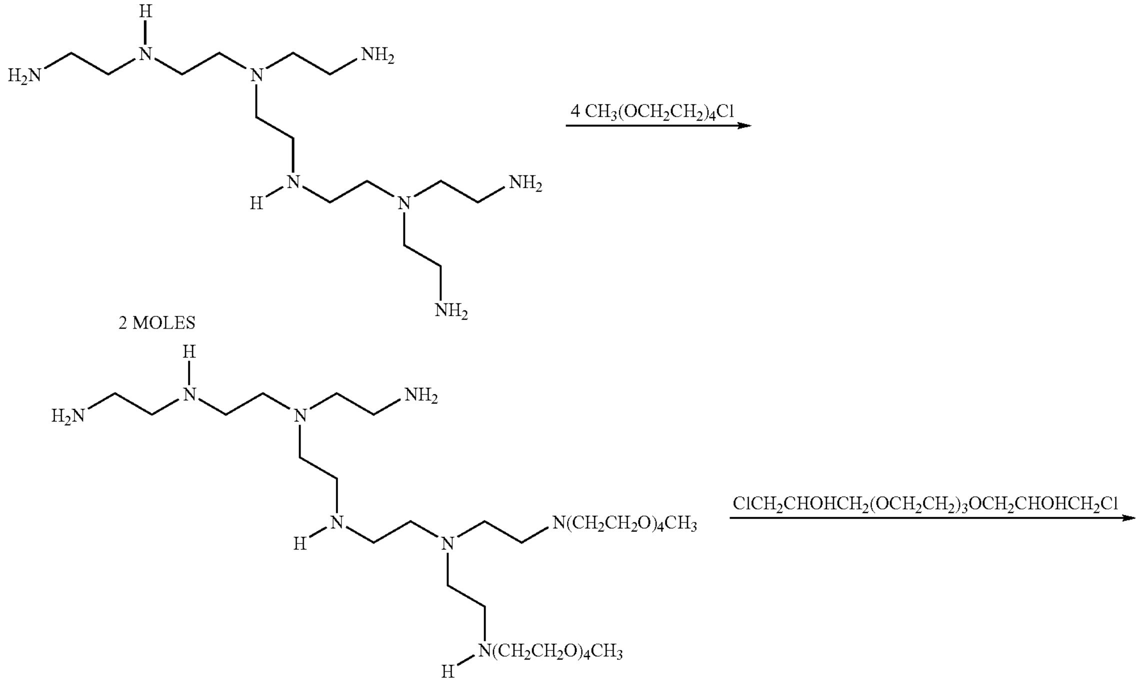

-continued

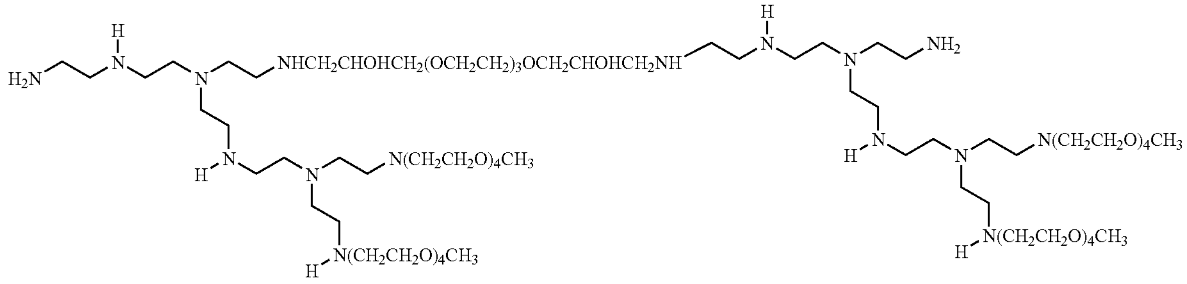

The heavy metal ion control agents of the present invention have the ability to chelate heavy metal ions responsible for the fading or change the hue of dyed fabric as well as limiting the build-up of dingy/yellowness that pervades white fabrics after successive laundering. Important to providing this chelant effect is the substantivity for fabric displayed by the compositions of the present invention. The formulator can manipulate the R units to provide an agent having a substantivity targeted to the specific usage of the composition. For example, the materials of the present invention remain on the fabric after initial application and are then gradually desorbed during successive aqueous exposures not comprising chelant. The formulator, employing the substantive nature of these compounds of the present invention can therefore formulate a laundry pre-soak composition which will protect fabrics that may be repeatedly exposed to heavy metal ions between treatments with suitable chelators.

The composition of water supplies varies from geographic location to location and the formulator by varying the substituents as well as the backbone R units is able to prepare chelants that may be targeted to more or less harsh heavy metal ion concentrations. Further. the compounds of the present invention may be useful for scavenging excess positive halogen species introduced via commercial water supply systems. The compositions and articles of the present invention containing color maintenance agents may be added via the rinse cycle alone or when fabric softener or other adjunct ingredients are present in the rinse bath.

The fabric care compositions of the present invention typically comprise at least about 0.001% by weight of the color maintenance or heavy metal ion control agent, preferably from about 0.001% to about 5%, more preferably from about 0.1% to about 2%, most preferably from about 0.1% to about 1%.

These additive compositions provide the consumer with a method for protecting dyed or colored fabric from metal ion induced fading and white fabric from developing dinginess. When the heavy metal control agents according to the present invention are present in a aqueous solution of at least 0.5 ppm, preferably at least 1 ppm, more preferably from about 2 ppm to about 100 ppm, most preferably from about 2 ppm to about 50 ppm, contacting fabric with this solution for a sufficient time provides protection against fading and dinginess.

For the purposes of the present invention the term "dinginess" is the development on white fabric of a gray or yellow cast that results from the interaction of heavy metal with the fabric or the body soils present. "Dinginess" can be measured by objective human grading and recorded in calibrated units, for example, in Panel Score Units (PSU) or can be measured by instrumentation known by those skilled in the art.

For the purposes of the present invention the term "contacting fabric with this solution for a sufficient time" is defined as the time necessary to impart fabric protection. This time can be as short as a few seconds or as long as 8 to 12 hours depending on the structure of the heavy metal ion control agent, its concentration, and the degree of protection needed as well as the type of fabric to be protected.

J. Anti-Fading Agents

See description of agents providing ultra-violet and color maintenance benefits.

K. Anti-Abrasion, Anti-Wear & Fabric Integrity Agents

1. Fabric Abrasion Reducing Polymers

The preferred reduced abrasion polymers of the present invention are water-soluble polymers having the formula:

$$[—P(D)_m-]_n$$

wherein the unit P is a polymer backbone which comprises units which are homopolymeric or copolymeric. D units are defined herein below. The term "homopolymeric" is defined as "a polymer backbone which is comprised of units having the same unit composition, i.e., formed from polymerization of the same monomer. The term "copolymeric" is defined as "a polymer backbone which is comprised of units having a different unit composition, i.e., formed from the polymerization of two or more monomers".

P backbones preferably comprise units having the formula:

$$—[CR_2—CR_2]— \text{ or } —[(CR_2)_x\text{-}L]\text{-}$$

wherein each R unit is independently hydrogen, $C_1$–$C_{12}$ alkyl, $C_6$–$C_{12}$ aryl, and D units as described herein below; preferably $C_1$–$C_4$ alkyl.

Each L unit is independently selected from heteroatom-containing moieties, non-limiting examples of which are selected from the group consisting of:

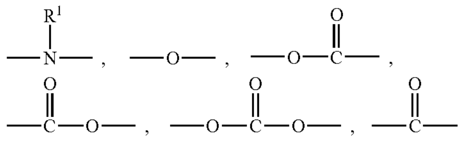

-continued

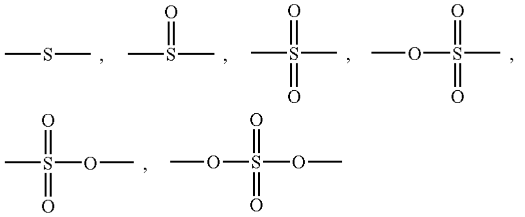

polysiloxane having the formula:

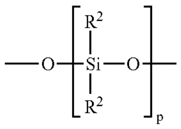

units which have dye transfer inhibition activity:

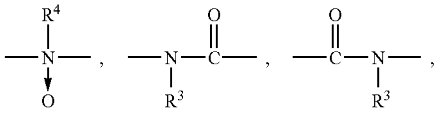

and mixtures thereof; wherein $R^1$ is hydrogen, $C_1$–$C_{12}$ alkyl, $C_6$–$C_{12}$ aryl, and mixtures thereof. $R^2$ is $C_1$–$C_{12}$ alkyl, $C_1$–$C_{12}$ alkoxy, $C_6$–$C_{12}$ aryloky, and mixtures thereof; preferably methyl and methoxy. $R^3$ is hydrogen $C_1$–$C_{12}$ alkyl, $C_6$–$C_{12}$ aryl, and mixtures thereof; preferably hydrogen or $C_1$–$C_4$ alkyl, more preferably hydrogen. $R^4$ is $C_1$–$C_{12}$ alkyl, $C_6$–$C_{12}$ aryl, and mixtures thereof.

The backbones of the fabric abrasion reducing polymers useful in the present invention comprise one or more D units which are units which comprise one or more units which provide a dye transfer inhibiting benefit. The D unit can be part of the backbone itself as represented in the general formula:

$$[\text{—P(D)}_m\text{-}]_n$$

or the D unit may be incorporated into the backbone as a pendant group to a backbone unit having, for example, the formula:

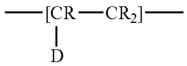 or 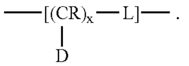

However, the number of D units depends upon the formulation. For example, the number of D units will be adjusted to provide water solubility of the polymer as well as efficacy of dye transfer inhibition while providing a polymer which has fabric abrasion reducing properties. The molecular weight of the fabric abrasion reducing polymers of the present invention are from about 500, preferably from about 1,000, more preferably from about 100,000 most preferably from 160,000 to about 6,000,000, preferably to about 2,000,000, more preferably to about 1,000,000, yet more preferably to about 500,000, most preferably to about 360,000 daltons. Therefore the value of the index n is selected to provide the indicated molecular weight, and providing for a water solubility of least 100 ppm, preferably at least about 300 ppm, and more preferably at least about 1,000 ppm in water at ambient temperature which is defined herein as 25° C.

a) Polymers Comprising Amide Units

Non-limiting examples of preferred D units are D units which comprise an amide moiety. Examples of polymers wherein an amide unit is introduced into the polymer via a pendant group includes polyvinylpyrrolidone having the formula:

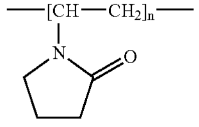

polyvinyloxazolidone having the formula:

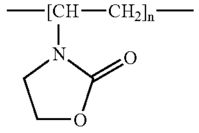

polyvinylmethyloxazolidone having the formula:

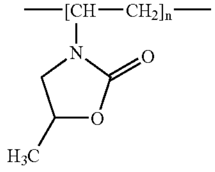

polyacrylamides and N-substituted polyacrylamides having the formula:

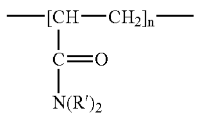

wherein each R' is independently hydrogen, $C_1$–$C_6$ alkyl, or both R' units can be taken together to form a ring comprising 4–6 carbon atoms; polymethacrylamides and N-substituted polymethacrylamides having the general formula:

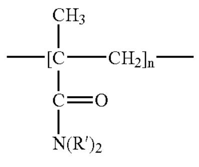

wherein each R' is independently hydrogen, $C_1$–$C_6$ alkyl, or both R' units can be taken together to form a ring comprising 4–6 carbon atoms; poly(N-acrylylglycinamide) having the formula:

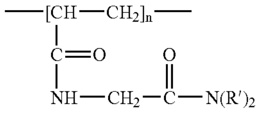

wherein each R' is independently hydrogen, $C_1$–$C_6$ alkyl, or both R' units can be taken together to form a ring comprising 4–6 carbon atoms; poly(N-methacrylylglycinamide) having the formula:

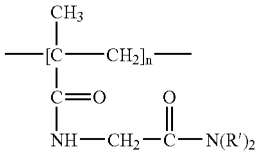

wherein each R' is independently hydrogen, $C_1$–$C_6$ alkyl, or both R' units can be taken together to form a ring comprising 4–6 carbon atoms; polyvinylurethanes having the formula:

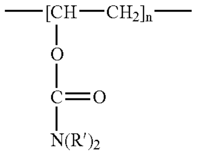

wherein each R' is independently hydrogen, $C_1$–$C_6$ alkyl, or both R' units can be taken together to form a ring comprising 4–6 carbon atoms.

An example of a D unit wherein the nitrogen of the dye transfer inhibiting moiety is incorporated into the polymer backbone is a poly(2-ethyl-2-oxazoline) having the formula:

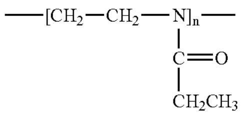

wherein the index n indicates the number of monomer residues present.

The fabric abrasion reducing polymers useful in the present invention can comprise any mixture of dye transfer inhibition units which provides the product with suitable properties. The preferred polymers which comprise D units which are amide moieties are those which have the nitrogen atoms of the amide unit highly substituted so the nitrogen atoms are in effect shielded to a varying degree by the surrounding non-polar groups. This provides the polymers with an amphiphilic character. Non-limiting examples include polyvinyl-pyrrolidones, polyvinyloxazolidones, N,N-disubstituted polyacrylamides, and N,N-disubstituted polymethacrylamides. A detailed description of physico-chemical properties of some of these polymers are given in, "Water-Soluble Synthetic Polymers: Properties and Behavior", Philip Molyneux, Vol. I, CRC Press, (1983) included herein by reference.

The amide containing polymers may be present partially hydrolyzed and/or cross linked forms. A preferred polymeric compound for the present invention is polyvinylpyrrolidone (PVP). This polymer has an amphiphilic character with a highly polar amide group conferring hydrophilic and polar-attracting properties, and also has non-polar methylene and methine groups, in the backbone and/or the ring, conferring hydrophobic properties. The rings may also provide planar alignment with the aromatic rings in the dye molecules. PVP is readily soluble in aqueous and organic solvent systems. PVP is available ex ISP, Wayne, N.J., and BASF Corp., Parsippany, N.J., as a powder or aqueous solutions in several viscosity grades, designated as, e.g., K-12, K-15, K-25, and K-30. These K-values indicate the viscosity average molecular weight, as shown below:

| | K-12 | K-15 | K-25 | K-30 | K-60 | K-90 |
|---|---|---|---|---|---|---|
| PVP viscosity average molecular weight (in thousands of daltons) | 2.5 | 10 | 24 | 40 | 160 | 360 |

PVP K-12, K-15, and K-30 are also available ex Polysciences, Inc. Warrington, Pa., PVP K-15, K-25, and K-30 and poly(2-ethyl-2-oxazoline) are available ex Aldrich Chemical Co., Inc., Milwaukee, Wis. PVP K30 (40,000) through to K90 (360,000) are also commercially available ex BASF under the tradename Luviskol or commercially available ex ISP. Still higher molecular PVP like PVP 1.3 MM, commercially available ex Aldrich is also suitable for use herein. Yet further PVP-type of material suitable for use in the present invention are polyvinylpyrrolidone-co-dimethylaminoethylmethacrylate, commercially available commercially ex ISP in a quaternised form under the tradename Gafquat® or commercially available ex Aldrich Chemical Co. having a molecular weight of approximately 1.0 MM; polyvinylpyrrolidone-co-vinyl acetate, available ex BASF under the tradename Luviskol®, available in vinylpyrrolidone:vinylacetate ratios of from 3:7 to 7:3.

b) Polymers Comprising N-oxide Units

Another D unit which provides dye transfer inhibition enhancement to the fabric abrasion reducing polymers described herein, are N-oxide units having the formula:

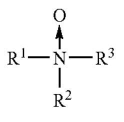

wherein $R^1$, $R^2$, and $R^3$ can be any hydrocarbyl unit (for the purposes of the present invention the term "hydrocarbyl" does not include hydrogen atom alone). The N-oxide unit may be part of a polymer, such as a polyamine, i.e., polyalkyleneamine backbone, or the N-oxide may be part of a pendant group attached to the polymer backbone. An example of a polymer which comprises an the N-oxide unit as a part of the polymer backbone is polyethyleneimine N-oxide. Non-limiting examples of groups which can comprise an N-oxide moiety include the N-oxides of certain heterocycles inter alia pyridine, pyrrole, imidazole, pyrazole, pyrazine, pyrimidine, pyridazine, piperidine, pyrrolidine, pyrrolidone, azolidine, morpholine. A preferred polymer is poly(4-vinylpyridine N-oxide, PVNO). In addition, the N-oxide unit may be pendant to the ring, for example, aniline oxide.

N-oxide comprising polymers will preferably have a ration of N-oxidized amine nitrogen to non-oxidized amine nitrogen of from about 1:0 to about 1:2, preferably to about 1:1, more preferably to about 3:1. The amount of N-oxide units can be adjusted by the formulator. For example, the formulator may co-polymerize N-oxide comprising monomers with non N-oxide comprising monomers to arrive at the desired ratio of N-oxide to non N-oxide amino units, or the formulator may control the oxidation level of the polymer during preparation. The amine oxide unit of the polyamine N-oxides of the present invention have a $Pk_a$ less than or equal to 10, preferably less than or equal to 7, more preferably less than or equal to 6. The average molecular weight of the N-oxide comprising polymers which provide a dye transfer inhibitor benefit to reduced fabric abrasion polymers is from about 500 daltons, preferably from about 100,000 daltons, more preferably from about 160,000 daltons to about 6,000,000 daltons, preferably to about 2,000,000 daltons, more preferably to about 360,000 daltons.

c) Polymers Comprising Amide Units and N-oxide Units

A further example of polymers which are fabric abrasion reducing polymers which have dye transfer inhibition benefits are polymers which comprise both amide units and N-oxide units as described herein above. Non-limiting examples include co-polymers of two monomers wherein the first monomer comprises an amide unit and the second monomer comprises an N-oxide unit. In addition, oligomers or block polymers comprising these units can be taken together to form the mixed amide/N-oxide polymers. However, the resulting polymers must retain the water solubility requirements described herein above.

L. Brighteners

Commercial optical brighteners which may be useful in the present invention can be classified into subgroups, which include, but are not necessarily limited to, derivatives of stilbene, pyrazoline, coumarin, carboxylic acid, methinecyanines, dibenzothiphene-5,5-dioxide, azoles, 5- and 6-membered-ring heterocycles, and other miscellaneous agents. Examples of such brighteners are disclosed in "The Production and Application of Fluorescent Brightening Agents", M. Zahradnik, Published by John Wiley & Sons, New York (1982).

Specific examples of optical brighteners which are useful in the present compositions are those identified in U.S. Pat. No. 4,790,856, issued to Wixon on Dec. 13, 1988. These brighteners include the PHORWHITE series of brighteners from Verona. Other brighteners disclosed in this reference include: Tinopal UNPA, Tinopal CBS and Tinopal 5BM; available from Ciba-Geigy; Artic White CC and Artic White CWD, available from Hilton-Davis, located in Italy; the 2-(4-stryl-phenyl)-2H-napthol[1,2-d]triazoles; 4,4'-bis-(1,2,3-triazol-2-yl)-stil-benes; 4,4'-bis(stryl)bisphenyls; and the aminocoumarins. Specific examples of these brighteners include 4-methyl-7-diethyl-amino coumarin; 1,2-bis(-venzimidazol-2-yl)ethylene; 1,3-diphenyl-phrazolines; 2,5-bis (benzoxazol-2-yl)thiophene; 2-stryl-napth-[1,2-d]oxazole; and 2-(stilbene-4-yl)-2H-naphtho-[1,2-d]triazole. See also U.S. Pat. No. 3,646,015, issued Feb. 29, 1972 to Hamilton. Anionic brighteners are preferred herein.

More specifically, the hydrophilic optical brighteners useful in the present invention are those having the structural formula:

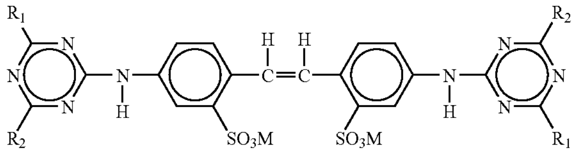

wherein $R_1$ is selected from anilino, N-2-bis-hydroxyethyl and NH-2-hydroxyethyl; $R_2$ is selected from N-2-bis-hydroxyethyl, N-2-hydroxyethyl-N-methylamino, morphilino, chloro and amino; and M is a salt-forming cation such as sodium or potassium.

When in the above formula, $R_1$ is anilino, $R_2$ is N-2-bis-hydroxyethyl and M is a cation such as sodium, the brightener is 4,4',-bis[(4-anilino-6-(N-2-bis-hydroxyethyl)-s-triazine-2-yl)amino]-2,2'-stilbenedisulfonic acid and disodium salt. This particular brightener species is commercially marketed under the trade name Tinopal-UNPA-GX® by Ciba-Geigy Corporation. Tinopal-UNPA-GX is the preferred hydrophilic optical brightener useful in the rinse added compositions herein.

When in the above formula, $R_1$ is anilino, $R_2$ is N-2-hydroxyethyl-N-2-methylamino and M is a cation such as sodium, the brightener is 4,4'-bis[(4-anilino-6-(N-2-hydroxyethyl-N-methylamino)-s-triazine-2-yl)amino]2,2'-stilbenedisulfonic acid disodium salt. This particular brightener species is commercially marketed under the tradename Tinopal 5BM-GX® by Ciba-Geigy Corporation.

When in the above formula, $R_1$ is anilino, $R_2$ is morphilino and M is a cation such as sodium, the brightener is 4,4'-bis[(4-anilino-6-morphilino-s-triazine-2-yl)amino]2,2'-stilbenedisulfonic acid, sodium salt. This particular brightener species is commercially marketed under the tradename Tinopal AMS-GX® by Ciba Geigy Corporation.

M. Defoamers & Anti-Foaming Agents

Compounds for reducing or suppressing the formation of suds in the wash or rinse bath solutions may also be unitized for use in the present invention. Suds suppression can be of particular importance in the so-called "high concentration cleaning process" as described in U.S. Pat. Nos. 4,489,455 and 4,489,574 and in front-loading European-style washing machines.

A wide variety of materials may be used as suds suppressers, and suds suppressers are well known to those skilled in the art. See, for example, Kirk Othmer Encyclopedia of Chemical Technology, Third Edition, Volume 7, pages 430–447 (John Wiley & Sons, Inc., 1979). One category of suds suppresser of particular interest encompasses monocarboxylic fatty acid and soluble salts therein, as described in U.S. Pat. No. 2,954,347, issued Sep. 27, 1960 to Wayne St. John. The monocarboxylic fatty acids and salts thereof used as suds suppressor typically have hydrocarbyl chains of 10 to about 24 carbon atoms, preferably 12 to 18 carbon atoms. Suitable salts include the alkali metal salts such as sodium, potassium, and lithium salts, and ammonium and alkanolammonium salts.

The detergent compositions herein may also contain nonsurfactant suds suppressers. These include, for example: high molecular weight hydrocarbons such as paraffin, fatty acid esters (e.g., fatty acid triglycerides), fatty acid esters of monovalent alcohols, aliphatic $C_{18}$–$C_{40}$ ketones (e.g., stearone), etc. Other suds inhibitors include N-alkylated amino triazines such as tri- to hexa-alkylmelamines or di- to tetra-alkyldiamine chlortriazines formed as products of cyanuric chloride with two or three moles of a primary or secondary amine containing 1 to 24 carbon atoms, propylene oxide, and monostearyl phosphates such as monostearyl alcohol phosphate ester and monostearyl di-alkali metal (e.g., K, Na, and Li) phosphates and phosphate esters. The hydrocarbons such as paraffin and haloparaffin can be utilized in liquid form. The liquid hydrocarbons will be liquid at room temperature and atmospheric pressure, and will have a pour point in the range of about −40° C. and about 50° C., and a minimum boiling point of not less than about 110° C. (atmospheric pressure). It is also known to utilize waxy hydrocarbons, preferably having a melting point below about 100° C. The hydrocarbons constitute a preferred category of suds suppresser for detergent compositions. Hydrocarbon suds suppressers are described, for example, in U.S. Pat. No. 4,265,779, issued May 5, 1981 to Gandolfo et al. The hydrocarbons, thus, include aliphatic, alicyclic, aromatic, and heterocyclic saturated or unsaturated hydrocarbons having from about 12 to about 70 carbon atoms. The term "paraffin," as used in this suds suppresser discussion, is intended to include mixtures of true paraffins and cyclic hydrocarbons.

Another preferred category of non-surfactant suds suppressers comprises silicone suds suppressers. This category includes the use of polyorganosiloxane oils, such as polydimethylsiloxane, dispersions or emulsions of polyorganosiloxane oils or resins, and combinations of polyorganosiloxane with silica particles wherein the polyorganosiloxane is chemisorbed or fused onto the silica. Silicone suds suppressers are well known in the art and are, for example, disclosed in U.S. Pat. No. 4,265,779, issued May 5, 1981 to Gandolfo et al and European Patent Application No. 89307851.9, published Feb. 7, 1990, by Starch, M. S. Other silicone suds suppressers are disclosed in U.S. Pat. No. 3,455,839 which relates to compositions and processes for defoaming aqueous solutions by incorporating therein small amounts of polydimethylsiloxane fluids.

Mixtures of suds suppressers may also be used to advantage. Mixtures of silicone and silanated silica are described in German Patent Application DOS 2,124,526. Silicone defoamers and suds controlling agents in granular detergent compositions are disclosed in U.S. Pat. No. 3,933,672, Bartolotta et al, and in U.S. Pat. No. 4,652,392, Baginski et al. Another preferred foam suppressant is a silicone/silicate mixture, e.g., Dow Corning's Antifoam AR.

An exemplary silicone based suds suppressor for use herein is a suds suppressing amount of a suds controlling agent consisting essentially of:

(i) polydimethylsiloxane fluid having a viscosity of from about 20 cs. to about 1,500 cs. at 25° C.;

(ii) from about 5 to about 50 parts per 100 parts by weight of (i) of siloxane resin composed of $(CH_3)_3SiO_{1/2}$ units of $SiO_2$ units in a ratio of from $(CH_3)_3SiO_{1/2}$ units and to $SiO_2$ units of from about 0.6:1 to about 1.2:1; and (iii) from about 1 to about 20 parts per 100 parts by weight of (i) of a solid silica gel.

In the preferred silicone suds suppressor used herein, the solvent for a continuous phase is made up of certain polyethylene glycols or polyethylene-polypropylene glycol copolymers or mixtures thereof (preferred), or polypropylene glycol. The primary silicone suds suppressor is branched/cross linked and preferably not linear.

To illustrate this point further, typical liquid laundry detergent compositions with controlled suds will optionally comprise from about 0.001 to about 1, preferably from about 0.01 to about 0.7, most preferably from about 0.05 to about 0.5, weight % of said silicone suds suppressor, which comprises (1) a nonaqueous emulsion of a primary antifoam agent which is a mixture of (a) a polyorganosiloxane, (b) a resinous siloxane or a silicone resin-producing silicone compound, (c) a finely divided filler material, and (d) a catalyst to promote the reaction of mixture components (a), (b) and (c), to form silanolates; (2) at least one nonionic silicone surfactant; and (3) polyethylene glycol or a copolymer of polyethylene-polypropylene glycol having a solubility in water at room temperature of more than about 2 weight %; and without polypropylene glycol. Similar amounts can be used in granular compositions, gels, etc, as described in U.S. Pat. No. 4,978,471, Starch, issued Dec. 18, 1990, and U.S. Pat. No. 4,983,316, Starch, issued Jan. 8, 1991, U.S. Pat. No. 5,288,431, Huber et al., issued Feb. 22, 1994, and U.S. Pat. Nos. 4,639,489 and 4,749,740, Aizawa et al at.

A silicone suds suppressor particularly useful in the compositions and articles of the present invention comprises polyethylene glycol and a copolymer of polyethylene glycol/polypropylene glycol, all having an average molecular weight of less than about 1,000, preferably between about 100 and 800. The polyethylene glycol and polyethylene/polypropylene glycol copolymers herein have a solubility in water at room temperature of more than about 2%, and preferably more than about 5% by weight. The preferred solvent herein is polyethylene glycol having an average molecular weight of less than about 1,000, more preferably between about 100 and 800, most preferably between 200 and 400, and a copolymer of polyethylene glycol/polypropylene glycol, preferably PPG 200/PEG 300. Preferred is a weight ratio of between about 1:1 and 1:10, most preferably between 1:3 and 1:6, of polyethylene glycol:copolymer of polyethylene-polypropylene glycol.

Other suds suppressers useful herein comprise the secondary alcohols (e.g., 2-alkyl alkanols) and mixtures of such alcohols with silicone oils, such as the silicones disclosed in U.S. Pat. Nos. 4,798,679, 4,075,118 and EP 150,872. The secondary alcohols include the $C_6$–$C_{16}$ alkyl alcohols having a $C_1$–$C_{16}$ chain. A preferred alcohol is 2-butyl octanol, which is available from Condea under the trademark ISOFOL 12. Mixtures of secondary alcohols are available under the trademark ISALCHEM 123 from Enichem. Mixed suds suppressers typically comprise mixtures of alcohol+silicone at a weight ratio of 1:5 to 5:1.

N. Rinse Aids

The fabric care actives of the present invention may also comprise rinse aids which typically comprise mixtures or one or more of the following fabric care agents: anti-foaming compounds, pH buffering agents, crystal growth inhibitors including carboxylic compounds, and organic diphosphonic and monophosphonic acids, heavy metal ion sequestrants including chelants and chlorine scavengers, hydrophobic dispersants, polymeric stabilizing agents, soil release polymers, preservatives, and anti-microbials.

O. Ultraviolet Protection Agents

The incorporation of sunscreens and antioxidants into a wash or rinse bath solution for various benefits is also known in the art. For example, U.S. Pat. No. 4,900,469, teaches antioxidants in detergent solutions for bleach stability. Antioxidants have likewise been used in softeners and detergents to prevent fabric yellowing and to control malodor. (See, JP 72/116,783, Kao.) JP 63/162,798, teaches the use of sunscreens to stabilize the color of fabric conditioning compositions. U.S. Pat. No. 5,134,223, Langer et al., issued Jul. 28, 1992, teaches copolymers with a UV-absorbing monomer and a hydrophilic monomer to provide both anti-fading and soil release benefits. More specifically, this reference teaches the combination of a polymer of UV-absorbing monomers to a soil release polymer consisting of a hydrophilic group (e.g. ethoxylate) and hydrophobic group (e.g. terephthalate blocks). U.S. Pat. No. 5,250,652, Langer et al., issued Oct. 5, 1993, teaches copolymers containing at least one UVA light-absorbing moiety and/or one UVB light-absorbing moiety, one low molecular weight (i.e., monomeric) hydrophilic moiety, and optionally one hydrophobic moiety for fabric care (detergents, fabric softeners, etc.) and skin care applications (cosmetics, shampoos, sunscreens, personal cleansing compositions, etc.). The use of low molecular weight hydrophilic moieties allows a loading of UVA and/or UVB moieties of up to about 95% and provides better dispersibility of the polymer in an aqueous media. The optional hydrophobic moiety provides control over the deposition of the copolymer on a desired surface.

1. Antioxidants

An antioxidant that may be used in the compositions and articles of the present invention is a non-fabric staining, light stable antioxidant compound preferably containing at least one $C_8$–$C_{22}$ hydrocarbon fatty organic moiety, preferably at least one $C_{12}$–$C_{18}$ hydrocarbon fatty organic moiety, wherein the antioxidant compound is a solid having a melting point of less than about 80° C., preferably less than about 50° C., or a liquid at a temperature of less than about 40° C., preferably from about 0° C. to about 25° C.

Preferred antioxidant compounds include:

(I)

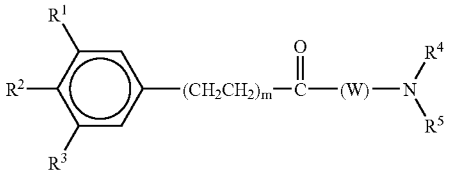

(II)

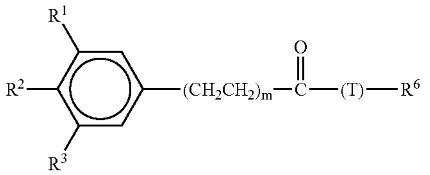

(III)

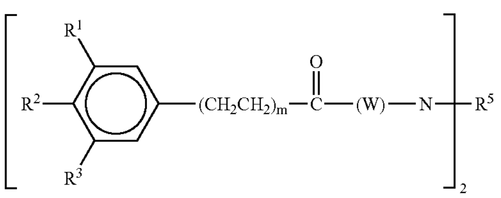

(IV)

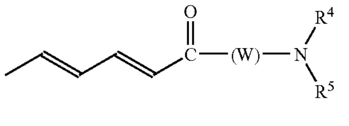

(V)

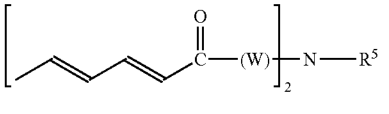

-continued (VI)

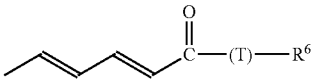

(VII)

and mixtures thereof;

wherein each $R^1$ and $R^3$ are the same or different moiety selected from the group consisting of hydroxy, $C_1$ to $C_6$ alkoxy groups (i.e., methoxy, ethoxy, propoxy, butoxy groups), branched or straight chained $C_1$ to $C_6$ alkyl groups, and mixtures thereof, preferably branched $C_1$ to $C_6$ alkyl groups, more preferably "tert"-butyl groups;

each $R^2$ is a hydroxy group;

each $R^4$ is a saturated or unsaturated $C_1$ to $C_{22}$ alkyl group or hydrogen, preferably a methyl group;

each $R^5$ is a saturated or unsaturated $C_1$ to $C_{22}$ alkyl group which can contain one or more ethoxylate or propoxylate groups, preferably a saturated or unsaturated $C_8$ to $C_{22}$ alkyl group, more preferably a saturated or unsaturated $C_{12}$ to $C_{18}$ alkyl group, and even more preferably a saturated or unsaturated $C_{12}$ to $C_{14}$ alkyl group;

each $R^6$ is a branched or straight chained, saturated or unsaturated, $C_8$ to $C_{22}$ alkyl group, preferably a branched or straight chained, saturated or unsaturated $C_{12}$ to $C_{18}$ alkyl group, more preferably a branched or straight chained, saturated or unsaturated $C_{16}$ to $C_{18}$ alkyl group;

each T is O or N; each W is 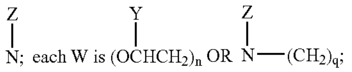

wherein Y is a hydrogen, a $C_1$ to $C_5$ alkyl group, preferably hydrogen or a methyl group, more preferably hydrogen;

wherein Z is hydrogen, a $C_1$ to $C_3$ alkyl group (which can be interrupted by an ester, amide, or ether group), a $C_1$ to $C_{30}$ alkoxy group (which can be interrupted by an ester, amide, or ether group), preferably hydrogen or a $C_1$ to $C_6$ alkyl group;

each m is from 0 to 4, preferably from 0 to 2;

each n is from 1 to 50, preferably from 1 to 10, more preferably 1; and each q is from 1 to 10, preferably from 2 to 6.

The antioxidants of the present invention can also comprise quaternary ammonium salts of Formulas I, III, IV and V, although amines of Formulas I, III, IV and V are preferred.

The antioxidant compounds of the present invention preferably comprise amine compounds of Formulas I, II, III, and mixtures thereof.

A preferred compound of Formula (II) is Octadecyl 3,5-di-tert-butyl-4-hydroxyhydrocinnamate, known under the trade name of Irganox® 1076 available from Ciba-Geigy Co.

A preferred compound of formula (III) is N,N-bis[ethyl 3',5'-di-tert-butyl-4'-hydroxybenzoate]N-cocoamine.

The preferred antioxidants for use in the compositions of the present invention include 2-(N-methyl-N-coco-amino) ethyl 3',5'-di-tert-butyl-4'-hydroxybenzoate; 2-(N,N-dimethylamino)ethyl 3',5'-di-tert-butyl-4'-hydroxybenzoate;

2-(N-methyl-N-cocoamino)ethyl 3',4',5'-tri-hydroxybenzoate; and mixtures thereof, more preferably 2-(N-methyl-N-coco-amino)ethyl 3',5'-di-tert-butyl-4'-hydroxybenzoate. Of these compounds, the butylated compounds are preferred because the non-butylated compounds have a tendency to discolor in the composition of the present invention.

The antioxidant compounds to be used in the present invention demonstrate light stability in the compositions and articles. "Light stable" means that the antioxidant compounds in the compositions of the present invention do not discolor when exposed to either sunlight or simulated sunlight for approximately 2 to 60 hours at a temperature of from about 25° C. to about 45° C.

Descriptions of suitable antioxidants are provided in U.S. Pat. Nos. 5,543,083; 5,705,474; 5,723,435; 5,763,387; and 5,854,200.

2. Sunscreen Actives

The present invention may optionally include unitized dosing of a sunscreen compound that absorbs light at a wavelength of from about 290 nm to about 450 nm and more preferably from 315 nm to 400 nm. The sunscreen compound is a solid having a melting point of from about 25° C. to about 90° C., and more preferably from 25° C. to about 75° C., and even more preferably from about 25° C. to about 50° C., or a viscous liquid at a temperature of less than about 40° C. and preferably between about 0□C and about 25° C. Preferably, the sunscreen compound comprises at least one $C_8$ to $C_{22}$ hydrocarbon fatty organic moiety, more preferably at least one $C_{12}$ to $C_{18}$ hydrocarbon fatty organic moiety.

These sunscreen compounds preferably contain at least one of the following chromophores:

(I)

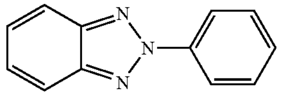

Phenylbenzotriazole (II)

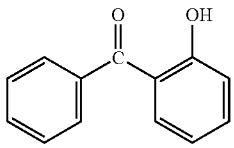

2-Hydroxybenzophenone (III)

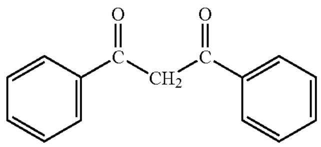

Dibenzoylmethane (IV)

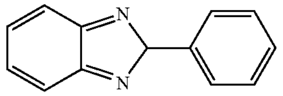

Phenylbenzimidazole

-continued (V)

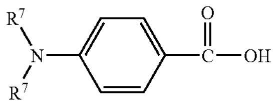

Esters of P-Aminobenzoic Acid (PABA)

(VI)

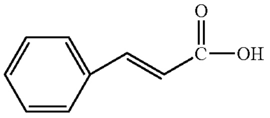

Esters of Cinnamic Acid (VII)

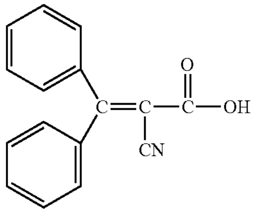

Esters of 2-Cyano-3, 3-Diphenyl-2-Propenoic Acid (VIII)

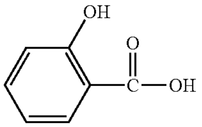

Esters of Salicylic Acid and (IX)

mixtures thereof;

wherein $R^7$ is a hydrogen, methyl, ethyl, $C_1$ to $C_{22}$ branched or straight chain alkyl group; and mixtures thereof, preferably a methyl group; and wherein the compound containing the chromophore is a non-fabric staining, light stable compound containing preferably at least one $C_8$–$C_{22}$ hydrocarbon fatty organic moiety; wherein the chromophore absorbs light at a wavelength of from about 290 nm to about 450 nm; wherein the compound is a solid having a melting point of from about 25° C. to about 90° C. or a viscous liquid at a temperature of less than about 40° C.

Most preferably, the sunscreen compound is selected from the group consisting of:

(I)

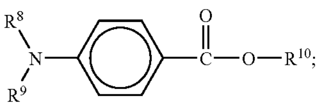

(II)

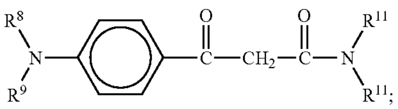

-continued (III)

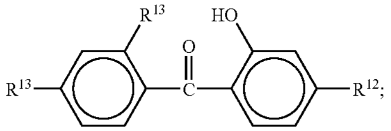

(IV)

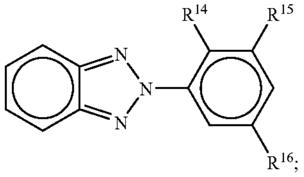

(V)

mixtures thereof;

wherein each $R^8$ is a hydrogen or a $C_1$–$C_{22}$ alkyl group; preferably a hydrogen or a methyl group;

each $R^9$ is a hydrogen, or a $C_1$–$C_{22}$ alkyl group; preferably a hydrogen or a methyl group;

each $R^{10}$ is a $C_1$–$C_{22}$ alkyl group, preferably a $C_8$–$C_{18}$ alkyl group; more preferably a $C_{12}$–$C_{18}$ alkyl group;

each $R^{11}$ is a hydrogen, a $C_1$–$C_{22}$ alkyl group and mixtures thereof, preferably a methyl group, a $C_8$–$C_{22}$ alkyl group, and mixtures thereof, more preferably, one $R^{11}$ group is a $C_{10}$–$C_{20}$ alkyl group, preferably a $C_{12}$–$C_{18}$ alkyl group, and the other $R^{11}$ group is a methyl group;

each $R^{12}$ is a hydrogen, hydroxy group, methoxy group, a $C_1$–$C_{22}$ alkyl group (which can be an ester, amide, or ether interrupted group) and mixtures thereof, preferably a $C_1$–$C_{22}$ alkyl group with an ether or ester interrupted group, and mixtures thereof, more preferably a methoxy group, a $C_8$–$C_{22}$ alkyl group with an ester interrupted group, and mixtures thereof;

each $R^{13}$ is a hydrogen, hydroxy group, a $C_1$–$C_{22}$ alkyl group (which can be an ester, amide, or ether interrupted group) and mixtures thereof, preferably a hydrogen, hydroxy group, and mixtures thereof, more preferably hydrogen;

each $R^{14}$ is a hydrogen, hydroxy group, or a $C_1$–$C_{22}$ alkyl group, preferably a hydrogen or a hydroxy group, more preferably a hydroxy group;

each $R^{15}$ is a hydrogen, hydroxy group, a $C_1$–$C_{22}$ alkyl group (which can be an ester, amide, or ether interrupted group), and mixtures thereof, preferably a $C_1$–$C_{12}$ alkyl group, more preferably a $C_1$–$C_8$ alkyl group, and even more preferably a methyl group, a "tert"-amyl group, or a dodecyl group;

each $R^{16}$ is a hydrogen, hydroxy group, or a $C_1$–$C_{22}$ alkyl group (which can be an ester, amide, or ether interrupted group), preferably a "tert"-amyl, a methyl phenyl group, or a coco dimethyl butanoate group.

However, $R^{12}$, $R^{13}$, $R^{14}$, $R^{15}$ and $R^{16}$ can be interrupted by the corresponding ester linkage interrupted group with a short alkylene ($C_1$–$C_4$) group.

Preferred sunscreen compounds for use in the compositions of the present invention are selected from the group consisting of fatty derivatives of PABA, benzophenones, cinnamic acid and phenyl benzotriazoles, specifically, octyl dimethyl PABA, dimethyl PABA lauryl ester, dimethyl PABA oleyl ester, benzophenone-3 coco acetate ether, benzophenone-3 available under the tradename Spectra-Sorb® UV-9 from Cyanamid, 2-(2'-Hydroxy-3',5'-di-tert-amylphenyl benzotriazole which is available under the tradename Tinuvin® 328 from Ceiba-Geigy, Tinuvin® coco ester 2-(2' Hydroxy, 3'-(coco dimethyl butanoate)-5'-methylphenyl) benzotriazole, and mixtures thereof. Preferred sunscreen compounds of the present invention are benzotriazole derivatives since these materials absorb broadly throughout the UV region. Preferred benzotriazole derivatives are selected from the group consisting of 2-(2'-Hydroxy, 3'dodecyl, 5'-methylphenyl benzotriazole from Ciba-Geigy, available under the tradename Tinuvin® 571 Coco 3-[3'-(2H-benzotriazol-2''-yl)-5'-tert-butyl-4'-hydroxyphenyl] propionate.

The sunscreen compounds of the present invention demonstrate light stability in the compositions of the present invention. "Light stable" means that the sunscreen agents in the compositions of the present invention do not discolor when exposed to either sunlight or simulated sunlight for approximately 2 to 60 hours at a temperature of from about 25° C. to about 45° C.

3. Mixtures of Antioxidant and Sunscreen Compounds

The present compositions and articles can comprise a mixture of antioxidant compounds and sunscreen compounds. Combinations of the sun-fade protection actives are particularly desirable because they address different mechanisms. Whereas the antioxidant compound protects dye degradation by preventing the generation of singlet oxygen and peroxy radicals and terminating degradation pathways; the sunscreen compound broadly absorbs UVA light in order to protect against sun-fade. The combination of these two mechanisms allows for broad sun-fade protection. When a mixture is present, the ratio of antioxidant to sunscreen is typically from about 1:10 to about 10:1, preferably from about 1:5 to about 5:1, and more preferably from about 1:2 to about 2:1.

P. Insect Repellents

The fabric care compositions of the present invention may contain an effective amount of insect and/or moth repelling agents. Typical insect and moth repelling agents are pheromones, such as anti-aggregation pheromones, and other natural and/or synthetic ingredients. Preferred insect and moth repellent agents useful in the composition of the present invention are perfume ingredients, such as citronellol, citronellal, citral, linalool, cedar extract, geranium oil, sandalwood oil, 2-(diethylphenoxy)ethanol, 1-dodecene, etc. Other examples of insect and/or moth repellents useful in the composition of the present invention are disclosed in U.S. Pat. Nos. 4,449,987, 4,693,890, 4,696,676, 4,933,371, 5,030,660, 5,196,200, and in "Semio Activity of Flavor and Fragrance Molecules on Various Insect Species", B. D. Mookherjee et al., published in *Bioactive Volatile Compounds from Plants*, ASC Symposium Series 525, R. Teranishi, R. G. Buttery, and H. Sugisawa, 1993, pp. 35–48, all of said patents and publications being incorporated herein by reference.

Q. Enzymes to Facilitate

1. Cleaning/Whitening

Enzymes may be included in the present compositions and articles for a variety of purposes, including removal of protein-based, carbohydrate-based, or triglyceride-based stains from textiles, the prevention of refugee dye transfer during laundering, and fabric restoration. Suitable enzymes include proteases, amylases, lipases, cellulases, peroxidases, and mixtures thereof of any suitable origin, such as vegetable, animal, bacterial, fungal and yeast origin. Preferred selections are influenced by factors such as pH-activity and/or stability optima, thermostability, and stability to active detergents, builders and the like. In this respect, bacterial or fungal enzymes are preferred, such as bacterial amylases and proteases, and fungal cellulases.

"Detersive enzyme", as used herein, means any enzyme having a cleaning, stain removing or otherwise beneficial effect in a laundry wash or rinse bath solution. Preferred enzymes for laundry purposes include, but are not limited to, proteases, cellulases, lipases and peroxidases. Enzymes are normally used at levels sufficient to provide a "cleaning-effective amount". The term "cleaning effective amount" refers to any amount capable of producing a cleaning, stain removal, soil removal, whitening, deodorizing, or freshness improving effect on fabrics.

Suitable examples of proteases are the subtilisins which are obtained from particular strains of *B. subtilis* and *B. licheniformis*. One suitable protease is obtained from a strain of *Bacillus*, having maximum activity throughout the pH range of 8–12, developed and sold as ESPERASE® by Novo Industries A/S of Denmark, hereinafter "Novo". The preparation of this enzyme and analogous enzymes is described in GB 1,243,784 to Novo. Other suitable proteases include ALCALASE® and SAVINASE® from Novo and MAXATASE® from International Bio-Synthetics, Inc., The Netherlands; as well as Protease A as disclosed in EP 130,756 A, Jan. 9, 1985 and Protease B as disclosed in EP 303,761 A, Apr. 28, 1987 and EP 130,756 A, Jan. 9, 1985. See also a high pH protease from *Bacillus* sp. NCIMB 40338 as described in WO 9318140 A. Other preferred proteases include those of WO 9510591 A. When desired, a protease having decreased adsorption and increased hydrolysis is available as described in WO 9507791. A recombinant trypsin-like protease for detergents suitable herein is described in WO 9425583.

An especially preferred protease, referred to as "Protease D" is a carbonyl hydrolase variant having an amino acid sequence not found in nature, which is derived from a precursor carbonyl hydrolase by substituting a different amino acid for a plurality of amino acid residues, as described in the patent applications of A. Baeck, et al, entitled "Protease-Containing Cleaning Compositions" having U.S. Ser. No. 08/322,676, and C. Ghosh, et al, "Bleaching Compositions Comprising Protease Enzymes" having U.S. Ser. No. 08/322,677, both filed Oct. 13, 1994.

Cellulases usable herein include both bacterial and fungal types, preferably having a pH optimum between 5 and 9.5. U.S. Pat. No. 4,435,307, Barbesgoard et al, Mar. 6, 1984, discloses suitable fungal cellulases from *Humicola insolens* or *Humicola* strain DSM1800 or a cellulase 212-producing fungus belonging to the genus *Aeromonas*, and cellulase extracted from the hepatopancreas of a marine mollusk, *Dolabella Auricula Solander*. Suitable cellulases are also disclosed in GB-A-2.075.028; GB-A-2.095.275 and DE-OS-2.247.832. CAREZYME® (Novo) is especially useful. See also WO 9117243 to Novo.

Suitable lipase enzymes for use in a wash solution with detergent include those produced by microorganisms of the *Pseudomonas* group, such as *Pseudomonas stutzeri* ATCC 19.154, as disclosed in GB 1,372,034. See also lipases in Japanese Patent Application 53,20487, laid open Feb. 24, 1978. This lipase is available from Amano Pharmaceutical Co. Ltd., Nagoya, Japan, under the trade name Lipase P "Amano," or "Amano-P." Other suitable commercial lipases include Amano-CES, lipases ex *Chromobacter viscosum*, e.g. *Chromobacter viscosum* var. *lipolyticum* NRRLB 3673 from Toyo Jozo Co., Tagata, Japan; *Chromobacter viscosum* lipases from U.S. Biochemical Corp., U.S.A. and Disoynth Co., The Netherlands, and lipases ex *Pseudomonas gladioli*. LIPOLASE® enzyme derived from *Humicola lanuginosa* and commercially available from Novo, see also EP 341, 947, is a preferred lipase for use herein. Lipase and amylase variants stabilized against peroxidase enzymes are described in WO 9414951 A. See also WO 9205249 and RD 94359044.

Peroxidase enzymes may be used in combination with oxygen sources, e.g., percarbonate, perborate, hydrogen peroxide, etc., for "solution bleaching" or prevention of transfer of dyes or pigments removed from substrates during the wash to other substrates present in the wash solution. Known peroxidases include horseradish peroxidase, ligninase, and haloperoxidases such as chloro- or bromo-peroxidase. Peroxidase-containing detergent compositions are disclosed in WO 89099813 A, Oct. 19, 1989 and WO 8909813 A.

Because of the unitization that is provided by the present invention, the use of stabilizers and stabilization systems is not necessary as was previously required for bulk enzyme-detergent compositions.

II. Fabric Care Articles

A. General

The laundry articles of the present invention utilize a wide range of materials and processes to deliver a pre-measured or unitized amount of fabric care active to a laundry solution by dispensing in that solution an article having a variety of forms and features. Generally, the dose forms and articles of the present invention should be sufficiently water soluble so that the materials of the articles will rapidly dissociate upon contact with water, thereby releasing the active or mixture of actives to the solution within the first several minutes of the wash or rinse cycle. When released to the laundry solution, the actives may carry out their intended function by being deposited on fabrics in the solution or they may interact with materials in solution, such as calcium and magnesium minerals, to impart a given fabric care benefit to fabrics laundered in that solution or eliminate a negative effect (eg. Water hardness).

The delivery of a unitized dose of an active or mixture of actives enables the user of the article to select and control the fabric care actives that are deposited on a given fabric or that are in solution to counteract materials that may have a detrimental effect on the fabrics. By isolating actives from one another in this manner, it is possible to deliver actives that could not previously be formulated with other actives into a single fabric care composition. Similarly, actives that are known to create stability and viscosity problems, and as such have been used in only limited concentrations in existing fabric care compositions, may now be delivered in effective amounts as desired. In addition, the need for stabilizers and modifiers that may have been necessary to achieve a stable fabric care composition have in many cases been eliminated by the unitized dosing of the compositions of the present invention.

Specifically, in its most simplified form, an article of the present invention comprises a unitized dose of a fabric care composition that has a fabric care active or mixture of actives at a level between about 1% and about 99% by weight of the fabric care composition. The article has less than about 5%, more preferably less than about 3%, and even more preferably less than about 1% detergent surfactant and less than about 5%, more preferably less than about 3%, and even more preferably less than about 1% fabric softener active, as defined herein. Most preferably however, the fabric care article is free of both detergent and fabric softener actives.

As used herein, "unitized" refers to the amount of a given fabric care active or mixture of actives that should be delivered to a laundry solution, in either a wash or rinse bath solution, to provide an effective amount of the fabric care active to a minimum volume of fabrics in a minimum volume of laundry solution, to thereby produce the fabric care benefit associated with that active. The function of the various fabric care actives that may be used in the compositions and articles of the present invention is not limited to materials that are to be deposited on fabrics. As noted herein, the fabric care actives may also include actives to reduce hard water minerals, suds suppressers, chelating agents and other agents that interact with materials in the laundry solution itself. Similarly with respect to such fabric care actives, unitization refers to an effective amount of the active to produce the fabric care benefit associated with that active in a minimum volume of laundry solution. For loads containing larger volumes of fabrics and solution, multiple units of a given unitized fabric care active may be needed to provide the desired fabric care benefit.

The article of the present invention will have a weight between about 0.05 g and about 60 g depending on the type and amount of active or mixture of actives that are contained therein and the non-active ingredients that may be present. It is preferred that the article weigh between about 2 g and about 40 g and more preferably between about 4 g and about 35 g. Further, it is preferred that solid articles be sufficiently robust to withstand handling, packaging, and distribution without breakage, leakage or dusting prior to being dispensed in a laundry solution.

An article of the present invention will comprise a fabric care active or mixture of actives including perfumes, bodying agents, drape and form control agents, smoothness agents, static control agents, wrinkle control agents, sanitization agents, drying agents, stain resistance agents, soil release agents, malodor control agents, dye fixatives, dye transfer inhibitors, color maintenance agents, anti-fading agents, whiteness enhancers, anti-abrasion agents, fabric integrity agents, anti-wear agents, color appearance restoration agents, brightness restoration agents, defoamers, rinse aids, UV protection agents, sun fade inhibitors, insect repellents, mite control agents, enzymes, and mixtures thereof. These fabric care actives are described in detail in conjunction with the description concerning the compositions of the present invention.

It should be noted that the list of fabric care actives described herein for use in the compositions and articles of the present invention is not exhaustive. Additional fabric care actives that are known and those that are yet to be known may also be used in the articles and compositions. There appears to be no limitation concerning the types of active materials that may be delivered to a laundry solution via the articles of the present invention provided that the actives may be releasably contained in an article or dose form and that the active alone or in combination with other material(s) may be at least partially distributed in the laundry solution. More specifically, fabric care actives may include any organic compound that is capable of delivering a desired fabric care benefit, provided that the organic compound has a ClogP greater than about 1, more preferably greater than about 2.5, and even more preferably greater than about 3. Further, where the potential active consists of a mixture of organic compounds, at least about 25%, more preferably at least about 50%, and even more preferably at least about 75% by weight of that mixture will have a ClogP greater than about 1, more preferably greater than about 2.5, and even more preferably greater than about 3.

Once dispensed in the laundry solution, the materials of the article should rapidly dissociate, dissolve, disperse and/or disintegrate in order to rapidly release the active or mixture of actives. The dissolution rate of the articles of the present invention should be rapid across a broad range of pH conditions so that the dissolution occurs rapidly in both the high pH solutions typically found in the wash and the relatively lower pH solutions (more neutral pH) typically found in the rinse. Further, the articles should rapidly disperse across a broad range of temperature conditions. This is particularly critical for articles that have been formulated to deliver an active to the rinse bath solution, where the solution temperatures will typically be found in a range between about 5° C. and about 30° C. Specifically, it is preferred that the articles have a dissolution rate between about 0.5 min and about 15 min in an aqueous bath at about 30° C. and more preferably between about 0.5 min and 6 min. Similarly, in an aqueous bath at about 10° C., it is preferred that the articles have a dissolution rate of between about 0.5 min and about 15 min, and more preferably between about 0.5 min and about 6 min.

The articles of the present invention may have a range of physical states, including but not limited to solids, waxy solids, pastes, liquids, slurries, dispersions, gels, foams, sprays and aerosols. Further, these materials may be encapsulated, molded, compacted, coated or applied to a substrate to form the unitized articles and dose forms. Solid forms of the articles will include or be comprised of powders, pellets, granules, tablets including but not limited to dimple tablets, bars, spheres, sticks, and virtually any other form that may be created through the use of compression or molding.

It is preferred that the articles of the present invention will be in the form of a capsule, tablet, pouch, sphere or envelope. A number of non-actives may optionally be included in the articles to facilitate their manufacture, processing, dispensing and dissociation. Further, the articles of the present invention may optionally include packaging to contain one or more fabric care articles.

B. Non-Actives

As noted above, the articles of the present invention may optionally include a number of non-actives that will aid in the manufacture, processing, dispensing, dispersing and dissociation of the articles and the release of the actives that they contain. These optional non-actives include but are not limited to, dispersion agents, disintegration agents, carriers, substrates, binders, mold release agents, emulsifiers, identification means, and more specifically, effervescent systems and foams.

1. Dispersion/Disintegration Agents

It is anticipated that some fabric care actives used in the compositions and articles of the present invention may be insoluble or only slightly soluble in water. Likewise, many fabric care actives are compressed or compacted into their dosing form or are delivered in the presence of zeolite and/or layered silicate builders. In these cases, the use of a disintegration, dissociation or dispersion agent is preferred to ensure an effective deposition of the fabric care active(s) on the fabrics.

Therefore, the compositions of the present invention can optionally contain dispersibility aids, e.g., those selected from the group consisting of mono-long chain alkyl cationic quaternary ammonium compounds, mono-long chain alkyl amine oxides, and mixtures thereof. These materials can either be added as part of the active raw material, or added as a separate component of the fabric care composition.

a) Mono-Alkyl Quaternary Ammonium Compounds

Mono-alkyl cationic quaternary ammonium compounds useful as dispersion agents in the present invention are, preferably, quaternary ammonium salts of the general formula:

$$[R^4N^+(R^5)_3]A^-$$

wherein $R^4$ is $C_8$–$C_{22}$ alkyl or alkenyl group, preferably $C_{10}$–$C_{18}$ alkyl or alkenyl group; more preferably $C_{10}$–$C_{14}$ or $C_{16}$–$C_{18}$ alkyl or alkenyl group; each $R^5$ is a $C_1$–$C_6$ alkyl or substituted alkyl group (e.g., hydroxy alkyl), preferably $C_1$–$C_3$ alkyl group, e.g., methyl (most preferred), ethyl, propyl, and the like, a benzyl group, hydrogen, a polyethoxylated chain with from about 2 to about 20 oxyethylene units, preferably from about 2.5 to about 13 oxyethylene units, more preferably from about 3 to about 10 oxyethylene units, and mixtures thereof; and $A^-$ is preferably a halide counterion.

Especially preferred dispersibility aids are monolauryl trimethyl ammonium chloride and monotallow trimethyl ammonium chloride available from Goldschmidt under the trade name Varisoft® 471 and monooleyl trimethyl ammonium chloride available from Goldschmidt under the tradename Varisoft® 417.

The $R^4$ group can also be attached to the cationic nitrogen atom through a group containing one, or more, ester, amide, ether, amine, etc., linking groups which can be desirable for increased concentratability. Such linking groups are preferably within from about one to about three carbon atoms of the nitrogen atom.

Mono-alkyl cationic quaternary ammonium compounds also include $C_8$–$C_{22}$ alkyl choline esters. The preferred dispersibility aids of this type have the formula:

$$R^1C(O)—O—CH_2CH_2N^+(R)_3A^-$$

wherein $R^1$, R and $A^-$ are as defined previously.

Highly preferred dispersibility aids include $C_{12}$–$C_{14}$ coco choline ester and $C_{16}$–$C_{18}$ tallow choline ester. Suitable biodegradable single-long-chain alkyl dispersibility aids containing an ester linkage in the long chains are described in U.S. Pat. No. 4,840,738, Hardy and Walley, issued Jun. 20, 1989.

Organic acids are described in European Patent Application No. 404,471, Machin et al., published on Dec. 27, 1990, supra, which is herein incorporated by reference. Preferably, the organic acid is selected from the group consisting of glycolic acid, acetic acid, citric acid, and mixtures thereof.

Ethoxylated quaternary ammonium compounds which can serve as the dispersibility aid include ethylbis(polyethoxy ethanol)alkylammonium ethyl-sulfate with 17 moles of ethylene oxide, available under the trade name Variquat® 66 from Goldschmidt; polyethylene glycol (15) oleammonium chloride, available under the trade name Ethoquad® 0/25 from Akzo; and polyethylene glycol (15) cocomonium chloride, available under the trade name Ethoquad® C/25 from Akzo.

b) Amine Oxides

Suitable amine oxides include those with one alkyl or hydroxyalkyl moiety of about 8 to about 22 carbon atoms, preferably from about 10 to about 18 carbon atoms, more preferably from about 8 to about 14 carbon atoms, and two alkyl moieties selected from the group consisting of alkyl groups and hydroxyalkyl groups with about 1 to about 3 carbon atoms.

Examples include dimethyloctylamine oxide, diethyldecylamine oxide, bis-(2-hydroxyethyl)dodecyl-amine oxide, dimethyldodecylamine oxide, dipropyl-tetradecylamine oxide, methylethylhexadecylamine oxide, dimethyl-2-hydroxyoctadecylamine oxide, and coconut fatty alkyl dimethylamine oxide.

Suitable polymeric dispersing agents include polymeric polycarboxylates and polyethylene glycols, although others known in the art can also be used. It is believed, though it is not intended to be limited by theory, that polymeric dispersing agents enhance overall detergent builder performance, when used in combination with other builders (including lower molecular weight polycarboxylates) by crystal growth inhibition, particulate soil release peptization, and anti-redeposition.

Polymeric polycarboxylate materials can be prepared by polymerizing or copolymerizing suitable unsaturated monomers, preferably in their acid form. Unsaturated monomeric acids that can be polymerized to form suitable polymeric polycarboxylates include acrylic acid, maleic acid (or maleic anhydride), fumaric acid, itaconic acid, aconitic acid, mesaconic acid, citraconic acid and methylenemalonic acid. The presence in the polymeric polycarboxylates herein or monomeric segments, containing no carboxylate radicals such as vinylmethyl ether, styrene, ethylene, etc. is also suitable provided that such segments do not constitute more than about 40% by weight.

Particularly suitable polymeric polycarboxylates can be derived from acrylic acid. Such acrylic acid-based polymers which are useful herein are the water-soluble salts of polymerized acrylic acid. The average molecular weight of such polymers in the acid form preferably ranges from about 2,000 to 10,000, more preferably from about 4,000 to 7,000 and most preferably from about 4,000 to 5,000. Water-soluble salts of such acrylic acid polymers can include, for example, the alkali metal, ammonium and substituted ammonium salts. Soluble polymers of this type are known materials. Use of polyacrylates of this type in detergent solutions has been disclosed, for example, in Diehl, U.S. Pat. No. 3,308,067, issued Mar. 7, 1967.

Acrylic/maleic-based copolymers may also be used as a preferred component of the dispersing/anti-redeposition agent. Such materials include the water-soluble salts of copolymers of acrylic acid and maleic acid. The average molecular weight of such copolymers in the acid form preferably ranges from about 2,000 to 100,000, more preferably from about 5,000 to 75,000, most preferably from about 7,000 to 65,000. The ratio of acrylate to maleate segments in such copolymers will generally range from about 30:1 to about 1:1, more preferably from about 10:1 to 2:1. Water-soluble salts of such acrylic acid/maleic acid copolymers can include, for example, the alkali metal, ammonium and substituted ammonium salts. Soluble acrylate/maleate copolymers of this type are described in European Patent Application No. 66915, published Dec. 15, 1982, as well as in EP 193,360, published Sep. 3, 1986, which also describes such polymers comprising hydroxypropylacrylate. Still other useful dispersing agents include the maleic/acrylic/vinyl alcohol terpolymers, such as are disclosed in EP 193,360, including, for example, the 45/45/10 terpolymer of acrylic/maleic/vinyl alcohol.

Another polymeric material which can be included is polyethylene glycol (PEG). PEG can exhibit dispersing agent performance as well as act as a clay soil removal, anti-redeposition agent and mold release agent. Typical molecular weight ranges for these purposes range from about 500 to about 100,000, preferably from about 1,000 to about 50,000, more preferably from about 1,500 to about 10,000.

2. Carriers

The compositions and articles of the present invention may optionally include a carrier for assisting in the manufacture and dispensing of the fabric care active. Further, the use of a carrier is well know to provide structural integrity to the article prior to its dispensing in a laundry solution. Preferred carrier materials may include foams, zeolites, gelatins, polyvinyl alcohols, polyvinyl pyrrolidone, hydroxypropylmethylcellulose, sugar, sugar derivatives, cyclodextrins, starch, starch derivatives and effervescent systems.

a) Effervescent Systems

The use of effervescent systems not only provides a preferred method for formulating the articles of the present invention, but also provides very rapid disintegration and dissolution of the article after it is dispensed in the laundry solution. Effervescents are a well known vehicle for delivering pharmacological products to a solution. However, prior to the present invention, their use in laundry applications has been limited to the delivery of detergent actives. The use of effervescents to deliver non-detergent actives to a cold water rinse bath solution is of particular value.

A simplified effervescent system will comprise an acid and carbonate source that will react in the presence of water to produce carbon dioxide within the article. The generation of carbon dioxide within article causes the article to rapidly disintegrate in all aqueous laundry solutions, releasing the active or mixture of actives to the solution. As is described in detail below, this disintegration and active release may be improved by increasing the rate of reaction between the acid and carbonate source. An effervescent system is particularly effective in promoting rapid dissolution of tablets and capsules under cold water conditions, e.g. less than 30° C.

A laundry article containing an effervescent system is a preferred embodiment of the present invention and is described in more detail below.

b) Foams

The articles of the present invention may include foams that are air-stable but instable when contacted with water, i.e. rapidly dissolve in water. These foam components may be in a particle form of a sponge-like structure, used as a binder within the article or in sheet form to encapsulate or coat the article. Regardless of form, a laundry article comprising a foam component is a preferred embodiment of the present invention and is described in detail below.

c) Other Carriers

In addition to effervescent systems and foams, a variety of materials may be used to complex with or encapsulate the fabric care actives used in the compositions and articles of the present invention. The use of cyclodextrins and zeolites was previously described as a preferred acrrier material for perfumes and other organic fabric care actives. Further, in the specific article forms described below, gelatins, polyvinyl alcohol, hydroxypropyl methylcellulose, polyvinyl pyrrolidone, sugars, sugar derivatives, starches and starch derivatives, and waxy polymers such as polyethylene glycols are preferably used as carrier materials.

3. Binders

The articles of the present invention may also include a binder for holding the components of the article to one another. The use of binders is particularly preferred where the article is in a solid form that is made through a manufacturing process that comprises a compression or compaction step. Preferred materials that may be used as binders in the article of the present invention are described in detail in conjunction with effervescent articles.

4. Emulsifying Agents

When an emulsifier is optionally included, the emulsifier may be any suitable emulsification or suspending agent. Preferably, the emulsifier is a cationic, nonionic, zwitterionic surfactant or mixtures thereof when the article is to be used to deliver actives to a rinse bath. Preferred emulsifiers are cationic surfactants such as the fatty amine surfactants and in particular the ethoxylated fatty amine surfactants. Examples of preferred nonionic emulsifying surfactants include surfactants selected from the group consisting of alkyl phenyl polyether, alkyl ethoxylates, polysorbate surfactants and mixtures thereof. Examples of preferred anionic emulsifying surfactants include surfactants selected from the group consisting of alkyl sulfate, alkyl benzene sulfonate, alkyl ether sulfate, and mixtures thereof.

By emulsifying surfactant is meant the surfactant added to the fabric care composition to disperse a hydrophobic fabric care active when it comes in contact with water. For example, when the fabric care active is a perfume, it is typically dispersed with the emulsifier or suspending agent in a ratio of emulsifier to active from 1:10 to 3:1.

a) Nonionic Surfactant

Conventional nonionic and amphoteric surfactants include C12–C18 alkylethoxylates (AE) including the so-called narrow peaked alkyl ethoxylates and C6 –C12 alkyl phenol alkoxylates (especially ethoxylates and mixed ethoxy/propoxy). The C10–C18 N-alkyl polyhydroxy fatty acid amides can also be used. Typical examples include the C12–C18 N-methylglucamides. See WO 9,206,154. Other sugar-derived surfactants include the N-alkoxy polyhydroxy fatty acid amides, such as C10–C18 N-(3-methoxypropyl) glucamide. The N-propyl through N-hexyl C12–C18 glucamides can be used for low sudsing. Examples of nonionic surfactants are described in U.S. Pat. No. 4,285,841, Barrat et al, issued Aug. 25, 1981.

Preferred examples of these surfactants include ethoxylated alcohols and ethoxylated alkyl phenols of the formula R(OC2 H4)n OH, wherein R is selected from the group consisting of aliphatic hydrocarbon radicals containing from about 8 to about 15 carbon atoms and alkyl phenyl radicals in which the alkyl groups contain from about 8 to about 12 carbon atoms, and the average value of n is from about 5 to about 15. These surfactants are more fully described in U.S. Pat. No. 4,284,532, Leikhim et al, issued Aug. 18, 1981. Particularly preferred are ethoxylated alcohols having an average of from about 9 to about 15 carbon atoms in the alcohol and an average degree of ethoxylation of from about 6 to about 12 moles of ethylene oxide per mole of alcohol. Mixtures of anionic and nonionic surfactants are especially useful.

Other conventional useful surfactants are listed in standard texts, including polyhydroxy fatty acidamides, alkyl glucosides, polyalkyl glucosides, C12–C18 betaines and sulfobetaines (sultaines). Examples include the C12–C18 N-methylglucamides. See WO 9,206,154. Other sugar-derived surfactants include the N-alkoxy polyhydroxy fatty acid amides, such as C10–C18 N-(3-methoxypropyl)glucamide.

b) Cationic Surfactants

One class of preferred cationic surfactants are the mono alkyl quaternary ammonium surfactants although any cationic surfactant useful in laundry compositions are suitable for use herein. The cationic surfactants which can be used herein include quaternary ammonium surfactants of the formula:

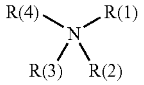

wherein R1 and R2 are individually selected from the group consisting of C1–C4 alkyl, C1–C4 hydroxy alkyl, benzyl, and —(C2 H4 O)x H where x has a value from about 2 to about 5; X (not shown) is an anion; and (1) R3 and R4 are each a C6–C14 alkyl or (2) R3 is a C6–C18 alkyl, and R4 is selected from the group consisting of C1–C10 alkyl, C1–C10 hydroxyalkyl, benzyl, and —(C2 H4 O)x H where x has a value from 2 to 5.

Preferred quaternary ammonium surfactants are the chloride, bromide, and methylsulfate salts. Examples of preferred mono-long chain alkyl quaternary ammonium surfactants are those wherein R1, R2, and R4 are each methyl and R3 is a C8–C16 alkyl; or wherein R3 is C8–18 alkyl and R1, R2, and R4 are selected from methyl and hydroxyalkyl moieties. Lauryl trimethyl ammonium chloride, myristyl trimethyl ammonium chloride, palmityl trimethyl ammonium chloride, coconut trimethylammonium chloride, coconut trimethylammonium methylsulfate, coconut dimethyl-monohydroxy-ethylammonium chloride, coconut dimethyl-monohydroxyethylammonium methylsulfate, steryl dimethyl-monohydroxy-ethylammonium chloride, steryl dimethyl-monohydroxyethylammonium methylsulfate, di-C12–C14 alkyl dimethyl ammonium chloride, and mixtures thereof are particularly preferred. ADOGEN 412.TM., a lauryl trimethyl ammonium chloride commercially available from Goldschmidt, is also preferred.

c) Amine Oxide Surfactants

The compositions herein also contain semi-polar nonionic amine oxide surfactants of the formula:

R1(EO)x(PO)y(BO)zN(O)(CH2R')2.multidot.qH2O (I)

In general, it can be seen that the structure (I) provides one long-chain moiety R1 (EO)x (PO)y (BO)z and two short chain moieties, CH2 R'. R' is preferably selected from hydrogen, methyl and —CH2 OH. In general R1 is a primary or branched hydrocarbyl moiety which can be saturated or unsaturated, preferably, R1 is a primary alkyl moiety. When x+y+z=0, R1 is a hydrocarbyl moiety having chainlength of from about 8 to about 18. When x+y+z is different from 0, R1 may be somewhat longer, having a chainlength in the range C12–C24. The general formula also encompasses amine oxides wherein x+y+z=0, R1=C8–C18, R' is H and q is 0–2, preferably 2. These amine oxides are illustrated by C12–14 alkyldimethyl amine oxide, hexadecyl dimethylamine oxide, octadecylamine oxide and their hydrates, especially the dihydrates as disclosed in U.S. Pat. Nos. 5,075,501 and 5,071,594, incorporated herein by reference.

The invention also encompasses amine oxides wherein x+y+z is different from zero, specifically x+y+z is from about 1 to about 10, R1 is a primary alkyl group containing 8 to about 24 carbons, preferably from about 12 to about 16 carbon atoms; in these embodiments y+z is preferably 0 and x is preferably from about 1 to about 6, more preferably from about 2 to about 4; EO represents ethyleneoxy; PO represents propyleneoxy; and BO represents butyleneoxy. Such amine oxides can be prepared by conventional synthetic methods, e.g., by the reaction of alkylethoxysulfates with dimethylamine followed by oxidation of the ethoxylated amine with hydrogen peroxide.

Highly preferred amine oxides herein are solids at ambient temperature, more preferably they have melting-points in the range 30° C. to 90° C. Amine oxides suitable for use herein are made commercially by a number of suppliers, including Akzo Chemie, Ethyl Corp., and Procter & Gamble. See McCutcheon's compilation and Kirk-Othmer review article for alternate amine oxide manufacturers. Preferred commercially available amine oxides are the solid, dihydrate ADMOX 16 and ADMOX 18, ADMOX 12 and especially ADMOX 14 from Ethyl Corp.

Preferred embodiments include dodecyldimethylamine oxide dihydrate, hexadecyldimethylamine oxide dihydrate, octadecyldimethylamine oxide dihydrate, hexadecyltris(ethyleneoxy)dimethyl-amine oxide, tetradecyldimethylamine oxide dihydrate, and mixtures thereof. Whereas in certain of the preferred embodiments R' is H, there is some latitude with respect to having R' slightly larger than H. Specifically, the invention further encompasses embodiments wherein R' is CH2OH, such as hexadecylbis(2-hydroxyethyl)amine oxide, tallowbis(2-hydroxyethyl)amine oxide, stearylbis(2-hydroxyethyl)amine oxide and oleylbis(2-hydroxyethyl) amine oxide.

5. Identification Means

It is anticipated that the articles of the present invention will have identification means such as a tactile or preferably a visual indicator. Visual indicators may be used to distinguish between fabric care articles according to the fabric care actives or mixtures of actives that they contain. In addition, identification means may be used to indicate whether the article should be dispensed in a wash and/or rinse bath solution and further whether the article should be dispensed in a solution containing other materials such as detergent or fabric softeners actives. The visual indicators used in the articles of the present invention are preferably dyes or other coloring agents that are added to the article materials during manufacture or applied to the outer surface of the article after manufacture. Likewise, the visual indicator may also comprise distinct sizes and shapes, as well as the opacity, clarity or pearlescense of various articles. Likewise, visual indicators may also comprise words, letters, numbers, symbols or other codes that are printed, embossed, debossed, molded or imprinted on the surface of an article. Further, it is anticipated that identification means will utilize combinations and mixtures or these various visual indicators in the compositions and articles of the present invention.

6. Other Non-Actives

The articles of the present invention, particularly solid articles, may optionally comprise other non-active materials that provide the article with a moisture barrier or protective coating for protecting the article following its manufacture and prior to its dispensing in a laundry solution. Similar to the other non-actives, materials included as moisture barriers and protective coatings should be at least partially water-soluble such that the dissociation of the article in an aqueous laundry solution is not inhibited.

C. Specific Article Forms

1. Encapsulated Forms

Encapsulates are a preferred embodiment for the laundry articles of the present invention because they may contain the fabric care additive compositions in virtually any form including but not limited to solids, waxy solids, pastes, liquids, slurries, dispersions, and foams. An encapsulated article of the present invention comprises an outer coating or film that is at least partially water soluble such that upon contact with an aqueous laundry solution, the outer coating or film will rapidly dissolve away providing for the release of the fabric care additive composition contained within.

The water soluble film or coating used to encapsulate the fabric care compositions and articles of the present invention will preferably be formed from hard and soft gelatins, polyvinyl alcohol, hydroxpropylmethylcellulose, polyvinyl pyrrolidone, sugar, sugar derivatives, starch, starch derivatives, zeolites, effervescent systems, foams, and mixtures thereof. The composition of the encapsulated articles and the methods of making and using them may vary somewhat based upon the type(s) of the encapsulating material that are used.

a) Gelatin Based Capsules

The fabric care compositions of the present invention may be contained in articles that comprise gelatin based capsules. The capsule materials useful with the present invention include hard and soft gelatin capsules as well as starch capsules which are discussed in more detail below. The hard and soft gelatin capsules are made from gelatin as fully discussed in The Theory and Practice of Industrial Pharmacy, Lachman et al., Lea & Febiger, p. 374–408 (3d Ed. 1986). The gelatin is a heterogeneous product derived by irreversible hydrolytic extraction of treated animal collagen from such sources as animal bones, hide portions, and frozen pork skin. The gelatin can be blended with plasticizers, and water.

Gelatin material can be classified as Type A gelatin, which is obtained from the acid-processing of porcine skins and exhibits an isoelectric point between pH 7 and pH 9; and Type B gelatin, which is obtained from the alkaline-processing of bone and animal (bovine) skins and exhibits an isoelectric point between pH 4.7 and pH 5.2. Blends of Type A and Type B gelatins can be used to obtain a gelatin with the requisite Viscosity and bloom strength characteristics for capsule manufacture. Gelatin suitable for capsule manufacture is commercially available from the Sigma Chemical Company, St. Louis, Mo. For a general description of gelatin and gelatin-based capsules, see Remington's Pharmaceutical Sciences, 16th ed., Mack Publishing Company, Easton, Pa. (1980), page 1245 and pages 1576–1582; and U.S. Pat. No. 4,935,243, to Borkan et at., issued Jun. 19, 1990. Both Type A and B gelatins may be used in the articles of the present invention but Type B is preferred.

A plasticizer will serve to prevent mass transfer between the capsule and the filler. Plasticizers will typically include sorbitol, mannitol, glycerine, propylene glycol, and sugar compounds such as sucrose, glucose, fructose, lactose and similar sugar compounds. The plasticizer is typically present in an amount of from about 0.5 to about 50, preferably from about 0.5 to about 30, and more preferably from about 1 to about 10, weight percent of the capsule wall. When the plasticizer is glycerine, the ratio of glycerine to gelatin is typically from about 0.1:1 to about 0.8:1 for the hard and soft gelatin capsules, respectively.

The moisture content for hard gelatin capsules ranges from about 10–16% and from about 5–12% for soft gelatin capsules at a relative humidity of about 25% at about 22° C. The gelatin capsules can also contain such additives as preservatives, colorants, etc. Commercially available gelatin capsules are those made by CAPSUGEL, a division of Warner-Lambert Co., which are available in a general capsule size range of from #5 to #000 having volumes of from about 0.1–1.4 ml.

Polyethylene glycol (PEG) is commonly incorporated into gelatin capsule filling materials to promote compatibilty with the capsule. The PEG component typically has a weight average molecular weight of from about 200 to about 1200 and commercially available PEG materials include PEG 200, PEG 300, PEG 400, PEG 540, PEG 600, PEG 800, and PEG 1000 all available from, for example, Union Carbide Corp.

Various methods are well known for sealing gelatin capsules halves. These methods include heat sealing processes wherein a band of gelatin, adhesive or solvent is applied to the overlapping portions of the two capsule halves and heat or steam is applied. In addition, various mechanical sealing methods have likewise been developed using interlocking formations on the two capsule halves to make a mechanical seal that may be augmented by the use of heat to fuse the formations. Sealing of the entire band or seam between capsule halves is particularly desirable when a liquid or free flowing powder fabric care composition is to be encased in the capsule. Alternatively, the capsules of the present invention may be sealed by substantially covering the filled capsule with another material such as by dipping the sealed capsules in a solution of an organic solvent of a natural or synthetic "binding agent", e.g., acrylic resins, polyvinyl acetates, polyvinyl pyrrolidone, cellulose acetate phthalate, cellulose ethers, alginates, etc. Care should be taken when using sealing methods that employ heat, humidity or fluids to avoid weakening the gelatin capsule walls.

Examples of soft gelatin capsules of the present invention are presented in Table A which were prepared encapsulating liquid perfume compositions. The capsules were made, filled and sealed using conventional techniques and equipment. The amounts listed in Table A represent the weight percentages of the various components. Examples I–IV and VI were made into spherical articles having a diameter of about 3 mm, 5 mm, 15 mm, 6.5 mm, and 15 mm respectively. Example V was a twist off capsule having a tear drop shape.

Example I was made by a submerged nozzle encapsulation method wherein the fill and capsule shell materials were coextruded through concentric tubes to form spheres and solidify. See "Submerged Nozzle Encapsulation Technology", Marshall et al., available from Southwest Research Institute, San Antonio, Tex. Example IV was made by concentric nozzle extrusion wherein the fill and capsule shell materials were coextruded through concentric tubes to form spheres, solidified by dropping into a cold medium (e.g. cold hydrocardons). Examples II, III, V and VI were made by the standard soft capsule production methods including continuous gelatin-film molding wherein two continuous gelatin films are fed to the top of a rotary die, fill material is fed into a pocket formed by the die and heat is used to seal the films and entrap the fill material. Continuous gelatin-film molding is practiced in the United States by R.P. Scherer Corporation and Banner Gelatin Products Corp. It is anticipated that the encapsulates of the present invention may be made by other conventional encapsulation methods provided that the capsule shell is able to contain a variety of the fill materials disclosed herein without rupture or leakage.

Although not reflected in Table A, the capsule walls may contain between about 5% and about 15% residual water.

TABLE A

| | Example | | | | | |
|---|---|---|---|---|---|---|
| | I | II | III | IV | V | VI |
| Gelatin 250 | 8.5 | — | — | — | — | — |
| Gelatin 150 | — | 11.8 | 11.8 | — | 11.8 | 11.8 |

TABLE A-continued

| | Example | | | | | |
|---|---|---|---|---|---|---|
| | I | II | III | IV | V | VI |
| Gelatin 300 | — | — | — | 14.0 | — | — |
| Sorbitol | 1.5 | — | — | — | — | — |
| Glycerine | — | 2.9 | 2.9 | 6.0 | 2.9 | — |
| Perfume | 90.0 | 85.3 | 85.3 | 80.0 | 85.3 | 42.6 |
| Neodol 91-8 | — | — | — | — | — | 42.7 |

b) Non-Gelatin Encapsulates/Forms

1) Polyvinyl Alcohol Film Encapsulates

Capsules and encapsulates made of films and sheets of PVA and HPMC are preferred articles of the present invention. These polymers may be purchased in film form to simplify the encapsulation process. The fabric care composition may comprise only the chosen fabric care active or mixture of actives. Where the fabric care active is insoluble or only partially water soluble, one or more of the optional non-active ingredients discussed herein may be included. By way of example, most perfumes are organic in nature and tend not to go into the aqueous laundry solutions, but rather will float to the top of the bath after release from the fabric care article. As such it is preferred to include an emulsifier or carrier to aid in dispersing the perfume in the solution.

EXAMPLE VII

Preparation of HPMC Encapsulate

Neodol 91-8 and perfume were mixed in a beaker and stirred with a spatula until homogeneous. Two pieces of hydroxypropyl methlycellulose film (available from Chris Craft Ind., Inc.) were cut into sections approximately 1.5 inches square. The pieces were heat sealed on three sides using a conventional heat sealer, to form a pouch or envelope. Approximately 2 g of the perfume-Neodol mixture was added to the pouch and the fourth side was heat sealed to enclose the mixture. The weight percentages of these components in the final product are presented in Table B.

TABLE B

| Component | Order of Addition | Weight % |
|---|---|---|
| Neodol 91-8 | 1 | 43.67 |
| Perfume | 2 | 43.67 |
| Hydroxypropylmethylcellulose | 3 | 12.66 |

Highly water-soluble capsules containing fabric care actives can be prepared by a variety of methods. Water-soluble materials in film form are particularly useful in such methods. Preferred films will include those films that are highly water-soluble having fast dissolution rates in water less than about 30° C., and even more preferably in water less than about 10° C. By selecting films with these dissolution properties the final article will rapidly dissolve when dispensed in both cold water wash and rinse bath solutions. It is also preferred that the film or capsule shell materials useful in the present invention be thermoplastic or thermosetting polymers to facilitate the sealing of filled encapsulates if heat sealing is to be used. Specific film materials that are particularly preferred for use in preparing the articles of the present invention include polyvinyl alcohol and hydroxypropyl methylcellulose.

In one encapsulation method, a water soluble film is placed over a mold. The mold may have a variety of shapes but is preferably spherical or oval. The film is then deformed so that it conforms to the internal shape of the mold and may be filled with a fabric care active or mixture of actives. A second segment of water soluble film is then placed over the filled mold and the two film segments are sealed together by heat seal, adhesive, partially solvating the two films or other conventional means. Many of the methods for sealing gelatin based capsules described previously, have application to the sealing of non-gelatin water soluble films as well.

In an alternative method, a water-soluble film is placed in an apparatus having a rotary die as is described in WO97/35537. Two continuous film segments are fed into the rotary die and placed over oppositely oriented molds, the segments are deformed by drawing a vacuum. The two halves are then filled with a fabric care active and the film segments are at least partially solvated about the edges of the molds so that they seal to one another when the two halves are pressed together.

EXAMPLES VIII–IX

Preparation of PVA and HPMC Capsules

In Examples VIII and IX presented in Table C, the fill material consisted of a mixture of perfume and Neodol 91-8 and the polyvinyl alcohol spherical capsules were made by the aforementioned encapsulation process described in WO97/35537.

In yet another example, a mixture of perfume and Neodol 91-8 (1:1 wt. Ratio) was sealed in a hemispherical capsule made of a water soluble polyvinyl alcohol film (Mono-sol 8630 made by Chris Craft Industries, Inc.). The film was deformed by vacuum, filled without about 10 cc of perfume/Neodol mixture and a second segment of polyvinyl alcohol film was placed over the mold and the two film sections were heat sealed with a pressure plate at about 300° F. for about 2 seconds at a pressure of about 70 psig. The final product was a generally hemispherical capsule containing the fabric care active. Excess film about the seal was trimmed away to improve the aesthetics of the capsulate.

Although not reflected in Table C, the capsule walls can contain from about 5% to about 15% residual water.

TABLE C

| | Example | | | |
|---|---|---|---|---|
| | VIII | IX | X | XII |
| Polyvinyl alcohol | 2.5 | — | 2.5 | 2.5 |
| Hydroxypropyl methylcellulose | — | 2.5 | — | — |
| Glycerine | 0.3 | 0.3 | 0.3 | 0.30 |
| Neodol 91-8 | 48.6 | 48.6 | — | |
| Decamethyl-cyclopentane siloxane (D5) | — | — | 58.3 | — |
| Perfume in Zeolite* | — | — | 38.9 | 38.9 |
| Perfume | 48.6 | | — | 58.3 |

*Perfume loading of Zeolite 13X is about 15%.

2) Sugar/Sugar Derivative Capsules

Sugar and sugar derivative encapsulates are well known for their use in the pharmacological field for the oral delivery of medicaments. The use of a hollow shell to contain a liquid center is well known in this art. For instance, the teachings of Liebich, U.S. Pat. No. 943,945, disclose a hollow or empty body preferably made of sugar, enveloped or encased in an edible substance such as biscuit, chocolate, cake or sugar, which contained a liquor therein. Similarly, Silver, U.S. Pat. No. 2,531,536, teaches a liquid containing product but is more specifically concerned with a “flavor-bud” comprising a hard shell made of, among other things, a sizable quantity of anhydrous dextrose and some glucose, and a viscous liquid flavored center. Kreuger et al., U.S. Pat. No. 2,580,683, describes a capsule, capable of being filled with an aqueous solution, containing sugar in the gelatin employed to form the capsule. In describing a unit dosage form of liquid or gel, Mackles, U.S. Pat. No. 4,260,596, discloses a hard shell formed of two pieces, a cavity and a top, joined with a sealing material, encompassing a liquid or gel center, said shell utilizing mannitol rather than sugar as the shell forming ingredient.

The sugar encapsulated articles of this invention comprises a water soluble unit dosage form for delivering a unitized amount of fabric care active or mixture of actives, comprising a relatively hard outer shell which is essentially comprised of a sugar which crystallizes slowly from the melt, said sugar comprising sucrose, glucose or mixtures thereof, and a liquid, semi-solid or solid center contained within the shell comprising a dose of a fabric care active.

The outer shell described herein is essentially composed of sugar taken from the group of sugars comprising essentially sucrose, glucose, lactose starch derivative sucrose derivatives and mixtures thereof, and may include optional additive ingredients such as dyes, plasticizers, anti-agglomeration agents such as disintegration agents and dissolution agents, and mixtures thereof. The optional plasticizers include sorbitol, polyethylene glycol, propylene glycol, low molecular weight carbohydrates and the like with a mixture of sorbitol and polyethylene glycol and low molecular weight polyols being the most preferred. The anti-agglomeration agents are preferably a surfactant and are included at low levels. A suitable surfactant for use in the articles of the present invention is TWEEN 80.TM. commercially available from Imperial Chemicals, Inc. (ICI).

The sugar encapsulates of the present invention may be made using conventional methods and equipment. One such method comprises simultaneous injection of the materials forming the outer shell and the fabric care composition in side by side injector alignment, into a mold, provided that the fabric care composition has a moisture content equal to or below that of the shell composition. The regulation of the component moisture contents allows simultaneous injection of the components into a mold without an intermixing of the components. Such a simultaneous injection method is described in U.S. Pat. No. 4,929,446.

An alternative method for producing sugar derivative encapsulates is described in U.S. Pat. No. 4,260,596. As described, the outer shell for the dosage of fabric care active is formed by pouring molten mannitol or mannitol composition into the hemispheric cavities of a chilled mold. The molten mannitol quickly solidifies, proceeding from the surface of the cavity mold toward the interior of the hemisphere. After a sufficiently thick wall has been formed, the remaining mannitol still in liquid or fluid form is withdrawn leaving a shaped hemisphere comprising crystalline mannitol. The thickness of the hemisphere wall can varied depending on the results desired but generally, it will be in the range of from about 0.5 to about 3.0 mm and preferably in the range of from about 1.0 to about 1.5 mm. The thickness of the shell wall can be controlled by varying the temperature of the mold at the time the molten mannitol or mannitol composition is introduced and by varying the time during which the mold cavity is filled with molten mannitol. Ordinarily, the temperature of the mold at the time it is filled with the molten mannitol will be in the range of from about 15 to about 30° C. and the time elapsed between the filling of the mold and the removal of excess fluid material will usually be in the range of from about 1 to about 5 seconds.

After the shell is made, a liquid, gel or solid fabric care composition is introduced into the shell. Since the mannitol is water soluble, the fabric care composition is preferably an oil base product or a water-in-oil emulsion. Along with the fabric care actives, other suitable additives may be incorporated, such additives including solvents, mineral and vegetable oils, emulsifiers, etc. Likewise, it is sometimes desirable to modify the mannitol shell and materials such as glycerin, sorbitol, propylene glycol, colorants, sugars, etc. may also be incorporated in the shell.

After the fabric care composition has been introduced into the shell, it is necessary to seal off the top of the shell. It has been found that this may readily be accomplished by melting certain water soluble materials and pouring them into the opening in the shell. The materials that are selected for this purpose float on the fabric care composition that fills the shell. Upon cooling, these materials form a roof for the shell and at the same time, form a seal around its periphery with the side walls of the shell. A variety of materials are known in the prior art which may be used in this procedure. By way of example, Carbowax 4000 (CTFA name PEG-75), Carbowax 6000 (CTFA name PEG-150), mannitol, sorbitol and/or mixtures of these materials. Also, these materials may be mixed with glycerin, propylene glycol, butylene glycol, colorants, sugars, etc.

3) Starch/Starch Derivative Encapsulates

The incorporation of many fabric care actives is facilitated by first encapsulating the active in a binder or carrier material. For instance, the delivery of a perfume composition may be facilitated by encapsulating the perfume in a starch or zeolite. Examples X and XI were prepared using perfume as the fabric care active. In their preparation, the perfume oil was added to a 25% modified starch solution with the balance being water. The oil was added to the starch at a rate 1 g/sec with high agitation. The agitation was provided by an efficient homogenizer to form an emulsion having an oil droplet size of less than about 2 micrometers. The emulsion was then spray dried in a co-current tower having an air inlet temperature of about 200° C. and an outlet temperature of about 100° C. to yield a dry particle with a mean particle size of about 58 micrometers.

Once encapsulated, the fabric care actives can be incorporated in a variety of article forms such as effervescent articles, foam containing articles, capsules or beads and various other macro-encapsulates.

TABLE D

| | Examples | |
|---|---|---|
| | X | XI |
| Perfume | 40.2 | 13.04 |
| HICAP 100-Modified Starch* | 57.8 | — |
| Water | 2.0 | — |
| Zeolite 13X | — | 86.96 |

*Available from National Starch & Chemical

4) Zeolite Containing Encapsulates

A zeolite containing encapsulate is prepared by first combining a fabric care active with the selected zeolite as described above with respect to the incorporation of perfumes.

EXAMPLE XI

Zeolite/Perfume Complex

The zeolite is first activated by drying it overnight in an oven at 130° C. under reduced pressure of less than 30 mm Hg. The weight loss due to drying was approximately 5 g/kg of zeolite material. One hundred grams of zeolite was then placed in a beaker with 15 g of perfume active. These materials were stirred in the beaker with a glass rod until there was uniformity in the mixture at which point the mixture was giving off a small amount of heat. The mixture was then transferred to a glass blender and mixed for 1 minute at which point the heat coming from the mixture was very noticeable. Alternative mixers and grinders may be used at this stage, but devices having plastic elements should be avoided as the perfume may react or be absorbed into or degrade the plastic.

The amount of perfume in the perfume loaded zeolite was 13%.

2. Effervescent Articles

The articles of the present invention may also have an effervescence system or component comprising an acid source and a carbon dioxide source. To improve the effervescing properties of the article in a laundry solution it is most preferable that the acid and carbon dioxide source have a particle diameter from about 0.1 to about 150 microns, and more preferably from about 0.5 to about 100 microns. It is also preferred that the acid source and the carbon dioxide source are present in an intimate mixture with one another, preferably in an effervescent granule. These effervescent granules may be used to prepare solid articles of the present invention in the form of tablets, spheres, bars and most any moldable shape.

The acid source used in the effervescent components is a particulate material that is first ground to obtain the acid source of the invention, prior to mixing with the carbon dioxide source. The carbon dioxide source may also be obtained by grinding larger particle size material.

a) Acid Source

Suitable acid sources herein are capable of providing solid organic, mineral or inorganic acids, and the sources are thereto preferably in the form of acids, salts or derivatives thereof or a mixture thereof. Derivatives in particular include ester of the acids.

In particular organic acids are preferred. It may be preferred that the acids are mono-, bi- or tri-protonic acids. Such preferred acids include mono- or polycarboxylic acids preferably citric acid, adipic acid, glutaric acid, 3 cetoglutaric acid, citramalic acid, tartaric acid, maleic acid, fumaric acid, maleic acid, succinic acid, malonic acid. Such acids are preferably used in their acidic forms, and it may be preferred that their anhydrous forms are used, or mixtures thereof. Other preferred acids include sulphonic acids such as toluenesulphonic acid.

Surprisingly, it has now been found that by using citric acid, tartaric acid, maleic acid and/or malic acid, an improved physical and/or chemical stability upon prolonged storage periods is achieved. Furthermore, it has been found that these materials, in particular tartaric acid have an improved dissolution, resulting in an improved effervescence performance.

The acid source and preferably the acid itself is a particulate compound whereof at least 75%, preferably at least 85% or even at least 90% or even at least 95% or even at least 99% by volume, has a particle size from 0.1 to 150 microns and more preferably from 0.5 to 100 microns and it may even be preferred that at least 65% or even at least 75% or even at least 85% has a particle size from 1.0 to 75 microns or even from 1.0 to 55 microns or even from 1.0 to 25 microns. The particle size of the acid source and the carbon dioxide source described hereinafter, can be determined by any method known in the art, in particular by laser light scattering or defraction technique, such as with Malvem 2600 or Sympatec Helos laser light scattering equipment (or defractometer).

It may herein be preferred that the acid source has a volume median particle size of between 1 to 120 microns or even between 5 to 75 microns or even between 5 to 55 microns or even from 5 to 30 microns. The volume median particle size of the acid source and the carbon dioxide source can be determined by any method known in the art, in particular herein by use of the laser light scattering equipment mentioned herein, which is programmed to provide the volume median particle size.

The acid source herein is preferably obtained by grinding or milling coarse acid source material, having a larger particle size than the acid source herein, just prior to incorporation into the effervescence component. Namely, it has been found that handling of the fine particle size acid sources herein after storage may incur problems, and therefor it may be advantages to store the acid source in a coarser form and ground this material prior to use.

b) Carbon Dioxide Source

Another essential feature of the present invention is a carbon dioxide source. When used herein, carbon dioxide source includes any material that can provide carbon dioxide when reacting with an acid source upon contact with water. The carbon dioxide source includes carbonate, bicarbonate and percarbonate salts or mixtures thereof, however, bicarbonate and/or carbonate are most preferred.

Suitable carbonates to be used herein include carbonate and hydrogen carbonate of potassium, lithium, sodium, and the like amongst which sodium and potassium carbonate are preferred. Suitable bicarbonates to be used herein include any alkali metal salt of bicarbonate like lithium, sodium, potassium and the like, amongst which sodium and potassium bicarbonate are preferred. Bicarbonate may be preferred in combination with or as an alternative to carbonate, because it is more weight effective. However, the choice of carbonate or bicarbonate or mixtures thereof in the dry effervescent granules may be made depending on the pH desired in the aqueous medium wherein the dry effervescent granules are dissolved. For example, in a wash solution where a relative high pH is desired in the aqueous medium (e.g., above pH 9.5) it may be preferred to use carbonate alone or to use a combination of carbonate and bicarbonate wherein the level of carbonate is higher than the level of bicarbonate, typically in a weight ratio of carbonate to bicarbonate from 0.1 to 10, more preferably from 1 to 5 and most preferably from 1 to 2.

The carbon dioxide source has preferably a volume median particle size from 5 to 375 microns, whereby preferably at least 60%, preferably at least 70% or even at least 80% or even at least 90% by volume, has a particle size of from 1 to 425 microns. More preferably, the carbon dioxide source has a volume median particle size of 10 to 250, whereby preferably at least 60%, or even at least 70% or even at least 80% or even at least 90% by volume, has a particle size of from 1 to 375 microns; or even preferably a volume median particle size from 10 to 200 microns, whereby preferably at least 60%, preferably at least 70% or even at least 80% or even at least 90% by volume, has a particle size of from 1 to 250 microns.

The carbon dioxide source has a particle size similar to the acid source, preferably such that at least 60% or even 75% of the carbon dioxide source has a particle size from 1 to 150 microns. Preferably, the carbon dioxide source has a volume median particle size of between 1 to 120 microns, but is more preferably at least 60% or even 75% of the source having a particle size from 1 to 100 microns, having a volume median particle size of from 5 to 75, or even preferably at least 60% or even 75% of the source having a particle size of from 1.0 to 75 microns or even from 1.0 to 55 microns or even form 1.0 to 25 microns.

Likewise, a carbon dioxide source having a desired particle size may be obtained by grinding a larger particle size material, optionally followed by selecting the material with the required particle size by any suitable method.

c) Effervescent Granule

The acid source and carbon dioxide source, or at least part thereof are preferably present in an intimate mixture with one another, which means the acid source and carbon dioxide source are homogeneously mixed. Thus, in one preferred embodiment, at least part of the acid source and at least part of the carbon dioxide source are not separate discrete particles. The intimate mixing should result in the acid source and the carbon dioxide source being formed into a preferably dry effervescence granule. By "dry" it is to be understood that the granule is substantially free of water, i.e., that no water has been added or present other than the moisture of the raw materials themselves. Typically, the level of water is below 5% by weight of the total intimate mixture or granule, preferably below 3% and more preferably below 1.5%.

The acid is preferably present in the intimate mixture or the effervescent granules at a level of from 0.1% to 99% by weight of the total granule, preferably from 3% to 75%, more preferably from 5% to 60% and most preferably from 15% to 50%. The carbon dioxide source is preferably present in the intimate mixture or the effervescent granules at a level of from 0.1% to 99% by weight of the total, preferably from 30% to 95%, more preferably from 45% to 85% and most preferably from 50% to 80%.

It may be preferred that an optional desiccant be present in the intimate mixture or the effervescence granule, such as ovendried inorganic and organic salts, anhydrous salts, in particular overdried silicates and aluminosilicates, anhydrous silicates and/or sulphate salts.

For optimum effervescence in aqueous medium the weight ratio of acid source to carbon dioxide source in the intimate mixture or the effervescent granule is preferably from 0.1 to 10, preferably from 0.5 to 2.5 and more preferably from 1 to 2.

The effervescent granules are preferably obtainable by a process comprising a granulation step, preferably comprising the step of dry-powder compaction or pressure agglomeration. While all binding mechanisms can occur in pressure agglomeration, adhesion forces between the solid particles, i.e., between the acid, carbon dioxide source and optionally the binder if present, play an especially important role. This is because pressure agglomeration, especially high pressure agglomeration, is an essentially dry process that forms new entities (i.e., dry effervescent granules) from solid particles (i.e., the acid, bicarbonate, carbonate source and optionally the binder) by applying external forces to densify a more or less defined bulk mass or volume and create binding mechanisms between the solid particles providing strength to the new entity, i.e. the high external force applied brings the solid particles closely together. The inventors have surprisingly found that in the present invention reduced pressure may be sufficient to form a stable granule incorporating the small particle size acid source, with preferably small particle size carbon dioxide source as defined above.

The effervescent granules may have any particle size, the preferred particle size depending on the application and the component of the granule. For instance, it has been found that effervescence particles having a weight average particle size from 500 microns to 1500 microns whereby preferably at least 70% or even at least 80% by weight of said granule has a particle size from 350 to 2000 microns, or even having a weight average particle size from 650 microns to 1180 microns whereby preferably at least 70% or even 80% by weight of said granule has a particle size from 500 to 1500 microns, or even having a weight average particle size from 710 microns to 1000 microns whereby preferably at least 70% or even 80% by weight of said granule has a particle size from 600 to 1180 microns can provide improved dispensing/dissolution.

Similarly, it has been found that effervescence particles of a weight average particle size from 200 microns to 500 microns whereby preferably at least 70% of said granule has a particle size from 100 to 710 microns, or even having a weight average particle size from 250 microns to 450 microns whereby preferably at least 70% of said granule has a particle size from 150 to 650 microns, can provide better dispensing and/or dissolution of the composition than larger effervescence particles.

The weight average particle size of the effervescence granule herein and the detergent granules herein after can be determined by any method known in the art, in particular by sieving a sample of the particulate acid relevant material herein through a series of sieves, typically 5, with meshes of various diameter or aperture size, obtaining a number of fraction (thus having a particle size of above, below or between the mesh sizes of the used sieve sizes), whereof the weight is determined (weight fractions). The average particle size per fraction and then the weight average particle size of the material can be calculated, taking in account the weight percentage per fraction (e.g. plotting the weight fractions against the aperture size of the sieves).

The effervescent component of the articles of the present invention may optionally comprise a binder or a mixture of binders. Any binder material known in the art can be used. For example highly suitable are materials that have a melting point above 40C, put preferably below 200 C or 100 C. In general, suitable binders to use herein are those known to those skilled in the art and include anionic surfactants like C6–C20 alkyl or alkylaryl sulphonates or sulphates, preferably C8–C20 aklylbenzene sulphonates, fatty acids, cellulose derivatives such as carboxymethylcellulose and homo- or co-polymeric polycarboxylic acid or their salts, nonionic surfactants, preferably C10–C20 alcohol ethoxylates containing from 5–100 moles of ethylene oxide per mole of alcohol and more preferably the C15–C20 primary alcohol ethoxylates containing from 20–100 moles of ethylene oxide per mole of alcohol. Of these tallow alcohol ethoxylated with 25 moles of ethylene oxide per mole of alcohol (TAE25) or 50 moles of ethylene oxide per mole of alcohol (TAE50) are preferred. Other preferred binders include the polymeric materials like polyvinylpyrrolidones with an average molecular weight of from 12,000 to 700,000 and polyethylene glycols with an average weight of from 600 to 10,000. Copolymers of maleic anhydride with ethylene, methylvinyl ether, methacrylic acid or acrylic acid are other examples of polymeric binders. Others binders further include C10–C20 mono and diglycerol ethers as well as C10–C20 fatty acids.

It may be preferred that the effervescence component optionally comprise a coating agent, which can be selected from any coating agent known in the art. Preferred coating agents are materials that can be applied to the granule in the form of a melt, which is solid under ambient conditions. Such coating agents will include polymeric materials and nonionic surfactants. These materials may be also used as binding agents, described herein. Also preferred may be coating agents that can be applied to the granules in the form of an aqueous solution or a solution in an organic solvent, including organic and inorganic acids or salts. Furthermore, the granules may also be coated by dusting a particulate material such as a desiccant onto the granule.

d) Process for Manufacturing the Effervescent Component

A process for manufacturing the effervescent component for use in the articles of the present invent preferably comprises the steps of:

first obtaining the acid source of the particle size defined herein, preferably by grinding larger particle size acid source material as commercially available, mixing the thus obtained acid source with the carbon dioxide source, preferably by grinding larger particle size acid source material as commercially available, and optionally mixing a binder and/or other ingredients, to form a mixture, and then submitting the mixture to a granulation step, preferably comprising the step of extrusion, spheronisation, more preferably compaction or agglomeration.

Optionally, other ingredients an be added to the obtained granule, such as coating agents.

By “granulation step” it is meant that the resulting mixture is made into granules of the required size as defined herein before.

A preferred process to be used herein is roller compaction. In this process the acid and carbon dioxide sources and optionally the binder and other ingredients, after having been mixed together, are forced between two compaction rolls that applies a pressure to said mixture so that the rotation of the rolls transforms the mixture into a compacted sheet/flake. This compacted sheet/flake is then granulated. One way to carry this out is to mill the compacted flake/sheet or to granulate the agglomerate mixture by conventional means. Milling may typically be carried out with a Flake Crusher FC 200® commercially available from Hosokawa Bepex GmbH. Depending on the end particle size desired for the effervescent granules the milled material may further be sieved. Such a sieving of the dry effervescent granules can for example be carried out with a commercially available Alpine Airjet Screen®.

According to this process the effervescent raw materials and optionally the binder if present are preferably mixed together without the addition of water and/or moisture apart those coming from the raw materials themselves so as to obtain a dry free flowing powder mixture. Then this dry free flowing powder mixture comprising the effervescent particles (i.e. the acid and carbon dioxide source), and optionally the binder particles if present, undergoes a granulation step, preferably including a pressure agglomeration step, i.e. a dry process step wherein this free flowing powder mixture undergoes high external forces that bring the particles closely together thereby densifying the bulk mass of said particles and creating binding mechanisms between the solid effervescent particles and the binder if present.

Typical roller compactors for use herein is for example Pharmapaktor L200/50P® commercially available from Hosokawa Bepex GmbH. The process variables during the pressure agglomeration step via roller compaction are the distance between the rolls, the feed rate, the compaction pressure and the roll speed. Typical feeding device is a feed screw. The distance between the rolls is typically from 0.5 cm to 10 cm, preferably from 3 to 7 cm, more preferably from 4 to 6 cm. The pressing force is typically between 20 kN and 120 kN, preferably from 30 kN to 100 kN, more preferably from 40 kN to 80 kN, although lower pressures are possible and may be preferred in the present invention employing file particle size acid sources. Typically, the roll speed is between 1 rpm and 180 rpm, preferably from 2 rpm to 50 rpm and more preferably from 2 rpm to 35 rpm. Typically, the feed rate is between 1 rpm and 100 rpm, preferably from 5 rpm to 70 rpm, more preferably from 8 rpm to 50 rpm. Temperature at which compaction is carried out is not relevant, typically it varies from 0° C. to 40° C. It may be preferred that the granules are made under dry-air, having a humidity of below 30%.

EXAMPLES XII–XIII

Effervescent articles of the present invention were prepared using the compositions set forth in Table E. All of the components were thoroughly mixed in a conventional mixer and then loaded in spherical molds and compacted. The spherical tablets prepared weighed about 4.5 g and were about 18 mm in diameter. When placed in a beaker of water at a temperature of about 10° C., without agitation, the tablets were observed to dissolve within 3 to 5 minutes.

TABLE E

| | Example | |
|---|---|---|
| | XII | XIII |
| Perfume complexed with Zeolite | 20 | 8.4 |
| Polyethylene glycol (PEG 1500)* | 10 | 10 |
| Nymcel** | 10 | 10 |
| Sodium citrate | 30 | 51.6 |
| Citric acid | 19 | 19 |
| Sodium carbonate | 11 | 11 |

*Available from Union Carbide
**Sodium carboxymethylcellulose available from Metsa

EXAMPLES XIV–XIX

Effervescent articles of the present invention having the compositions shown in Table F are likewise mixed and then compacted in a spherical mold.

TABLE F

| | Example | | | | | |
|---|---|---|---|---|---|---|
| | XIV | XV | XVI | XVII | XVIII | XIX |
| Perfume | 13.6 | — | — | 9.0 | 7.3 | 9.1 |
| Perfume-Starch | — | 47.8 | — | — | — | — |
| Perfume-Zeolite | — | — | 51.0 | — | — | — |
| Sodium bicarbonate | 54.0 | 32.6 | 30.6 | — | — | — |

TABLE F-continued

| | Example | | | | | |
|---|---|---|---|---|---|---|
| | XIV | XV | XVI | XVII | XVIII | XIX |
| Sodium carbonate | — | — | — | 55.0 | 54.2 | 51.2 |
| Citric acid | 27.0 | 16.3 | 15.4 | 31.0 | 30.6 | 28.8 |
| Propylene glycol | 3.6 | 2.2 | 2.0 | — | — | — |
| PEG 1500 | — | — | — | 5.0 | 4.9 | 4.0 |
| Canola oil | 1.8 | 1.1 | 1.0 | — | — | — |
| Zeolite 13x* | — | — | — | — | 3.0 | 3.0 |
| Neodol 91-8 | — | — | — | — | — | 3.9 |

*Zeolite 13x without perfume

EXAMPLES XX and XXI

Examples XX and XXI concern effervescent articles containing cornstarch and witchazel. The articles of Example XX were prepared by placing the sodium bicarbonate in a common kitchen mixer. The citric acid was added and the mixture was stirred for approximately 5 minutes. The cornstarch was added and the mixture was stirred for an additional 5 minutes. The mixer was left on while the perfume was titrated into the mixture. Once the addition of perfume was complete, the mixture was stirred for an additional 10 minutes. Witchhazel was then added to the mixture with stirring until the composition began to stick together. Doses of the mixture were then placed in a mold and compacted to form spherical articles. The addition of the witchhazel should be monitored closely as addition of an excessive amount of witchhazel was observed to cause the product to effervesce.

| Component | Order of Addition | Weight % |
|---|---|---|
| Sodium bicarbonate | 1 | 55.0 |
| Citric acid | 2 | 24.0 |
| Cornstarch | 3 | 17.0 |
| Perfume | 4 | 4.0 |

The effervescent articles of Example XXI were prepared similarly to those of Example XX, with the exception that the perfume was replaced by the addition by titration of EMC, Neodol 91-8 and IME.

| Component | Order of Addition | Weight % |
|---|---|---|
| Sodium bicarbonate | 1 | 42.0 |
| Citric acid | 2 | 30 |
| Cornstarch | 3 | 20.25 |
| EMC* | 4 | 4.0 |
| Neodol 91-8 | 5 | 3.0 |
| IME (44.6%)** | 6 | 0.75 |

*Amide modified cellulosic polymer from Metsa Specialty Chemicals
**Imidazole-epichlorohydrin copolymer in water from BASF Other examples of effervescent articles of the present invention were made as spherical tablets about 18 mm in diameter and weighed about 3.5 g to about 4 g each. These tablets are used to pre-treat a brand new garment before it is washed for the first time to lock in colors and prevent dye bleeding. These pretreatment tablets dissolved in cold water (10° C.) in about 2 to about 3 min.

| | Wt. % | | |
|---|---|---|---|
| Component | XXII | XXIII | XXIV |
| Bis-DMAPA* | 16.4 | 16.4 | 16.4 |
| Cartafix CB** | 6.5 | 2.2 | 0.0 |
| PVP (40 M–360 M) | 4.9 | 4.9 | 0.0 |
| MgCl2 | 6.6 | 6.6 | 6.6 |
| PEG 1500 | 9.0 | 9.0 | 9.0 |
| HEDP*** | 0.12 | 0.12 | 0.12 |
| Sodium Carbonate | 25.2 | 27.2 | 30.4 |
| Citric Acid | 30.9 | 33.2 | 37.1 |
| Water | 0.38 | 0.38 | 0.38 |
| Total | 100.0 | 100.0 | 100.0 |

| Component | Material Activity | Wt % | Wt.(g) |
|---|---|---|---|
| Bis DMAPA* | 99 | 9.9 | 0.347 |
| Cartafix CB**, dried | 100 | 2.4 | 0.084 |
| PVP (40M–360M) | 100 | 4.9 | 0.170 |
| MgCl2 | 95 | 6.6 | 0.230 |
| HEDP | 59.5 | 0.2 | 0.008 |
| PEG 1500 | 100 | 9.0 | 0.315 |
| Citric Acid/Sodium Carbonate (55:45) | 100 | 67.0 | 2.346 |
| Total | | 100 | 3.500 |

*Bis-(Dimethylaminopropyl) amine
**Cationic polymer from Clariant
***Hydroxyethane diphosphonic acid, mono sodium salt (level expressed as acid)

Other examples of effervescent articles of the present invention were made as spherical tablets about 18 mm in diameter and weighed about 4 g each. These tablets are used to treat the rinse water in the laundry process, eliminate carry-over suds, and reduce the number of rinses needed.

| Component | Wt. % |
|---|---|
| Wacker Silicone SE39 | 2.90 |
| Citric Acid/Na Carbonate (55:45) | 50.0 |
| Sodium Citrate | 29.91 |
| HEDP | 4.61 |
| Chelant* | 4.61 |
| PEG 1500 | 7.97 |

*Diethylenetriaminepenta(methylenephosphonic acid) sodium salt

3. Foams

The articles of the present invention may optionally incorporate a foam component which can be utilized to serve a variety of functions. It has been found that when a specific foam component, comprising polymeric material and a fabric care active is used, effective delivery of the active and protection of the active, not only against air-moisture and chemical reactions but also against physical forces, is achieved. The foam component is found to be air-stable under normal humidity storage conditions, but water-unstable to thus deliver the actives, disintegrating or dissolving in water, to thus deliver the actives. Further, the foam may serve as a substrate for the active absorbing the active on its surface or adsorbing it into the cells of the foam. In addition, the foam component can act as a binder providing structural integrity to the article. Further, the foam may be used as an outer coating to protect the article and prevent premature disintegration or dusting of the article.

The foam component is preferably a stable flexible foam. It is critical that the foam component be stable when in contact with air and yet unstable upon contact with water. The foam component preferably releases the active ingredient or part thereof upon contact with water, with the foam component preferably partially or completely disintegrating, dispersing, denaturing and/or dissolving upon contact with water. The foam component may preferably be in the form of particles that can be incorporated in compositions, or in the form of a sheet, preferably such that it can form a foam sheet that can be used as protective coating for the composition.

a) Foam Component

The foam component of the invention comprises a polymeric material and an active ingredient. The foam component has a matrix formed from the polymeric material or part thereof, and optionally other materials. The matrix is preferably such that it forms an interconnected network of open and/or closed cells, in particular a network of solid struts or plates which form the edges and faces of open and/or closed cells. The spacing inside the cells can contain part of the active ingredient and/or a gas, such as air.

The polymer material and the active ingredient may be intimately, homogeneously mixed, in which case a so-called monophase foam component is obtained, which has uniform physical and chemical properties. However, it may be preferred that a multiphase foam component is obtained, whereby on a microstructure level one or more of the active ingredients is present in lower or higher amounts in one area of the component than in an other area of the component, and thus lower or higher than the average obtained by intimate mixing.

'Air-stable' or 'stable upon contact with air' when used herein, means that the bulk volume of the foam component substantially remains the same when exposed to air. This means in particular that the foam component herein retains preferably from 75% to 125% or even from 90% to 110% or even from 95% to 100% of its bulk volume when stored in an open beaker (9 cm diameter; without any protective barrier) in a incubator under controlled ambient conditions (humidity=RH 60%, temperature=25° C.) for 24 hours. Preferably the foam component retains from 75% to 125% or even from 90% to 110% or even from 95% to 100% of its bulk volume under the above storage conditions whereby the humidity is 80%.

The bulk volume change can be measured by any conventional method. Particularly useful is a digital image recorder system containing a digital camera coupled to a personal computer installed with a calibrated image analyser software. A 1 $cm^3$ specimen of the foam component is obtained and introduced in an open beaker having a diameter of 9 cm and stored for 24 hours at the above conditions. After 24 hours, the size in all three dimensions is measured with the image analysis recorder system. Each specimen measurement is repeated three times, and the average bulk volume change is calculated in %.

Preferably, the foam component is such that when in the form of particles of a mean particle size of 2000 microns or less, these foam component particles retain from 75% to 125% or even from 90% to 110% or even from 95% to 100% of their bulk volume. This can for example be measured by placing 20 grams of the foam component particles, or a weight comprising more than 500 particles, in a volumetric beaker having a diameter of 9 cm. The beaker is tapped lightly on its base until the foam component particles settle, rearranging themselves in a stable position with a horizontal top surface. The volume is measured. The open beaker with the foam component particles is then carefully placed in the incubator for 24 hours, set to the desired % RH and temperature. The bulk volume after the 24 hours is measured and the change of bulk volume is calculated in %.

The foam component of the invention is unstable when brought into contact with water. This occurs such that the active ingredients or part thereof, present in the foam component are delivered to the water. Preferably, the foam component or part thereof will denature, disintegrate, preferably disperse or dissolve in water. When the article is to be added to the rinse bath solution, it is preferred that the active ingredient be release to the solution rapidly and that the foam component is such that the polymeric material of the foam component disperses or dissolves rapidly, preferably at least 10% of the polymeric material, by weight, is dissolved or dispersed in 30 minutes after contacting the foam component with the water, more preferably at least 30% or even at least 50% or even at least 70% or even at least 90% (introduced in the water at a 1% by weight concentration). It may even be preferred that this happens within 20 minutes or even 10 minutes or even 5 minutes after contacting the foam component with the water. The dissolution or dispersion can be measured by the method described herein after for measuring the dissolution and dispersion of polymers.

Preferably the water-unstable foam component is such that the total volume of the foam component is reduced, by at least 10%, and preferably at least about 20%, 40%, 60% or even up to 90% or even about 100%, e.g. because it may be preferred that substantially the whole foam component is disintegrated, dispersed or dissolved into the water quickly. The dissolution rate of the foam component can be measured by use of any method known in the art, in particular herein with a method as follows (double immersion technique):

1 $cm^3$ of a foam component is obtained and introduced in a 100 ml micro volumetric measuring cylinder which is filled with 50 ml±0.1 ml of an organic inert solvent. Acetone is for example used when found to be neither denaturing and/or not interacting with the polymeric material in the foam component, for example when this is PVA. Other neutral organic medium can be used according to the nature of the foam under investigation; the inert solvent is such that the foam component is substantially not dissolved, dispersed, disintegrated or denatured by the solvent. The cylinder is air sealed and left to rest for 1 minute so that the solvent penetrates the whole foam specimen. The change in volume is measured and taken as the original volume $V_i$ of the foam specimen. The foam specimen is then removed from the solvent and left to dry in air so that the solvent evaporates.

The foam specimen is then placed in a 250 ml beaker containing 100 ml of demineralised water, maintained at 25° C., under stirring at 200 rpm with the help of a magnetic stirrer, for 5 minutes. The remaining of the foam component specimen is filtered off with a 60 mm mesh copper filter and placed in a oven at a temperature and for a period such that residual water is removed. The dried remaining foam component is re-introduced in the measuring cylinder which volume of acetone had been re-adjusted to 50 ml.

The increase in total volume is monitored and taken as the final volume of the foam specimen $V_f$. The decrease in total volume $\Delta V$ of the foam specimen is then:

$$\% \Delta V = \frac{Vf}{Vi} * 100$$

The foam component has preferably a relative density $\phi^*_{foam}$ of from 0.01 to 0.95, more preferably from 0.05 to 0.9 or even from 0.1 to 0.8 or even form 0.3 to 0.7. The relative density is the ratio of the density of the foam component to the sum of the partial densities of all the bulk materials used to form the foam component, as described below:

$$\rho^*_{foam} = \frac{\rho_{foam}}{\rho_{bulk}} = \frac{\rho_{foam}}{\sum_{i=1}^{i=n} \chi_i \rho_i}$$

where ρ is the density, and $\chi_i$ is the volume fraction of the materials i in the foam components.

It is preferred that the foam component is a flexible foam component. In particular, this means that the flexible foam component reversibly deforms, absorbing the energy of impacts or of forces so that the foam component remains substantially its original bulk volume after the physical force seizes to be applied on the component.

In particular this means that when a foam component sample having a cross section of a specific length, for example 1 cm, is compressed with a static force applied along the axis of that cross section, the static force being variable but at least equivalent to twice atmospheric pressure, the change of this length after removal of the force is at least 90% to 110% of the original length. This can for example be measured by use of Perkin-Elmer DMA 7e equipment.

Similarly, the foam component is preferably flexible to such an extend that when a foam component sample having a cross section of a specific length, for example 1 cm, is stretched with a static force applied along the axis of that cross section, the static force being variable, but at least equivalent to twice atmospheric pressure, the change of this length after removal of the force is at least 90% to 110% of the original length. This can for example be measured by use of Perkin-Elmer DMA 7e equipment.

The flexibility of a foam component can also be reflected by the Young's or elastic modulus, which can be calculated from strain or stress mechanical tests as known in the art, for example by using Perkin-Elmer DMA 7e equipment following the manufacturer's experimental procedure. For example a foam component of 1 $cm^3$ can be used in the testing with this equipment.

In particular, when using this equipment, the static forces applied along the axis of a cross section of a 1 $cm^3$ foam component are gradually increased until the deformation of the component, in the direction of the cross section, is 70%. Then, the force is removed and the final deformation of the foam component in the direction of the cross section is measured. Preferably, this length of the cross section after this experiment is preferably from 90% to 110% of the original length of the cross section, preferably from 95% to 105% or even from 98% to 100%.

The foam component herein preferably has an elastic modulus or Young's modulus of less than 10 $GN.m^{-2}$, even more preferentially less than 1 $GN.m^{-2}$, as measured with the Perkin-Elmer DMA 7e equipment. Preferably the polymeric component has a relative yield strain greater than 2%, and preferably greater than 15% or even greater than 50%, as measured with the Perkin-Elmer DMA 7e equipment. (The yield strain is in this measurement the limit deformation of a foam component at which the component deforms irreversible).

The elastic modulus or Young modulus is related to the relative density, namely $$\frac{E^*}{E_s} \approx \left(\frac{\rho^*}{\rho_s}\right)^2,$$

where ρ* and $\rho_s$ are as described above and E* is the Young's modulus of the foam component, and $E_s$ that of the polymeric material. This means that even stiff polymeric materials, with a high $E_s$ can be made into relatively flexible foams, by modifying the density thereof, in particular by introducing more gas in during the foam making process or by using additives, such as plasticisers at adjusted levels.

The foam component comprises preferably at least 1% by weight of the active ingredients, more preferably from 5% to 95%, more preferably from 10% to 80% or even from 15% to 70%. The foam component comprises preferably at least 10% by weight of the polymeric material, more preferably from 15% or even 20% or even 25% to 99%, more preferably from 30% to 90% or even from 35% to 90% or even to 80% by weight.

b) Matrix

The foam component comprises a matrix, formed from or partially formed from at least part of the polymeric material. This means that the matrix may be formed completely by the polymeric material, or the matrix may be formed partially by the polymeric material and partially by the active ingredient or part thereof, or by other additional ingredients.

The matrix is preferably such that it forms an interconnected network of open and/or closed cells, in particular a network of solid struts or plates which form the edges and faces of open and/or closed cells. Then, the polymeric material or part thereof, forms at least part of the struts or plates, while the active ingredient, and optionally other materials, may form part of the struts or plates.

c) Polymeric Material

Any polymeric material that may be formed into an air-stable, water-unstable foam, can be used in the foam component and can be used to form the matrix or a part thereof. It is preferred that the polymeric material comprise a water-dispersible or water-soluble polymer, and more preferably that the polymeric material be soluble in water that is about or less than about 10° C.

Preferred water-dispersable polymers herein have a dispersability of at least 50%, preferably at least 75% or even at least 95%, as measured by the method set out hereinafter using a glass-filter with a maximum pore size of 50 microns; more preferably the polymer herein is a water-soluble polymer which has a solubility of at least 50%, preferably at least 75% or even at least 95%, as measured by the method set out hereinafter using a glass-filter with a maximum pore size of 20 microns, namely:

Gravimetric method for determining water-solubility or water-dispersability of polymers:

50 grams±0.1 gram of polymer is added in a 400 ml beaker, whereof the weight has been determined, and 245 ml±1 ml of distilled water is added. This is stirred vigorously on magnetic stirrer set at 600 rpm, for 30 minutes. Then, the water-polymer mixture is filtered through a folded qualitative sintered-glass filter with the pore sizes as defined above (max. 20 or 50 microns). The water is dried off from the collected filtrate by any conventional method, and the weight of the remaining polymer is determined (which is the dissolved or dispersed fraction). Then, the % solubility or dispersability can be calculated.

Preferred are polymers selected from cationic polymers, such as quaternary polyamines, polyvinyl alcohols, polyvinyl pyrrolidone, polyalkylene oxides, cellulose, polysaccharides, polycarboxylic acids and salts, polyaminoacids or peptides, polyamides, polyacrylamide, and mixture, derivatives or copolymers thereof. More preferably, the polymer is selected from polyvinyl alcohols, cellulose ethers and derivatives thereof, copolymers of maleic/acrylic acids, polysaccharides including starch and gelatin, natural gums such as xanthum and carragum and mixtures thereof.

Copolymers block polymers and graft polymers of the above can also be used. Mixtures of polymers can also be used. This may in particular be beneficial to control the mechanical and/or dissolution properties of the foam component, depending on the application thereof and the required needs.

The polymer can have any average molecular weight, preferably from about 1000 to 1,000,000, or even form 4000 to 250,000 or even form 10,000 to 200,000 or even form 20,000 to 75,000.

Preferred can be that the polymer used in the foam component herein has a secondary function in the composition wherein the foam component is to be incorporated. Thus for example is cleaning products, it is useful when the polymer is a builder polymer, soil release polymer, dye transfer inhibiting polymer, process aid, suds suppresser, dispersant, flocculant etc.

Preferred polymers in cleaning compositions may be homopolymers or copolymers containing monomeric units selected from alkylene oxide, particularly ethylene oxide, acrylamide, acrylic acid, vinyl alcohol, vinyl pyrrolidone, and ethylene imine, organic polymeric clay flocculating agents as described in European Patents No.s EP-A-299,575 and EP-A-313,146, more preferred polyvinylpyrrolidones, polyacrylates and water-soluble acrylate copolymers, methylcellulose, carboxymethylcellulose sodium, dextrin, ethylcellulose, gelatin, guar gum, hydroxyethyl cellulose, hydroxypropyl methylcellulose, maltodextrin, polymethacrylates, cationic polymers including ethoxylated hexamethylene diamine quaternary compounds, bishexamethylene triamines, or others such as pentaamines, ethoxylated polyethylene amines, polyamino compounds such as those disclosed in EP-A-305282, EP-A-305283 and EP-A-351629, terpolymers containing monomer, non-cotton soil release polymer as described in to U.S. Pat. No. 4,968,451, and U.S. Pat. No. 5,415,807, dispersant/anti-redeposition agent, for use herein, can be the ethoxylated cationic monoamines and diamines, as described in EP-B-011965 and U.S. Pat. No. 4,659,802 and U.S. Pat. No. 4,664,848.

d) Process for Making the Foam Component

The foam component may be made by any process known in the art for making foam components, preferably involving at least a step of mixing the polymeric material with the active ingredient.

Preferably the process comprises the steps of a) obtaining a polymeric material;
b) chemically or physically introducing gas in said polymeric material;
c) prior to step b) and/or simultaneously with step b) and/or subsequently to step b), addition of the active ingredient to the polymer material;
d) optionally addition a of further ingredients, preferably including a plasticiser and/or with a liquid, preferably water, in one or more of steps a), b) or c); and
e) optionally one or more of steps b), c) or d) followed by removal of the liquid or part thereof.

The active ingredient can be mixed with the polymeric material prior to step b) or preferably the active ingredient is added subsequently to step b). This process herein is preferably such that in step a) a plasticiser is present in the mixture and preferably also water.

The foam component herein can also be obtained by a process comprising the steps of:

a) formation of a mixture of the polymeric material, the active ingredient and a liquid, preferably water;
b) evaporation of the liquid or part thereof to form spacings which are the areas inside cells of the matrix of the foam component.

Step b) is preferably conducted by submitting the mixture of a) to pressure, preferably under mixing and/or increasing the temperature, and subsequently removing the pressure or part thereof, thereby causing the liquid to evaporate. For example, an extrusion process can be used. Hereby it is preferred that the mixture of the polymeric material, active ingredient and liquid, preferably water, is introduced in an extruder, wherein the mixture is further mixed and heated, due to the mixing or due to applying heat, preferably such that the mixture or polymeric material therein forms a melt, and then dropping the pressure at the exit point where the extruded mixture (which can be formed into the desired form, for example granules) exits the extruder, whereby the liquid or part thereof evaporates, or preferably the water evaporates as steam from the extruded mixture. This procedure results in formation of cells with spacings, as described above, which then may contain a gas, preferably air, and optionally the active ingredient. These spacings form the internal area of the cells of the matrix of the foam component of the invention.

Step b) in the process may also be conducted by heating the mixture to cause the liquid or part thereof to evaporate, resulting in the formation of spacings, as above. This can preferably done by feeding the mixture into a spray drying tower, preferably such that the mixture is fed through spray nozzles which form droplets of the mixture, and spray drying the droplets at conventional, resulting in granules of the foam component.

The physical foaming and/or chemical foaming can be done by any known method, preferred are

- physical foaming by gas injection (dry or aqueous route), high shear stirring (dry or aqueous route), gas dissolution and relaxation including critical gas diffusion (dry or aqueous route);
- chemical foaming by in-situ gas formation (via chemical reaction of one or more ingredients, including formation of $CO_2$ by an effervescence system),
- steam blowing, UV light radiation curing.

Also preferred, as set out above, is a process whereby the mixture of polymeric material, actives and liquid is treated such that the liquid or part thereof evaporates, leaving spacings in the mixture, which then preferably are filled by a gas, resulting in the foam component of the invention.

These foaming steps such as step b or step c in the first process above, but also preferably the last steps of the second process, are preferably followed by a drying step or additional drying step to remove excess liquid, such as water, which may be present. In particular, the drying step is done after the polymer material is foamed and the active ingredient is added, thus as final step in the process. The drying step is done final foam component is of about the same volume after the drying step as before the drying step. Thereto, the drying step is preferably done by freeze-drying, whereby the solvent, e.g. water, is removed under vacuum and reduced temperatures. Also useful can be slow oven drying at modestly increased temperatures, such as 40–80° C., or even 40–60° C. for example 2–40 hours, preferably 10–30 hours.

e) Form of Foam

The foam component can be made into any form, by any conventional method. Preferred may be that the foam component is in the form of a particles, including pastilles and beads, tablets, or in the form of a sheet. The particles can be made by any granulation method, for example by grinding larger shapes of the foam component, such as the sheets described herein, spray-drying, extrusion, as also described above.

Preferred particles of the foam component have a mean particle size of from 10 to 5000 microns, more preferably from 50 to 4000 microns or even to 2000 microns, even more preferably from 100 to 1500 microns or even form 200 to 1000 microns.

The foam component may also be in the form of a sheet, which can be obtained by any method, preferably by forming the sheet in a mold, as described above. When the foam component is in the form of a sheet, the sheet can have any dimension and can be subsequently reduced in size as required. It may be preferred that the sheet has a mean thickness of from of from 0.01 to 400 microns, more preferably from 0.05 to 200 microns, or even more preferably from 0.1 to 100 microns, or even 0.1 to 50 microns.

It may be preferred that the foam component is in such a form, preferably a sheet form, that it can be used to encapsulate the additive composition or that the foam components form a pouch structure around the additive composition. Such an encapsulate or pouch can for example conveniently be made by heat sealing a sheet of the foam component around the product.

It may be preferred that the foam component optionally comprise a plasticiser. Preferred plasticisers are selected from glycerol, ethylene glycol, diethyleneglycol, propylene glycol, sorbitol and mixtures thereof. Preferred levels are from about 0.05% to about 15% or even from about 0.2% to about 10% or even from about 0.3 to about 5% by weight of the foam component.

A coloring agent such as iron oxides and hydroxydes, azo-dyes, natural dyes, are also preferred for use as the identification means described herein or merely for ornamentation purposes. The coloring agent will preferably be present at levels of 0.001% and 10% or even 0.01 to 5% or even 0.05 to 1% by weight of the component. Highly preferred additional ingredients include urea and/or inorganic salts.

Water may be present in the foam component, but preferably only in small amount, any excess being removed by drying such as by freeze drying. Generally, water is present at a level of about 0% to about 10%, more preferably from about 0.2% to about 5% or even about 0.2% to about 3% or even from about 0.5% to about 2% by weight of the foam component.

As described above, it is also preferred that a dispersion, dissolution or disintegration agent be present in the foam component. In addition to the description concerning such agents provided above, examples of such agents are described in EP851025-A and EP466484-A. It should be understood that the polymeric material of the foam component may comprise polymers which also act as dispersion, dissolution or disintegration agents.

It is preferred that the foam component optionally contain an acidic material and/or an alkaline material and/or buffering agent, which may be the polymeric material and/or the active ingredient, or an additional ingredient. For example, it may be preferred that the polymeric material comprises an acidic polymer, for example a polycarboxylic acid polymer, or that the foam component comprises as active ingredient an effervescence source comprising an acidic compound and a carbonate source. The presence of an acidic material improves the dissolution and/or dispersion of the foam component of the invention upon contact with water, and can also reduce or prevent interactions, leading to for example precipitation, of the polymeric material in the foam component with cationic species such as fabric softeners are present in the laundry solution. The preferred acids include citric acid, acetic acid, acetic acid glacial, fumaric acid, hydrochloric acid, malic acid, maleic acid, tartaric acid, nitric acid, phosphoric acid, sulfuric acid, pelargonic acid, lauric acid. When a buffering agent is used, boric acid, sodium acetate, sodium citrate, acetic acid, potassium phosphates and the like are preferred.

A most preferred additional ingredient, when not otherwise included, is an effervescent system or sources such as are described herein.

EXAMPLES XXVII–XXXI

Preparation of Foam Compositions

Foam containing articles of the present invention were prepared by weighing the polyvinyl alcohol, glycerine, and citric acid into a kitchen style mixing bowl, and mixing the components together by hand until a crumbly agglomerate was achieved. The dye was dissolved in water and the dye solution and perfume oil were added to the mixing bowl. The composition was mixed with a convention kitchen mixer set on its low speed setting to yield a viscous homogenous solution. The mixer speed was then increased to its maximum forming a stiff foam.

The foam was then transferred to molds for drying. Drying was carried out by oven drying at 55° C. overnight or by freeze-drying under vacuum overnight. Although the amount of water added during the process varied between about 160 and about 230 grams, the amount of water in the final product remained relatively constant following the drying step. It is to be noted that the more water used during the process, the lower the density and the more flexible the foam produced. Further, it was also observed that the lower density foams exhibited faster dissolution rates in solution.

| | XXVII | XXVIII | XXIX | XXX | XXXI |
|---|---|---|---|---|---|
| Polyvinyl alcohol* | 54.11 | 54.0 | 54.0 | 54.0 | 54.0 |
| Glycerine | 16.25 | 16.0 | 17.0 | 15.0 | 15.0 |
| Citric acid | 10.89 | 11.0 | 5.0 | 10 | 10 |
| Perfume | 18.75 | 19.0 | 20.0 | 14.0 | 24.0 |
| Perfume in Zeolite** | — | — | — | 10.0 | — |
| Dye*** | 0.0028 | 0.003 | 0.003 | 0.003 | 0.003 |

*PVA had a molecular weight between about 30,000 and 70,000
**Perfume was loaded into Zeolite 13X at about 13%.
***Pigment Green No 7

4. Waxy Beads

A preferred article of the present invention may also be in the form of waxy bead that comprises a fabric care active or mixture of actives and a polymer that will serve as carrier for the active before the article is dispensed in a laundry solution. While any water soluble polymer capable of being formed into a bead or sphere, and capable of dissolving in cold water is useful, especially preferred are polyethylene glycols.

EXAMPLE XXXII

Preparation of Perfume Waxy Bead

A waxy bead type fabric care article was prepared containing 50% by weight polyethylene glycol (PEG 8000), 25% Neodol 91-8 as an emulsifier, and 25% perfume active. The PEG 8000 was weighed into a beaker and melted in a microwave oven. Equal parts of Neodol and perfume were weighed into a separate beaker. When the PEG was melted, the Neodol/perfume mixture, in an amount equal to the weight of the PEG, was added to the beaker containing the PEG and mixed with a spatula. The product can be made into spheres, tablets, or any other moldable shape by pouring the product into an appropriate mold and allowing it to solidify. If the product starts to solidify due to cooling prematurely, the mixture should be gently re-heating in the microwave. If a lower melting point for the product is desired, lower molecular weight polyethylene glycols should be used.

5. Liquids and Gels

The fabric care actives of the present invention may also be delivered or dispensed in the laundry solution in the form of a viscous liquid or gel. Specifically, a viscous liquid containing a perfume active may be prepared by forming a mixture of the perfume active and preferably an emulsifier and solvent that will aid the incorporation of the perfume and produce a uniform, relatively clear product.

Optionally, dyes and other color agents may be included in the composition. Table G provides a specific example concerning the preparation of a viscous liquid fabric care composition to be dispensed in a laundry solution to deliver a selected fragrance to that solution. The components were added to a beaker with spatula mixing after each addition until a homogenous composition was attained.

TABLE G

| Component | Order of Addition | Weight % |
|---|---|---|
| Perfume | 1 | 50.0 |
| Neodol 91-8 | 2 | 25.0 |
| 2-Ethyl-1,3-hexanediol | 3 | 23.9 |
| Blue Dye (1% active) | 4 | 1.0 |
| Kathon CG (1.54% active) | 5 | 0.065 |

EXAMPLE XXXIII

Viscous Gel

A viscous gel may similarly be prepared as the viscous liquid described above but with the addition of a gum base or similar gelling material. Specifically, a 3% Xanthan gum base was prepared by adding the Xanthan Gum base (obtained from Keltrol RD) to a beaker containing 0.43% of dilute (1.54%) Kathon CG and 96.57% of hot deionized water with vigorous stirring until the gum was dissolved. The Xanthan gum solution was then allowed to cool and weighed into a beaker. Deionized water was added while stirring with a large spatula until the solution became homogeneous. Perfume was then added with stirring as the product tends to separate. Neodol 91-8 was added to the beaker with stirring and the product thickened and became cloudy. 2-Ethyl-1,3-hexanediol was then added and the product was stirred for approximately 3 minutes. The product continued to thicken but became clear. A dye solution was added and the product was stirred for an additional 3 minutes. The product was a viscous blue gel. The weight percentage of each of the components is provided in Table H.

TABLE H

| Component | Order of Addition | Weight % |
|---|---|---|
| 3% Xanthan Gum Base | 1 | 15.0 |
| Deionized water | 2 | 27.0 |
| Perfume | 3 | 25.0 |
| Neodol 91-8 | 4 | 25.0 |
| 2-Ethyl-1,3-hexanediol | 5 | 7.0 |
| Blue Dye (1% active) | 6 | 1.0 |

Preferably, liquids and gels are dispensed in unitized dosing fashion by a squeeze-to-fill bottle, pump, trigger sprayer, unitized flexible package, or other device discussed below.

D. Dispensing Means

1. Pump and Spray Dispensers

The present invention also relates to the incorporation of the fabric care compositions of the present invention in a pump or spray dispenser or squeeze-to-fill bottle to create an article of manufacture that will facilitate the dispensing of a unitized dose of such compositions to a laundry solution. Nonlimiting examples of squeeze bottle are disclosed in, e.g., U.S. Pat. No. 4,564,129, issued Jan. 14, 1986 to Urban et al, and U.S. Pat. No. 4,607,762, issued Aug. 26, 1986 to Zulauf et al.

Conventional well known pumps and spray dispensers may be used to dispense the compositions. Pump bottle dispensers include fixed-volume and adjustable volume dispensers. Nonlimiting examples of pump bottle dispensers are disclosed in Cole-Parmer 2001/02 Catalog, pp. 294–300, Vernon Hills, Ill.

Spray dispensers typically comprise manually activated and non-manual powered (operated) spray means and a container containing the fabric care composition. Typical disclosure of such spray dispenser can be found in WO 96/04940 page 19 line 21 to page 22 line 27.

2. Self-contained Dispensing Devices for Placement in a Washing Machine Tub

Rinse water additive dispensers are well known in the art. Examples include U.S. Pat. No. 5,768,918 to McKibben; U.S. Pat. No. 5,267,671 to Baginski et al.; U.S. Pat. No. 3,108,722 to Torongo, Jr: et al.; U.S. Pat. No. 3,888,391 to Merz, and U.S. Pat. No. 4,835,804 to Arnau-Munoz et al. Centrifugal force applied to a weight inside the dispenser during a spin cycle of an automatic clothes washer causes a dispenser valve to become unseated so that composition from the dispenser may spill out of the dispenser and mix with rinse water that is added to the wash tub after the spin cycle. The fabric care compositions and articles of the present invention that are designed for dispensing in a rinse bath may be inserted into such a dispenser to prevent release of the composition during the wash cycle. Specifically, the dispenser is placed in the wash tub before the wash cycle begins and should remain closed during the agitation of the wash cycle. The dispenser will then open during the spin cycle at the conclusion of the wash cycle in order to deliver the rinse water fabric care composition when it will be most effective.

It is preferred that the solid articles of the present invention, especially tablets, spheres and capsules, have a diameter or width from about 1 mm to about 26 mm, more preferably from about 5 mm to about 20 mm and even more preferably from about 8 mm to about 18 mm, to facilitate placing them in a self contained dispensing device.

The dispenser is typically a cylinder or a ball shaped container that has a large circular opening at one end. The dispenser is normally only partially filled with a composition in dose form of one or more articles, such that the dispenser primarily contains air and space for a valve to be actuated. A dispenser valve is typically a resilient rubber device, such as a pair of interconnected rubber disks acting as a grommet at the edge of the circular opening. A rigid arm extending from the pair of rubber disks, parallel to the axis of the opening, has a counterweight connected to the arm. In a closed valve position the rubber disks seal the opening from both sides such that wash water cannot enter and additive cannot leave. Gravity acting upon the counterweight is insufficient to cause the disks to be deformed and pop out of the opening to open the valve. However, centrifugal force generated by the spin cycle of the washer, is sufficient to pull the arm at an angle to the axis of the opening, thereby distorting the rubber disks and causing them to pop out of engagement with the edges of the opening. The valve remains open thereafter so that as the washer fills with rinse water, the additive from the dispenser may spill out, and/or the rinse water may fill the dispenser and mix with the additive.

3. Dispensing Devices Incorporated into Washing Machine

Further, it has become common for manufacturers of washing machines to incorporate devices in their machines for the dispensing of rinse added fabric compositions. U.S. Pat. No. 5,500,967 to Wilson et al.; U.S. Pat. No. 5,033,277 to Khan et al.; and U.S. Pat. No. 4,656,844 to Mulder et al. are examples of such devices that are incorporated into the agitator or the top of the agitator of the washing machine, and will dispense a fabric care composition or article during the spin cycle when the tub reaches a predetermined rpm.

For machine dispensers that are attached to the top of the agitator, an article of this invention preferably has a relatively small size, e.g. less than about 10 mm in diameter or width. It is preferred that the diameter or width of the solid article, particularly a tablet, sphere or capsule, be from about 1 mm to about 9 mm and more preferably from about 5 mm to about 8 mm. This relatively small size is required for the article to fit through the opening of a machine dispenser which was most commonly designed for a liquid additive composition.

Alternatively, dispensing devices that are incorporated into the washing machine may comprise one or more dispensing drawers that actuate at predetermined or programmed times during the laundering operation. Such devices are more commonly found in washing machines manufactured for distribution in Europe, but are also known as high efficiency or "horizontal axis" washing machines in North America.

It is to be anticipated that as washing machine designs change, the size of the openings for the dispensing devices in automated washing machines will be increased to accommodate larger sized articles.

4. Substrates

The fabric care compositions of the present invention may be delivered to a laundry solution on substrates such as a porous flexible sheet, a sponge or some other material that will absorb or adsorb an effective amount of a fabric care composition and release that fabric care composition in the aqueous environment of the wash or rinse bath solution. In the alternative, the use of water soluble substrates made of soluble foams or films may likewise be used to deliver the fabric care compositions of the present invention.

Sponge materials and methods of loading such materials with fabric care compositions are known in the art as described in U.S. Pat. Nos. 4,824,582 and 6,033,729. U.S. Pat. No. 4,824,582, discloses dryer-added fabric conditioning articles such as sponges that utilize alkyl amine-anionic surfactant ion-pair complexes as fabric conditioning agents. It is indicated in U.S. Pat. No. 4,824,582 that the compositions thereof may also contain polymeric soil release agents and fabric softeners. Although the sponge in this patent was specifically, designed to deliver a dryer-added fabric conditioning agent, it is expected to be equally effective at delivering such actives in the solution environment of the wash and rinse bath solutions. One method of making this multi-use article includes filling a hollow sponge with about 20 grams of the fabric conditioning composition.

Similarly, U.S. Pat. No. 6,033,729 discloses a substantially anhydrous, three-dimensional water-activatable, expandable sponge article that is in a permanently compressed state in the absence of water. The fabric conditioning article consists essentially of a substantially anhydrous hydrophilic water-activatable, expandable sponge substance having a discrete geometric shape, a thickness along the z axis in the range of from about 0.05 inches up to about 2.0 inches, an average dimension along the x axis of from about 1 inch up to about 6 inches, an average dimension along the y axis of from about 1 inch up to about 6 inches. The sponge has a surface area from about 3 square inches up to about 150 square inches and sufficient porosity to retain from about 0.25 up to about 2.0 grams of a hydrophobic perfume oil or other fabric care composition. The perfume oil is contained within the interstices of said sponge substance and absorbed therein is intimately admixed with from about 0.25 up to about 2.0 grams of at least one substantially anhydrous fragrance substantivity-fabric relaxing agent selected from the group consisting of dialkyl dimethyl quaternary ammonium salts, imidazolinium quaternary salts, diamidoamine quaternary salts and monomethyl trialkyl quaternary ammonium salts.

Dryer-added fabric care agents are commonly deposited on a dryer sheet that is placed with a load of wet clothes in a dryer for transferring the fabric care agents to the clothes during the dryer operation. Such sheets, their manufacture as well as processes for depositing the fabric care agents thereon are particularly well known in the art. The use of such sheets in delivering a unitized dose of the fabric care compositions of the present invention is a preferred method of delivering the fabric care composition to a laundry wash or rinse bath solution.

5. Passive Dispensers

Passive dosing means is an apparatus that can provide a desired amount of composition without deforming the container. Non-limiting example of passive dosing means include dosing caps and tilting dispensers. An example of a tilting dispenser is given in Aldrich Handbook of Fine Chemicals and Laboratory Equipment 2000–2001, p. T233, Milwaukee, Wis. Containers for flowable laundry compositions typically include closure such as a cap that will enable the consumer to measure and dispense a desired amount of the composition for a given sized load of fabrics.

E. Article Packaging

Optionally, the articles of the present invention may include a package for containing one or more unitized doses of the fabric care composition. Packaging for an article is particularly preferred where the articles may be distributed individually, such as in a "sample" dose that is distributed with the sale of a fabric or an article of clothing, with the sale of a detergent or fabric softener, with a direct advertising mailer or similar promotional efforts. It is also anticipated that the fabric care compositions and articles of the present invention will be made available for sale in single dose packaging. In addition, it is preferred that the article package may contain multiple doses or articles having the same or different types of fabric care actives.

It is preferred that the article packaging act as a moisture barrier to protect the enclosed article from moisture such as through prolonged exposure to high humidity. The packaging materials should be relatively inexpensive to manufacture and process and should be inert with respect to the laundry article and its outer surface. Thus, the article packaging may be a simple thermoplastic film or over-wrap that is heat sealed to enclose the article. Alternatively, the packaging material may be a rigid plastic or a similar inexpensive rigid material that will protect the article from physical damage during distribution. Additionally, an individual article may be over-wrapped and placed inside an outer container to provide additional protection to the article.

Preferably, the article packaging will have child-resistant means so as to prevent a child from inadvertently accessing the article and ingesting or choking on it. Conventional child-resistant closure devices may be used on the containers or packaging of the articles of the present invention. Many of such devices include a cylindrical container such as a medicine bottle having a top with specific structures to secure the top to the bottle until a specific operation is carried out to disengage the top from the bottle. By way of example, U.S. Pat. No. 4,948,002 discloses bottle having child-resistant closure means in the form of a collar that is secured to the uppermost portion of the bottle and a closure which is secured to the finish portion of the bottle. The collar preferably includes a pair of spring-like push tabs containing vertical extensions which engage interlocking teeth on the innermost surface of the closure skirt when the closure is fully assembled onto the bottle. To remove the closure, the opposed push tabs must be manually depressed prior to applying unscrewing torque to the closure to disengage the push tab extensions from the interlocking teeth on the closure. The spring-like push tabs may be a part of a collar attached to the bottle, or an integral part of the bottle without a collar. Similarly, U.S. Pat. No. 6,036,036 discloses a package comprising a container and a closure on the upper end of the container, the package having a interlocking tooth and push tab that cooperate to prevent the closure from being moved without depressing and moving the push tab.

Other types of child-resistant packaging and dispensing devices may also be used. For instance, where the fabric composition is in a liquid or gel form, the composition may be dispensed from a flexible container or package or a container having a spout. A child-resistant closure for such a package is described in U.S. Pat. No. 5,078,288 wherein a closure is retained in the neck of the spout by internal threads and several ratchets that prevent the closure from being unscrewed from the neck opening without flexing the neck to prevent engagement between the closure and the internal ratchets.

Flowable forms of the fabric compositions of the present invention may also be dispensed using a breakable sachet that has been scored so as to break along the score when bent or folded along that score. Such a dispensing device is disclosed in U.S. Pat. No. 6,041,930 and provides child-resistant means to the packaging for the articles and compositions of the present invention.

Blister packages may also be used in dispensing the articles of the present invention. Typical blister packages have a thermoformed blister layer which is generally planar except in the areas where blisters are formed and a rupturable layer which is utilized to seal the fabric care composition within the blister. To remove a fabric care article from the package, a force is applied to the blister to force the article through the rupturable layer. In order to make such a package child-resistant, typically, a non-rupturable layer is laminated to the blister layer such that it will prevent the article from being forced through the rupturable layer until the non-rupturable layer is rendered ineffective. A common approach for rendering the nonrupturable layer ineffective is to enable the nonrupturable layer to be peeled from the blister package. Peeling of the nonrupturable layer is often enabled by extending the nonrupturable layer past the blister layer such that a grasping tab is provided. Alternatively, peeling is often enabled by including a line of weakness in the blister layer such that upon breaking the blister layer along the line of weakness a grasping tab is provided. A more recent improvement to render a blister package child-resistant is described in U.S. Pat. No. 5,613,609 wherein the blister is subdivided into storage and discharge chambers by restraint means. A predetermined amount of force is required to break the restraint means and thereby allow the contents to move from the storage chamber to the discharge chamber where the contents can subsequently be forced through rupturable layer.

Prior to the present invention, fabric care actives were delivered to a laundry solution in the form of bulk detergent or fabric conditioning compositions that contained multiple actives and were designed for dispensing in a wash or a rinse bath solution. Such formulated compositions did not allow the end user the flexibility to select and choose the individual benefits desired from the laundering operation. For instance, such compositions are typically formulated with a given fragrance or perfume, and thus, the consumer has no opportunity to choose the fragrance that will be imparted to their fabrics. A primary advantage of the present invention is the ability to select the specific actives that will be dispensed in the laundry solution, whether that active is a desired fragrance, a color maintenance agent, a wrinkle control active or some other fabric care active. Most fabric care benefits are dependent, in whole or in part, upon the personal preferences of the consumer. Existing pre-formulated bulk laundry compositions do not allow the consumer the opportunity to customize their laundry solutions to provide desired benefits.

Despite the great advantages provided by the unitized dosing of the fabric care compositions and articles of the present invention, consumers are not familiar with such dosing, and it is likely that they will not fully recognize the potential benefits that are available through the present invention. Accordingly, many consumers may not avail themselves of those benefits.

It is therefore preferred that the article packaging will optionally include a set of associated instructions concerning the use of the articles in preparing a customized laundry solution to suit the individual preferences of the consumer. Preferably, the associated instructions will provide a consumer with sufficient information to select and combine fabric care actives by dispensing articles containing those actives in a laundry solution to produce a solution that will deliver one or more fabric care benefits as desired by the consumer or needed for proper care of their fabrics.

Similarly, instructions associated with the packaging for fabric care articles should assist the consumer in selecting articles for preparing a laundry solution for specific fabrics. It is quite typical for consumers to sort clothing and to launder similar fabrics together. As such, it is preferred that the associated instructions also provide information that is specific to groupings of certain fabrics, such as linens, white fabrics, colored fabrics and delicates and the proper maintenance of such fabrics.

The associated instructions will preferably comprise printed materials such as package labels and package inserts that are provided with the product, pre-recorded audio or visual instructions for broadcast via radio and television, for download from a global computer network and for playback via electronic means. As used herein, "pre-recorded" refers to instructions recorded on any electronic or computer readable medium. Further, the use of live demonstrations in retail establishments or in-home settings are likewise effective in providing instruction to the consumer concerning the use of the articles of the present invention. Further, it is also preferred that the associated instructions indicate where the consumer may access more detailed information concerning the fabric care articles of the present invention and their use. Specifically, it is anticipated that the associated instructions will provide an address or site designation where detailed instructions may be downloaded from a global computer network such as the World Wide Web.

III. Laundry Kit for Customizing a Laundry Solution

The present invention also provides an article of manufacture comprising a laundry kit that may be used to prepare a customized laundry solution which will impart one or more desired fabric care benefits to fabrics laundered in that solution. Preferably, the laundry kit of the present invention will include a plurality of unitized doses of a fabric care composition each having a fabric care active or mixture of actives that is between about 1% and about 99% by weight of the composition and having less than about 5%, more preferably less than about 3%, and even more preferably less than about 1% detergent surfactant and less than about 5%, more preferably less than about 3%, and even more preferably less than about 1% fabric softener active. Further, the laundry kit of the present invention may optionally contain a detergent and/or fabric softener, instructions concerning the fabric care actives and their use in preparing a customized laundry solution, and packaging for the kit.

The individual articles and unitized doses contained in a laundry kit of the present invention may take the variety of forms previously described herein, namely, solids, waxy solids, pastes, slurries, liquids, dispersions, gels, solids, foams, sprays and aerosols. Further, each of the articles will comprise a fabric care composition having a variety of actives that may be delivered to the laundry solution to provide a preferred fabric care benefit. As previously described, the actives may include perfumes, bodying agents, drape and form control agents, smoothness agents, static control agents, wrinkle control agents, sanitization agents, drying agents, stain resistance agents, soil release agents, malodor control agentsr, dye fixatives, dye transfer inhibitors, color maintenance agents, anti-fading agents, color appearance restoration agents, brightness restoration agents, whiteness enhancers, anti-abrasion agents, fabric integrity agents, anti-wear agents, cleaning enhancers, defoamers, rinse aids, UV protection agents, sun fade inhibitors, insect repellents, mite control agents, enzymes, and mixtures thereof.

Any organic compound capable of delivering a desired fabric care benefit may be useful as a fabric care active in the articles and laundry kit of the present invention provided that the organic compound has a ClogP greater than about 1, more preferably greater than about 2.5, and even more preferably greater than about 3. Further, where the potential fabric care active consists of a mixture of organic compounds, at least about 25%, more preferably at least about 50%, and even more preferably at least about 75% by weight of the mixture will have a ClogP greater than about 1, more preferably greater than about 2.5, and even more preferably greater than about 3.

Since the fabric care actives used in the articles and kit of the present invention are not formulated into a bulk detergent or rinse-added fabric conditioning composition, it is possible to deliver a fabric care active to the solution in an effective concentration. By way of example, the use of enzymes, perfumes, bleaches and other actives in a wash solution in the presence of detergents actives is highly desirable. However, formulating such fabric care actives into a bulk detergent composition is well known to involve significant problems in terms of stability and potential degradation of the actives in the presence of detergents and bleaches. Attempts have been made to overcome these problems by lowering concentrations of actives, by adding stabilizers and by microencapsulating the fabric care actives. The kit of the present invention enables the user to dispense any fabric care active in the wash bath without reducing the concentration of the detergent or fabric care actives, without microencapsulating the fabric care actives, and without the use of additional materials to stabilize a bulk composition containing the desired actives. It is likewise well known that the bulk formulation of fabric care actives in a rinse-added fabric softener composition, especially concentrated fabric softener compositions, may experience stability and viscosity problems as well. Therefore, it is well known that there are a variety of fabric care actives that cannot be effectively combined with bulk detergent or fabric softener compositions, or alternatively, can only be used in such compositions at lower, sub-optimum concentrations.

Although not components of the individual fabric care compositions or articles, it is preferred that the laundry kit of the present invention will optionally contain a detergent and/or fabric softener for dispensing in the wash and rinse bath solutions. The detergent and fabric softener compositions that may be dispensed with the fabric care compositions and articles of the present invention may be virtually any detergent or softener composition that is commercially available. Detergent and fabric softener compositions useful with the kit of the present invention may be either scented or unscented. However, to allow the consumer the opportunity to select a preferred fragrance or fragrances, it is preferred that the optional detergent and fabric softener be unscented. Further, because the present invention focuses in part on unitization as a means for simplifying the preparation of laundry solutions, it is anticipated that an optional detergent or fabric softening composition may be provided in unitized form. The use of an optional detergent or fabric softener composition is limited to the laundry kits of the present invention and should not be confused as an optional component in the fabric care compositions or articles described herein.

A customized laundry solution prepared by dispensing one or more fabric care articles of the kit of the present invention may comprise either a wash or rinse bath solution. The kit is particularly useful for allowing the user to select a given fabric care benefit and dispensing one or more articles containing fabric care composition(s) that will deliver that benefit to the solution. Furthermore, it is anticipated that consumers using the kit will identify specific fabric care actives that are preferred for delivering a given fabric care benefit.

The laundry kit of the present invention will preferably contain two or more unitized doses of a variety of fabric care actives or mixtures of actives. These fabric care actives may be the same active or mixture of actives to provide the same fabric care benefit, a selection of different actives for providing the same fabric care benefit, or a selection of different actives for providing a variety of different fabric care benefits.

A kit containing a number of articles having different actives for delivering a variety of fabric care benefits is anticipated for those desiring a variety of fabric care benefits and for those who have not yet identified a set of preferred benefits or who have not yet determined the preferred active for delivering a given fabric care benefit. Such a "variety" kit would allow the user to experiment to identify the preferred fabric care benefits and a preferred fabric care active for delivering a desired benefit for a given load of fabrics. A variety of kits can contain a number of articles with different perfumes.

It is likewise anticipated that consumers will have identified, or with the assistance of associated instructions will identify, the fabric care benefits that are desired and the types articles that should be used to deliver those benefits. Therefore, it is anticipated that a laundry kit of the present invention will contain a number of different actives for delivering a given fabric care benefit. For instance, a kit containing an unscented detergent and/or fabric softener may comprise a number of perfume containing articles each having a different perfume active to allow the consumer to choose from amongst several fragrances. While it is anticipated that a given consumer may prefer a given perfume active, it is also likely that a consumer will have different perfume preferences depending on the types of fabrics being laundered or the setting where those fabrics will be worn. Specifically, it is expected that consumers will desire one fragrance for linens, a separate fragrance for fabrics worn at social occasions and special events and additional fragrances for undergarments, work clothes, athletic apparel etc. Furthermore, while it is preferred that a given kit will contain different types of fabric care actives such as different perfumes, it is likewise preferred that the kit will contain multiple doses or articles of the same fabric care composition to allow for repeat usage of that composition.

It is also well known that individuals commonly sort soiled fabrics into loads that contain similar types of fabrics such as whites, linens, colored fabrics, delicates and the like. Because these loads contain similar fabrics with similar fabric care needs, and because the consumer will typically desire the same fabric care benefits for the fabrics in such loads, it is also preferred that the laundry kit of the present invention will contain a variety of fabric care articles for delivering a fabric care benefit or set of benefits for loads of sorted fabrics. By way of example, for a given load of white fabrics, a laundry kit of the present invention might contain a detergent and/or fabric softener, and fabric care articles containing actives to insure that the fabrics are thoroughly cleaned and softened, their whiteness and integrity is maintained, and a chosen fragrance is imparted.

The laundry kit of the present invention will contain the fabric care articles selected by a consumer based on the personal preferences of the consumer and the fabric care needs of the fabrics to be laundered by the consumer. Such a kit may be pre-packaged to contain actives anticipated to be desired by the consumer, or assembled at the point of sale to contain actives selected by the consumer.

As used herein, "unitized" dosing continues to refer to an amount of a fabric care active that is sufficient for effectively treating a minimum volume of fabrics in a minimum volume of water. For instance, in North America, a typical load of fabrics laundered in an automated washing machine will contain about 5 to about 7 lbs of fabrics. The volume of water typically used in washing that volume of fabrics will depend on the efficiency of the rinse and the number of rinse cycles selected by the consumer, but typically will use about 17 gal to about 20 gal of water. It is anticipated that multiple doses of a given fabric care composition or articles containing the composition will be required for treating larger volumes of fabrics in larger volumes of water.

At present, automated washing machines commonly have built-in dispensers or dispensers that attach to the top of the agitator to dispense rinse-added compositions to the rinse bath solution. These dispensing devices include the dispensing drawers and agitator devices that are well known in the art. The opening on many of these devices is a factor that presently limits the size of a solid fabric care article that can be dispensed through such a dispenser. Where the machine includes a dispenser having an opening of limiting size, it may be necessary to place several smaller doses or articles in the dispensing device to insure that an effective amount of the active or mixture of actives is dispensed in the rinse bath. However, it is anticipated that the dispensing devices built into automated washing machines will in the future be modified to receive larger articles. Furthermore, where such a size limitation exists, it may be overcome by simply dispensing the unitized fabric care composition as a liquid, gel or some other flexible form that will fit through the openings of existing machine dispensers. Alternatively, articles or doses of the kit of the present invention may, regardless of form, be dispensed in the wash or rinse bath solution by placing it in a self-contained dispensing device or by dispensing it directly into the laundry solution at the appropriate time.

Because the laundry kit of the present invention will contain multiple doses of fabric care compositions it is preferred that each of the doses have identification means in the form of a tactile indicator or more preferably in the form of visual indicator by which the user of the kit may identify and distinguish between actives. Furthermore, visual indicators may be used to convey a variety of information concerning the articles and their use, such as indicating whether a given article may be dispensed in a wash and/or rinse bath and whether a given article may be dispensed in a solution containing other types of actives. Preferred visual indicators for use with the articles of the present invention include dyes and other colorings, shapes, sizes, opacity, clarity, pearlescence, and mixtures of the same. It is even more preferred that the articles will have a visual indicator that comprises a word, letter, number, icon and/or other symbol that is are printed, embossed, debossed, imprinted or molded onto the surface of the article.

It is preferred that the laundry kit will also include a set of associated instructions concerning the articles and their use in preparing a laundry solution to suit the individual preferences of the consumer. The instructions associated with the kits of the present invention will be not unlike the instructions described herein for use in association with the individual articles of the present invention. Preferably, the associated instructions will provide a consumer with sufficient information to select one or more fabric care articles for delivering a fabric care benefit that is desire by the consumer or needed for the proper maintenance of a given fabric. Further, the instructions will preferably instruct the consumer on how to combine a fabric care article with a detergent and/or fabric softening composition or other fabric care actives. The instructions associated with a kit of the present invention will preferably instruct the consumer on whether a given fabric care active may be dispensed in a wash or rinse bath solution. It is also preferred that the instructions include information concerning the visual indicators or other identification means that have been associated with the articles.

The associated instructions will preferably comprise printed materials such as package labels and package inserts that are provided with the product, brochures and magazine inserts, pre-recorded audio or visual instructions for broadcast via radio and television, for download from a global computer network and for playback via electronic means. As used herein, "pre-recorded" refers to instructions recorded on any electronic or computer readable medium. Further, the use of live demonstrations in retail establishments or in-home settings are likewise effective in providing instruction to the consumer concerning the use of the articles. Further, it is also preferred that the associated instructions indicate where the consumer may access more detailed information concerning the fabric care articles of the present invention and their use. Specifically, it is anticipated that the associated instructions will provide an address or site designation where detailed instructions may be downloaded from a global computer network such as the World Wide Web.

A laundry kit of the present invention will also preferably have a package for containing a plurality of fabric care articles, and if present, the optional detergent and/or fabric softeners and instructions. The packaging for the kits of the present invention will be similar to the packaging useful for the individual articles, with the obvious modification that the kit will contain a greater number of articles. More specifically, packaging for the laundry kit will preferably comprise individualized packaged articles, or packages containing multiple articles having the same fabric active or mixture of actives. It is preferred that child resistant means be incorporated into the packaging for the individual articles and/or for the kit as a whole, in order to prevent children from inadvertently accessing the articles and potential ingesting or choking on them. The packaging for the kit may be made from existing materials using conventional techniques.

IV. Customized Laundry Solution and Process for Preparing Same

The present invention also provides for a laundry bath solution prepared by dispensing in a generally aqueous laundry bath, one or more unitized doses or articles containing a fabric care composition of the present invention. The solution may comprise a pre-soak or wash or rinse cycle solutions prepared in an automated washing machine, manual washing device, tub or other container. The solution may optionally contain a detergent and/or fabric softening composition.

The fabric care actives used in the articles of the present invention have been described in detail with respect to the laundry compositions, articles and kits of the present invention. The amount of fabric care active used in the dispensed dosing or article will preferably be between about 1 and 99% of the fabric care composition. More preferably the active will be between about 2 and about 80%, even more preferably between 4 and about 60% and still even more preferably between about 10 and 50% by weight of the fabric care composition.

After the fabric care composition has been dispensed in the laundry solution, it is preferred that the solution contain between about 0.1 ppm and about 500 ppm of the fabric care active or mixture of actives in the laundry solution.

V. Methods of Using Fabric Care Articles

The typical consumer has developed a set of preferences concerning the characteristics and features that they desire in their clothes, linens and other fabric items. These preferred characteristics and features are the fabric care benefits that they wish to enjoy when the laundering of these items is complete. Pre-packaged bulk laundry compositions such as detergents and fabric softening compositions do not allow the consumer the opportunity to pick and choose the fabric care benefits to be obtained from the laundering process. Therefore, the present invention provides methods for customizing a laundry solution to deliver one or more specific fabric care benefits selected by the consumer. Such methods comprise the steps of choosing a fabric care benefit and dispensing into a pre-soak, wash and/or rinse bath solution a unitized dose of a fabric care composition having a fabric care active or mixture of actives between about 1% and about 99% by weight of the composition, that will impart the desired benefit to fabrics laundered in that solution.

The fabric care compositions, articles and dosing are as described in detail throughout this disclosure. A unitized dose or article may be dispensed directly into a wash and/or rinse bath solution. The fabric care compositions and articles containing the same, have been prepared from materials and manufactured so that they will rapidly dissolve in an aqueous solution across a broad range of pH levels, in both warm and cold water solutions, and when other materials are present in the solution.

Where the article is to be dispensed into a rinse bath solution but dispensing is desired at the beginning of the wash cycle, the article or dose may be placed in dispensing means for delayed dispensing. Dispensing means will include the dispensing devices that are built into commercially available washing machines such as dispensing drawers and top loaded agitator dispensers. Likewise, the dispensing means will also include self-contained dispensing devices that may be placed in the tub of the machine at the start of the wash cycle. As previously described, the self-contained dispensing devices that are particularly useful in the methods of the present invention are those that are designed to open during the spin cycle that follows the wash and precedes the first rinse cycle. When a self-contained dispensing device is used to dispense an article or dose, it is preferred that water or a liquid fabric softening composition also be added to the dispenser to aid in the dissolution and dispensing of the fabric care composition. More specifically, it is preferred that between about 5 ml and about 150 ml of water and/or liquid fabric softener be added to the self-contained device.

The method of preparing a customized laundry solution will optionally include the use of a scented or unscented detergent and/or fabric softener composition. Because it is anticipated that consumers will want the opportunity to choose the fragrance that will be deposited on their fabrics, it is preferred that such detergent and fabric softening compositions be unscented. The optional detergent and/or fabric softening composition may be any detergent or fabric softener that is known in the art and may be unitized or a measured amount of a bulk composition.

The method of preparing a customized laundry solution will optionally include the step of providing information to the consumer which may assist the consumer in selecting a fabric care composition, or an article or dose containing such a composition, that will deliver a desired fabric care benefit. This information is preferably provided in the form of instructions that may be used to guide the consumer as has been described herein in conjunction with the articles and laundry kits of the present invention.

VI. Merchandising Display and Methods of Identifying and Dispensing Laundry Articles for use by Consumer The present invention also provides a merchandising display or dispensing device and methods for dispensing the compositions, articles and laundry kits of the present invention from such a display. More specifically, it is anticipated that consumers will use the dispensing device to identify the fabric care compositions that will deliver the fabric care benefits that they desire, and obtain fabric care articles or unitized doses containing such compositions and to thereby assembly a customized laundry kit that they may use to prepare a customized laundry solution.

The merchandising display/dispensing device contains at least two different types of fabric care articles or doses of fabric care compositions and means for allowing an individual to select one or more types of the articles or doses in the dispensing device. The method of the present invention preferably further comprises a mechanism for conveying to a consumer a description of a suitable system of fabric care compositions or articles. This mechanism can be an interactive computer that prompts a consumer to input several (e.g., three to four) key pieces of information about the fabrics to be laundered and the fabric care benefits desired by the consumer, and based upon this information, provides the consumer with a recommendation or prescription of a system of fabric care products that will optimize the use of the products in the dispensing device.

In the preferred embodiment shown in the FIGURE, the dispensing device comprises a stand alone display for use in a retail establishment such as a grocery store, fabric or clothing outlet and adjacent to department and specialty stores such as in a shopping mall setting. In the embodiment shown in the FIGURE, the dispensing display 20 dispenses different types of fabric care compositions.

Dispensing display 20 can be in any suitable configuration. As shown in the FIGURE, dispensing display 20 comprises a front panel 22, a pair of side panels 24, a rear panel 26, a bottom 28, a top 30, a base 32, a display sign 34, and a discharge portion. The dispensing display 20 shown in the FIGURE preferably also comprises at least one partition 38, and more preferably, a plurality of partitions, in its interior for segregating different types of fabric care products. A plurality of products of each type are preferably vertically stacked between partitions 38. The discharge portion preferably comprises a plurality of openings or discharge ports 36. The fabric care articles or doses are preferably fed by gravity into the discharge ports 36 when a fabric care article is removed from the bottom of the stack. Alternatively, dispensing display 20 will not have front panel 22 and the fabric care articles or doses may be removed from between the partitions 38 without limitation. The dispensing display 20 can be made of any suitable material, including metal, wood, plastic, and cardboard.

The dispensing display device can contain any number of different types of fabric care compositions and articles. Typically, the dispensing device 20 will contain at least two different perfume compositions in article or other unitized dose form. Likewise, the device 20 will contain at least two non-perfume fabric care compositions in article or other dose form. It is also anticipated that display device 20 will also contain a detergent and/or fabric softener that may optionally be included in the laundry kits of the present invention. Dispensing display 20 will preferably provide a plurality of containers that are specifically designed to be filled with a variety of the fabric care articles or doses that are available at the dispensing display.

Dispensing display 20 is preferably labeled to assist the user or consumer in determining which types of fabric care compositions are best suited to meet the fabric needs of their fabrics and to deliver or impart the specific fabric care benefits that they desire. For example, it is anticipated that dispensing device 20 will provide with means such as sample cards for a consumer to preview the perfume compositions and articles that are available from the dispenser. Likewise, certain fabric care benefits may be imparted to the consumer's fabrics through a combination of fabric care actives in one or more fabric care compositions. Thus, it is preferred that dispensing display will provide instruction and information to the consumer on how to combine fabric care articles and dosing to achieve one or more fabric care benefits.

The individual products are preferably dispensed in packages containing quantities ranging from 1–10 products per package, and preferably between 2–9 products per package. It should also be noted that if one type of product is dispensed in a quantity of 10, then at least one different type of product is preferably dispensed in a quantity of less than 10. The packages containing such quantities of products are preferably some suitable, preferably flat (for stacking) plastic bag. The individual products inside the plastic bag may also be provided in their own individual wrapper, such as is described in U.S. Pat. No. 4,556,146.

To use the dispensing device 20, the consumer will pull the desired product package, or combinations of different products or product packages from the discharge portion 36 of the dispensing device. If the product is not the proper product for the consumer's needs, the consumer can put the product package back in the product storage bin at the top of the dispensing device 20 (if the dispensing device 20 is provided with an open top). After making the correct selection, the consumer can then pay for the packages of products at the check out counter at the front of the store.

The method of the present invention allows the consumer to more economically try a variety of different types of laundry products. It also allows the consumer to mix and match small, more affordable quantities of a variety of fabric care compositions in article and dose form to meet the consumer's individual needs. The dispensing device provides an easy to understand explanation of the different compositions and articles that can be selected as part of an individual's laundry system.

In other alternative embodiments, the dispensing device 20 can be provided with a mechanism 44 or means for conveying to a consumer a description of a suitable laundry system. Suitable mechanisms for conveying this information to a consumer can include, but are not limited to a chart that the consumer can read, a dial that the consumer can move to identify their fabric care needs and preferences and obtain an indication of a suitable laundry system, or an interactive computer. The latter type device (the interactive computer) can, for instance, prompt a consumer to input several (e.g., three to four) key pieces of information about their fabric care needs and preferences, and based upon this information, provide the consumer with a recommendation or prescription of a system of products that will optimize the use of the products in the dispensing device 20. Such key pieces of information can include the consumer's preferred detergent, whether a softener is used and if so, the identity of that softener, the desire for anti-static, anti-wrinkle, anti-bacterial agents and the like as well as the consumer's fragrance preferences for the different types of fabrics or items that the consumer will regularly launder.

In still other embodiments, more automated types of product selection and dispensing systems currently available could be used. By way of example, it is common to dispense laundry detergents and fabric softeners from vending-type machines located in or adjacent to self serve commercial laundry businesses and laundry rooms provided in residential complexes and dormitories. Such vending-type machines would provide a preferred method and apparatus for dispensing the articles and kits of the present invention.

Information concerning the fabric care needs of a given type of fabric or article of clothing may also be attached directly to the fabric or clothing item. Specifically, it is anticipated that fabric and clothing manufacturers will affix to their products labels, tags or other indices that will indicate how the consumer of that product should properly care for it, particularly during the laundering operation. More specifically, it is anticipated that the manufacturer may utilize the icons, or other visual indicators that are used in the present invention as identification means to distinguish between articles and other dose forms, to identify for the consumer the fabric care compositions that should be utilized in laundering that particular fabric or clothing item. Alternatively, a packaged unit dose article or articles of the present invention may be attached to a new fabric or item of clothing.

It is also preferred that the fabric care compositions and articles of the present invention may be distributed and promoted through other channels of trade. For instance, it is anticipated that when a consumer purchases a section of fabric, an article of clothing or other some other item that may require periodic laundering, the consumer will receive one or more packaged fabric care compositions in article or other unitized dose form for the consumer to use in laundering the purchased item. Alternatively, the consumer may receive a coupon or code with their purchase that is redeemable for one or more fabric care compositions in article or other unitized dose form for use in laundering the purchased item. In a further alternative, it is anticipated that consumers need not make such a purchase but may be entitled to receive one or more packaged fabric care compositions in article or other unitized dose form in exchange for providing information concerning their preferred fabric care benefits or some other laundry-related preferences. Such information may be provided in a face-to-face survey, via telephone, computer or other electronic means and need not occur in a retail environment.

It is also preferred that the fabric care compositions of the present invention in kit, article and other dose form, may be distributed and marketed with complementary products such as detergents, fabric softeners, automated washing machines and self-contained dispensing devices that are used within such machines. It is anticipated that the fabric care compositions of the present invention will be provided to the consumer with a purchase involving any one of these or other complementary products. "Complementary products" as used herein refers to those products that will be used in preparing a laundry solution or otherwise imparting a given fabric care benefit to fabrics as well as devices that may be used in carrying out a laundry operation on such fabrics.

What is claimed is:

1. An article of manufacture comprising: (i) a composition; and (ii) a water soluble film, wherein the composition comprises from about 1% to about 99% by weight of the composition of a perfume microcapsule;

wherein the composition is free of a detergent surfactant and is free of a fabric softening active; and wherein the water soluble film encases said fabric care composition.

2. The article of claim 1, wherein the composition comprises a unitized dose for dispensing in a laundry wash and/or rinse bath, wherein the unitized dose comprises a weight between about 0.05 g and about 60 g.

3. The article of claim 2, wherein the water soluble film comprises a material selected from a polyvinyl alcohol, hydroxypropyl methylcellulose, polyvinyl pyrrolidone, or a mixture thereof.

4. The article of claim 3, wherein the perfume microcapsule comprises a microcapsule that releases perfume by pressure.

5. The article of claim 3, wherein the perfume microcapsule comprises a moisture-activated microcapsule.

6. The article of claim 1, wherein the water soluble film comprises a polyvinyl alcohol.

7. The article of claim 6, wherein the perfume comprises a mixture of organic compounds of which at least 50% by weight of the perfume have a ClogP of at least about 2.7.

8. The article of claim 1, wherein the perfume comprises a mixture of organic compounds of which at least 75% by weight of the perfume have a ClogP of at least about 2.7.

9. The article of claim 1, wherein the article is packaged in a package.

10. A method of treating fabric comprising the step of delivering an article to an automatic laundry washing machine, wherein the article comprises:

(a) a composition, wherein the composition comprises a perfume that is between about 1% and about 99% by weight of the composition; and (b) a water soluble film, wherein the water soluble film encases said composition;

(c) wherein the article is free of a detergent surfactant and is free of a fabric softening active.

11. The method of claim 10, wherein the perfume comprises a perfume microcapsule.

12. The method of claim 11, wherein the perfume microcapsule comprises a microcapsule that releases perfume by pressure.

13. The method of claim 11, wherein the perfume microcapsule comprises a moisture-activated microcapsule.

14. The method of claim 11, wherein the water soluble film comprises a material selected from a polyvinyl alcohol, hydroxypropyl methylcellulose, polyvinyl pyrrolidone, or a mixture thereof.

15. The method of claim 14, wherein the water soluble film comprises a polyvinyl alcohol.

16. The method of claim 10, wherein the article is in the form of a capsule, tablet, pouch, sphere, or envelope.

17. The method of claim 10, wherein the perfume comprises a mixture of organic compounds of which at least 75% by weight of the perfume have a ClogP of at least about 2.7.

18. The method of claim 10, wherein the article comprises a visual indicator that comprises a word, letter, number, icon and/or other symbol that is are printed, embossed, debossed, imprinted or molded onto the surface of the article.

19. The method of claim 10, wherein the article comprises a dye or other colorings.

* * * * *

UNITED STATES PATENT AND TRADEMARK OFFICE

CERTIFICATE OF CORRECTION

PATENT NO. : 7,166,565 B2
APPLICATION NO. : 11/105798
DATED : January 23, 2007
INVENTOR(S) : Debra Sue Caswell et al.

It is certified that error appears in the above-identified patent and that said Letters Patent is hereby corrected as shown below:

Column 28
Line 46, delete "Symoosium" and insert -- Symposium --.

Column 46
Line 7, delete "," after the word "methyl-" and insert -- β --.

Column 48
Line 13, delete "licheniforns" and insert -- licheniforms --.

Column 53
Line 29, delete the three symbols "≦" and insert -- ≤ --.

Column 67
Line 34, delete "aryloky" and insert -- aryloxy --.

Column 70
Line 1, delete "," after the word "in".

Colunin 72
Line 21, after the word "hydroxyethyl" insert -- -N-methylamino --.
Line 22, after "amino]" delete "-".

Column 77
Line 26, delete "□" and insert -- ° --.

Column 128

Signed and Sealed this

Eighteenth Day of September, 2007

JON W. DUDAS
*Director of the United States Patent and Trademark Office*